(12) United States Patent
Fairhead et al.

(10) Patent No.: US 10,781,441 B2
(45) Date of Patent: Sep. 22, 2020

(54) MODIFYING BACTERIOPHAGE

(71) Applicant: PHICO THERAPEUTICS LTD, Cambridge (GB)

(72) Inventors: Heather Fairhead, Histon (GB); Adam Wilkinson, Chrishall (GB); Emmanuele Severi, Cambridge (GB)

(73) Assignee: Phico Therapeutics Ltd, Cambridge (GB)

( * ) Notice: Subject to any disclaimer, the term of this patent is extended or adjusted under 35 U.S.C. 154(b) by 24 days.

(21) Appl. No.: 16/092,087

(22) PCT Filed: Apr. 7, 2017

(86) PCT No.: PCT/EP2017/058468
§ 371 (c)(1),
(2) Date: Oct. 8, 2018

(87) PCT Pub. No.: WO2017/174809
PCT Pub. Date: Oct. 12, 2017

(65) Prior Publication Data
US 2019/0093100 A1    Mar. 28, 2019

(30) Foreign Application Priority Data
Apr. 8, 2016 (GB) .................................. 1606013.9

(51) Int. Cl.
*C12N 15/10* (2006.01)
*C12N 7/00* (2006.01)
(Continued)

(52) U.S. Cl.
CPC .......... *C12N 15/1037* (2013.01); *A61K 35/76* (2013.01); *C07K 14/005* (2013.01);
(Continued)

(58) Field of Classification Search
None
See application file for complete search history.

(56) References Cited

U.S. PATENT DOCUMENTS

| 6,310,191 B1 | 10/2001 | Collins et al. | |
| 2010/0239536 A1* | 9/2010 | Fairhead | A61K 9/0053 424/93.2 |
| 2015/0064770 A1 | 3/2015 | Lu et al. | |

FOREIGN PATENT DOCUMENTS

| DE | 102010013834 | 12/2010 |
| EP | 1 384 779 | 1/2004 |

(Continued)

OTHER PUBLICATIONS

Lin TY, et al. "A T3 and T7 recombinant phage acquires efficient adsorption and a broader host range," PLoS One. 2012;7(2):e30954.
(Continued)

*Primary Examiner* — Christian C Boesen
(74) *Attorney, Agent, or Firm* — Robin L. Teskin; Baker, Donelson, Bearman, Caldwell & Berkowitz PC

(57) ABSTRACT

A method for producing one or more hybrid bacteriophage host range determinant (HRD) sequences, which comprises: (1) identifying at least two DNA sequences, each encoding an HRD in a series of regions in the DNA sequence, wherein the HRDs are different from one another, (2) incorporating each region into a vector in which each region is flanked by a recognition site of a restriction enzyme capable of cutting DNA at a specific cleavage site outside of the recognition sequence, so that the cleavage site of the restriction enzyme is situated at the boundary of each region, wherein the cleavage site sequences of the regions from an individual series are different from one another and wherein the cleavage site sequences at the boundaries of corresponding regions from different series are the same; (3) treating the vectors with a restriction enzyme capable of cutting DNA at
(Continued)

| Strain/Phage | PTP238 | Phi33 | PTP47 | PTP92 |
|---|---|---|---|---|
| 2045 | + | - | - | + |
| 2290 | + | - | - | + |
| 2728 | + | - | - | + |
| 2937 | + | - | - | + |
| 2944 | + | - | + | - |
| 2948 | + | + | + | - |
| 3183 | + | - | - | + |
| 3215 | + | - | - | + | a specific cleavage site outside of the recognition sequence so as to generate a mixture of the regions; and (4) treating the mixture of the regions with a ligase to ligate them to form an array of DNA sequences encoding an array of hybrid HRDs.

20 Claims, 21 Drawing Sheets

Specification includes a Sequence Listing.

(51) Int. Cl.
A61K 35/76 (2015.01)
C07K 14/32 (2006.01)
C07K 14/005 (2006.01)
C40B 50/06 (2006.01)

(52) U.S. Cl.
CPC .............. C07K 14/32 (2013.01); C12N 7/00 (2013.01); C12N 2795/00022 (2013.01); C12N 2795/00032 (2013.01); C40B 50/06 (2013.01)

(56) References Cited

FOREIGN PATENT DOCUMENTS

| GB | 2451750 | 2/2009 |
|---|---|---|
| WO | 1998/033901 | 8/1998 |
| WO | 2002/007742 | 1/2002 |
| WO | 2002/040678 | 5/2002 |
| WO | 2004/113375 | 12/2004 |
| WO | 2009/019293 | 2/2009 |
| WO | 2016/055584 | 4/2016 |
| WO | 2016/055585 | 4/2016 |
| WO | 2016/055586 | 4/2016 |
| WO | 2016/055587 | 4/2016 |

OTHER PUBLICATIONS

Le S, et al. "Mapping the tail fiber as the receptor binding protein responsible for differential host specificity of Pseudomonas aeruginosa bacteriophages PaP1 and JG004," PLoS One. Jul. 9, 2013;8(7):e68562.

Pitts K, et al. "SASPject: Efficacy of SASPject against Pseudomonas aeruginosa ATCC 27853 in a Mouse Lung Model," 54th ICAAC, 2014. http://www.phicotx.co.uklwp-contentluploadsl2014/12/F1551.pdf.

Yoichi M, et al. "Alteration of tail fiber protein gp38 enables T2 phage to infect Escherichia coli O157:H7," J Biotechnol. Jan. 12, 2005;115(1):101-7.

Yu P, et al. "Isolation of Polyvalent Bacteriophages by Sequential Multiple-Host Approaches," Appl Environ Microbiol. Nov. 20, 2015;82(3):808-15.

* cited by examiner

FIG. 1

| Strain/Phage | PTP238 | Phi33 | PTP47 | PTP92 |
|---|---|---|---|---|
| 2045 | + | - | - | + |
| 2290 | + | - | - | + |
| 2728 | + | - | - | + |
| 2937 | + | - | - | + |
| 2944 | + | - | + | - |
| 2948 | + | + | + | - |
| 3183 | + | - | - | + |
| 3215 | + | - | - | + |

FIG. 2A

| 5' cs | 5' cs sequence | Module | 3' cs sequence | 3' cs | Source phage | Sequence of synthesised module fragment (BsaI restriction enzyme recognition sites are in bold; cleavage sites (cs) are in lower case. Any silent mutations made relative to the wild-type HRD sequences are underlined.) | Clone in pUC57 (-BsaI) |
|---|---|---|---|---|---|---|---|
| cs1 | CTCG | 1A | GGAT | cs2 | PTP92 | GGTCTCActcggCAATAACTCCTATGTGATCACCGACGAATCCAACATCCGAACCCAT ATCAACACAATGGCTGCGCCCGATTTGGGGGAATGTCGAGTTCTGGGGTCCGTGGA ACTTCGATCCGAATCTTAAACTCACTTTGAACGCTTTCAATGATAGCTCATACACCAg gatTGAGACC (SEQ ID NO: 9) | pSMG1 |
| cs1 | CTCG | 2A | GGAT | cs2 | PTP47 | GGTCTCActcggCAATAACTCCTATGTGATCACCGACGAATCCAACATCCGAACCCAT ATCAACACAATGGCTGCGCCCGATTTGGGGGAATGTCGAGTTCTGGGTCCGTGGA ACTTCAATCCTAACGAAGTTGACGCTTGGCTCATTCAATGACGGCCAGCATACCAg gatTGAGACC (SEQ ID NO: 10) | pSMG2 |
| cs2 | GGAT | 1B | GCGG | cs3 | PTP92 | GGTCTCAggatGACCAACAGCGGCGGCGAAAGACGTTGGTATCGCGTCCATGACGAGTT ATGCTGATGCGGCCATGTCATTCTTCAACTATGAAGCTCGATCCGAATCCGACCGGGCCCG CGCGGCCGTTATTCGTCGTGAGAAATGGATCGCGTGAGTGCGTATTCGGCTtGGAT TCTGACACAGCTGAAATGGGGCGGCTATTCTCTAGGTGCCGTCGCGTTCGAGATTG CCGGACTCCAACAGCTCATGAGCTGTGGTCATCCCACGCTGCCGCCGAACTGGAA CGGGCAGACCATCTGGAGGTCGGGAAACTTCAACCCAGACACCAAGGCGACTTTGGCA GCTCCGAATACGAGCGTCATCCCCTACACATATTCAGTTATGGGGCGTCCGGAATCGCAT CAACCGGACAGGTCGGTGCCATTCGCCGCCAGAAAACAACAGCCGTCACCAATACCCAGC CGCCATCACGTTCCATTCGCCGGCAGAAATATCAGGTCAACTTCGGCCtGGATGCGGAC AACGTGGTAAAGATCGGTGCGCCCACAACTACAACCAGGCGCGCGTGGTTCAGGTAGCTGTC CCGGCAACTACAACAACTACATCAACCAGGCGCGCGTGGTTCAGGTAGTCTTGGCGGCGT CGGTTCCTACGCGATCCTTgcgTGAGACC (SEQ ID NO: 11) | pSMG3 |
| cs2 | GGAT | 2B | GCGG | cs3 | PTP47 | GGTCTCAggatGGTCAACAGCGGCCGAAGGATGTAGGAATTGCTGACGCCGAGACGAGCT ATGCGGACGCGGCTATGTCGTTCTTCAACTATGAGGCTTGCGACGCCGGAATCG TGCTGCTGTAATTTCGTTTGTTGTTCGTGTAACGGGGCACGAGGCGTTCGTTCGGCCTGGAC ACGGACAACAAGCTGAAATGGGGCGGCTATTCTTCTAGTGCCGTCGCGTTCGAGATTG (SEQ ID NO:) | pSMG4 |

FIG. 2B

| | | | | | | |
|---|---|---|---|---|---|---|
| cs3 | GCGG | 1C | GGGA | cs4 | PTP92 | CCGACTCCAACAACCTCATGAGCCTGTGGTCATCCCACGCTGCCGCGGCGAACTGGAA CGGGCAGACCATCGGGAGGTCGGGGAACTTCAACCCAGACACCAAGGCGACTTTGGCA GCTCGCAATACGACGTCATCCCCTACAATATTCAGTTATGGGGCGTCCGGAATCGCAT CAACCCGGACAGTTCCGGTGCGTTGTTGTGGAAAACAACAGCGTCACCAATACCGCAGC CGCCATCACGTTCCATTCGCCGCAGAAATATCATGTCAACTTCGGCTGGATGCGGAC AACGTGGTAAAGATCGGTGCGGGCACAATGGGCGGCTAGCATATCCCATCATCCACT CCGGCAACTACAACAACTACAACCAGGCGCTGGTTCAGTGGTCTTGGCGAAGT CGGTTCCTATGGCATCTTTgcggtTGAGACC (SEQ ID NO: 12) | pSMG5 |
| cs3 | GCGG | 2C | GGGA | cs4 | PTP47 | GGTCTCAgcggTATTGGACACCTCCGCGCGGCAGCCGTCCATTGCCCgggaTGAGAC C (SEQ ID NO: 13) | pSMG6 |
| cs4 | GGGA | 1D | ACTC | cs5 | PTP92 | GGTCTCAgcggTTCTGGACTATGCCGCTCCAACCGCGACCGTTCGACCgggaTGAGAC C (SEQ ID NO: 14) | pSMG7 |
| cs4 | GGGA | 2D | ACTC | cs5 | PTP47 | GGTCTCAgggaACGATCATGGACAGTTCCAAGCTGTTCTactcTGAGACC (SEQ ID NO: 15) | pSMG8 |
| cs5 | ACTC | 1E | TGGG | cs6 | PTP92 | GGTCTCAgggaGTGGTTGTGGACGGTTCCATTCTCATCTactcTGAGACC (SEQ ID NO: 16) | pSMG9 |
| cs5 | ACTC | 2E | TGGG | cs6 | PTP47 | GGTCTCAactcGTCCTGCGATTCGACCTATCCAGCCAGCGCCAGTCCGACGGGCACCT GGGCTGATgggTGAGACC (SEQ ID NO: 17) | pSMG10 |
| cs6 | TGGG | 1F | AATG | cs7 | PTP92 | GGTCTCAactcGTTCTTGCGCGCAAACTACAATAGCGGTCAAAGGCTGCCGGAACTT GGGCTGCAtgggTGAGACC (SEQ ID NO: 18) | pSMG11 |
| cs6 | TGGG | 2F | AATG | cs7 | PTP47 | GGTCTCAtgggCTATGTGTATAACCGAGACTCCACCAACGGCGACTCGGCATCCCTAT TCCAGCGGGTAACGTAAaatgTGAGACC (SEQ ID NO: 19) | pSMG12 |
| | | | | | | GGTCTCAtggATATGTAGTGACGTAAaatgTGAGACC (SEQ ID NO: 20) | |

FIG. 5A

```
SPM-1   MITPELIPSPFAAQGDKDPIPQTSSTGFANLRDGYTPDYEISLASNNPQAKAVERKIQNQ 60
F8      MITPELIPSPFAAQGDKDPIPQTSSTGFANLRDGYTPDYEISLASNNPQAKAVERKIQNQ 60
PB1     MITPELIPSPFAAQGDKDPIPQTSSTGFANLRDGYTPDYEISLASNNPQAKAVERKIQNQ 60
C36     MITPELIPSPFAAQGDKDPIPQTSSTGFANLRDGYTPDYEISLASNNPQAKAVERKIQNQ 60
LBL3    MITPELIPSPFAAQGDKDPIPQTSSTGFANLRDGYTPDYEISLASNNPQAKAVERKIQNQ 60
Ph133   MITPELIPSPFAAQGDKDPIPQTSSTGFANLRDGYTPDYEISLASNNPQAKAVERKIQNQ 60
LMA2    MITPELIPSPFAAQGDKDPIPQTSSTGFANLRDGYTPDYEISLASNNPQAKVVERKIQNQ 60
KPP12   MITPELIPSPFAAQGDKDPIPQTSSTGFANLRDGYTPDYEISLASNNPQAKAVERKIQNQ 60
JG024   MITPELIPSPFAAQGDKDPIPQTSSTGFANLRDGYTPDYEISLASNNPQAKAVERKIQNQ 60
PTP92   MITPELIPSPFAAQGDKDPIPQTSSTGFANLRDGYTPDYEISLASNNPQAKAVERKIQNQ 60
NH-4    MITPELIPSPFAAQGDKDPIPQTSSTGFANLRDGYTPDYEISLASNNPQAKAVERKIQNQ 60
14-1    MITPELIPSPFAAQGDKDPIPQTSSTGFANLRDGYTPDYEISLASNNPQAKAVERKIQNQ 60
PTP47   MITPELIPSPFAAQGDKDPIPQTSSTGFANLRDGYTPDYEISLASNNPQAKAVERKIQNQ 60
SN      MITPELIPSPFAAQGDKDPIPQTSSTGFANLRDGYTPDYEISLASNNPQAKAVERKIQNQ 60
        ************************************************.*********

SPM-1   LFFIATQNAQAWQRQMAPPWFQGMPGGYEQNAEVVRVGNDGIMRRYRSMVNANASDPLSS 120
F8      LFFIATQNAQAWQRQMAPPWFQGMPGGYEQNAEVVRVGNDGIMRRYRSMVNANASDPLSS 120
PB1     LFFIATQNAQAWQRQMAPPWFQGMPGGYEQNAEVVRVGNDGIMRRYRSMVNANASDPLSS 120
C36     LFFIATQNAQAWQRQMAPPWFQGMPGGYEQNAEVVRVGNDGIMRRYRSMVNANASDPLSS 120
LBL3    LFFIATQNAQAWQRQMAPPWFQGMPGGYEQNAEVVRVGNDGIMRRYRSMVNANASDPLSS 120
Ph133   LFFIATQNAQAWQRQMAPPWFQGMPGGYEQNAEVVRVGNDGIMRRYRSMVNANAIDPLSS 120
LMA2    LFFIATQNAQAWQRQMAPPWFQGMPGGYEQNAEVVRVGNDGIMRRYRSMVNANASDPLSS 120
KPP12   LFFIATQNAQAWQRQMAPPWFQGMPGGYEQNAEVVRVGNDGIMRRYRSMVNANASDPLSS 120
JG024   LFFIATQNAQAWQRQMAPPWFQGMPGGYEQNAEVVRVGNDGIMRRYRSMVNANASDPLSS 120
PTP92   LFFIATQNAQAWQRQMAPPWFQGMPGGYEQNAEVVRVGNDGIMRRYRSMVNANASDPLSS 120
NH-4    LFFIATQNAQAWQRQMAPPWFQGMPGGYERNAEVVRVGNDGIMRRYRSMVNANASDPLSS 120
14-1    LFFIATQNAQAWQRQMAPPWFQGMPGGYEQNAEVVRVGNDGIMRRYRSMVNANASDPLSS 120
PTP47   LFFIATQNAQAWQRQMAPPWFQDMPGGYEQNAEVVRVGNDGIMRRYRSMVNANASDPLSS 120
SN      LFFIATQNAQAWQRQMAPPWFQGMPGGYEQNAEVVRVGNDGIMRRYRSMVNANASDPLSS 120
        **********************.*****.***************************** *****

SPM-1   TTWEEQPAWSVMRSNIPMPAGGSGLSSGGEVITTGRNFNDLLNGTWEFFSDSVVASQNA 180
F8      TTWEEQPAWSVMRSNIPMPAGGSGLSSGGEVITTGRNFNDLLNGTWEFFSDSVVASQNA 180
PB1     TTWEEQPAWSVMRSNIPMPAGGPGLSSGGEVITTGRNFNDLLNGTWEFFSDSVVASQNA 180
C36     TTWEEQPAWSVMRSSIPMPAGGPGLSSGGEVITTGRNFNDLLNGTWEFFSDSVVASQNA 180
LBL3    TTWEEQPAWSVMRSNIPMPAGGPGLSSGGEVITTGRNFNDLLNGTWEFFSDSVVIASQNA 180
Ph133   TTWEEQPAWSVMRSNIPMPAGGPGLSSGGEVITTGRNFNDLLNGTWEFFSDSVVASQNA 180
LMA2    TTWEEQPAWSAMRSNIPMPAGGPGLSSGGEVITTGRNFNDLLNGTWEFFSDSVVIASQNA 180
KPP12   TTWEEQPAWSAMRSNIPMPAGGPGLSSGGEVITTGRNFNDLLNGTWEFFSDSVVIASQNA 180
JG024   TTWEEQPAWSVMRTNIPMPAGGPGLSSGGEVITTGRNFNELLNGTWEFFSDAIVVASQNA 180
PTP92   TTWEEQPAWSVMRTNIPMPAGGPGLSSGGEVITTGRNFNELLNGTWEFFSDAIVVASQNA 180
NH-4    TTWEEQPAWSVMRTNIPMPAGGPGLSSGGEVITTGRNFNELLNGTWEFFSDAIVVASQNA 180
14-1    TTWEEQPAWSVMRSSIPMPAGGPGLSSGGEVITTGRNFNDLLNGTWEFFSDSVVIASQNA 180
PTP47   TTWEEQPAWSAMRSNIPMPAGGPGLSSGGEVITTGRNFNDLLNGTWEFFSDSVVIASQNA 180
SN      TTWEEQPAWSVMRSNIPMPAGGPGLSSGGEVITTGRNFNDLLNGTWEFFSDSVVASQNA 180
        **********.**.*.*********.***************.*********..*****
```

FIG. 5B

```
SPM-1   PVYPASAGAAAGMLEAKSWVSGANTFCVQRYTDRVGNVAVRGLNAGAWTNWMYAVNVMAL 240
F8      PVYPASAGAAAGMLEAKSWVSGANTFCVQRYTDRVGNVAVRGLNAGAWTNWMYAVNVMAL 240
PB1     PVYPASAGAAAGMLEAKSWISGSNTFCVQRYTDRVGNVAVRGLNAGAWTNWMYAVNVMAL 240
C36     PVYPASAGAAAGMLEAKSWISGSNTFCVQRYTDRVGNVAVRGLNAGAWTNWMYAVNVMAL 240
LBL3    PVYPASAGAAAGMLEAKSWVSGANTFCVQRYTDRVGNVAVRGLNAGAWTNWMYAVNVMAL 240
Phi33   PVYPASAGAAAGMLEAKSWVSGANTFCVQRYTDRVGNVAVRGLNAGAWTNWMYAVNVMAL 240
LMA2    PVYPASAGAAAGMLEAKSWVSGANTFCVQRYTDRVGNVAVRGLNAGAWTNWMYAVNVMAL 240
KPP12   PVYPASAGAAAGMLEAKSWVSGANTFCVQRYTDRVGNVALRGLNAGAWTNWMYAVNVMAL 240
JG024   PVYPASAGAAAGMLEAKSWVSGSNTFCVQRYTDRVGNVAVRGLNAGAWTNWMYAVNVMAL 240
PTP92   PVYPASAGAAAGMLEAKSWVSGSNTFCVQRYTDRVGNVAVRGLNAGAWTNWMYAVNVMAL 240
NH-4    PVYPASAGAAAGMLEAKSWVSGSNTFCVQRYTDRVGNVAVRGLNAGAWTNWMYAVNVMAL 240
14-1    PVYPASAGAAAGMLEAKSWISRSNTFCVQRYTDRVGNVAVRGLNAGEWTNWMYAVNVMAL 240
PTP47   PVYPASAGAAAGMLEAKSWVSGANTFCVQRYTDRVGNVAVRGLNAGAWTNWMYAVNVMAL 240
SN      PVYPASAGAAAGMLEAKSWVSGANTFCVQRYTDRVGNVAVRGLNAGAWTNWMYAVNVMAL 240
        *****************:*  :*******************:****** *************

SPM-1   QQGRVTYGVAAGSANAYTLTLVPQLQGGLVDGMVLRVKFNAMNTGASTINVSGFGSKAIV 300
F8      QQGRVTYGVAAGSANAYTLTLVPQLQGGLVDGMVLRVKFNAMNTGASTINVSGFGSKAIV 300
PB1     QQGRVTYGVAAGSANAYTLTLVPQLQGGLVDGMILRVKFNTVNTGASTINVSGFGAKAIV 300
C36     QQGRVTYGVAAGPANAYTLTLVPQLQGGLVDGMILRVKFNTVNTGASTINVSGFGAKAIV 300
LBL3    QQGRVTYGVAAGSANAYTLTLVPQLQGGLVDGMILRVKFNTMNTGASTINVSGFGAKAIV 300
Phi33   QQGRVTYGVAAGSANAYTLTLVPQLQGGLVDGMILRVKFNTMNTGASTINVSGLGAKAIV 300
LMA2    QQGRVTYGVAAGSANAYTLTLVPQLQGGLVDGMILRVKFNTMNTGATTINVSGLGAKAIV 300
KPP12   QQGRVTYGVAAGSANAYTLTLVPQLQGGLVDGMILRVKFNTMNTGASTINVSGLGAKAIV 300
JG024   QHGRVTYGIAAGPANAYTLTLVPQIQGGLVDGMILRVKFNTMNTGATTINVSGLGAKAIV 300
PTP92   QHGRVTYGTAAGPANAYTLTLVPQIQGGLVDGMILRVKFNTMNTGATTINVSGLGAKAIV 300
NH-4    QHGRVTYGTAAGPANAYTLTLVPQIQGGLVDGMILRVKFNTMNTGATTINVSGLGAKAIV 300
14-1    QQGRVTYGVAAGSANAYTLTLVPQLQGGLVDGMILRVKFNTMNTGATTINVSGLGAKAIV 300
PTP47   QQGRVTYGVAAGSANAYTLTLVPQLQGGLVDGMILRVKFNTMNTGASTINVSGLGAKAIV 300
SN      QQGRVTYGVAAGSANAYTLTLVPQLQGGLVDGMILRVKFNTMNTGASTINVSGLGAKAIV 300
        *:******:***.************:*******:******::****:******:*:****

SPM-1   GAANFPLTGGELGQGLIAELVFDATGDRWRILAGAPRIQVGNADQDYQAPSWKQVKDYVA 360
F8      GAANFPLTGGELGQGLIAELVFDATGDRWRILAGAPRIQVGNADQDYQAPSWKQVKDYVA 360
PB1     GAANFPLTGGELGQGLIAELVFDATGDRWRILAGAPRIQVGNADQDYQAPSWKQVKDYVA 360
C36     GAANFPLTGGELGQGLIAELVFDATGDRWRILAGAPRIQVGNADQDYQAPSWKQVKDYVA 360
LBL3    GAANFPLTGGELGQGLIAELVFDATGDRWRILAGAPRIQVGNADQDYQAPSWKQVKDYVA 360
Phi33   GAANFPLTGGELGQGLIAELVFDAAGDRWRILAGAPRIQVGNADQDYQAPSWKQVKDYVA 360
LMA2    GAANFPLTGGELGQGLIAELVFDAAGDRWRILAGAPRIQVGNADQDYQAPSWKQVKDYVA 360
KPP12   GAANFPLTGGELGQGLIAELVFDAAGDRWRILAGAPRIQVGNADQDYQAPSWKQVKDYVA 360
JG024   GAANFPLTGGELGQGLIAELVFDAAGDRWRILAGAPRIQVGNADQDYQAPSWKQVKDYVE 360
PTP92   GAANFPLTGGELGQGLIAELVFDAAGDRWRILAGAPRIQVGNADQDYQAPSWKQVKDYVE 360
NH-4    GAANFPLTGGELGQGLIAELVFDAAGDRWRILAGAPRIQVGNADQDYQAPSWKQVKDYVA 360
14-1    GAANFPLTGGELGQGLIAELVFDAAGDRWRILAGAPRIQVGNADQDYQAPSWKQVKDYVA 360
PTP47   GAANFPLTGGELGQGLIAELVFDAAGDRWRILAGAPRIQVGNADQDYQAPSWKQVKDYVA 360
SN      GAANFPLTGGELGQGLIAELVFDAAGDRWRILAGAPRIQVGNADQDYQAPSWKQVKDYVA 360
        ***********************:.*********************************:

SPM-1   SQKLTEVDWADVVNKPNVAIQDTTPWFANLELSDARPFIDFHFNNNRAKDFDYRFISEAD 420
F8      SQKLTEVDWADVVNKPNVAIQDTTPWFANLELSDARPFIDFHFNNNRAKDFDYRFISEAD 420
PB1     SQKLTEVDWADVVNKPNVAIQDTTPWFANLELSDARPFIDFHFNNNRAKDFDYRFISEAD 420
C36     SQKLTEVDWADVVNKPNVAIQDTTPWFANLELSDARPFIDFHFNNNRAKDFDYRFISEAD 420
LBL3    SQKLTEVDWADVVNKPNVAIQDTTPWFANLELSDARPFIDFHFNNNRAKDFDYRFISEAD 420
Phi33   SQKLTEVDWADVVNKPNVAIQDTTPWFANLELSDARPFIDFHFNSNRAKDFDYRLISEAD 420
LMA2    SQKLTEVDWADVVNKPNVAIQDTTPWFANLELSDARPFIDFHFNSNRAKDFDYRLISEAD 420
KPP12   SQKLTEVDWADVVNKPNVAIQDTTPWFANLELSDARPFIDFHFNNNRAKDFDYRFISEAD 420
JG024   SQKLTEVDWTDVVNKPNVAIQDTTPWFANLELSDARPFIDFHFNSNRAKDFDYRLISEAD 420
PTP92   SQKLTEVDWTDVVNKPNVAIQDTTPWFANLELSDARPFIDFHFNSNRAKDFDYRLISEAD 420
NH-4    SQKLTEVDWTDVVNKPNVAIQDTTPWFANLELSDARPFIDFHFNSNRAKDFDYRLISEAD 420
14-1    SQKLTEVDWTDVVNKPNVAIQDTTPWFANLELSDARPFIDFHFNSNRAKDFDYRLISEAD 420
PTP47   SQKLTEVDWADVVNKPNVAIQDTTPWFANLELSDARPFIDFHFNSNRAKDFDYRLISEAD 420
```

FIG. 5C

```
SN       SQKLTEVDWADVVNKPNVAIQDTTPWFANLELSDARPFIDFHFNSNPAKDFDYRLISEAD 420
         ********:****************************************,*********:****

SPM-1    GSMAFYSRQGSAGPTQDILFSRSNVTFLQPRLDVAKNLAYIANSGPLWQNTTADQPGWKF 460
F8       GSMAFYSRQGSAGPTQDILFSRSNVTFLQPRLDVAKNLAYIANSGPLWQNTTADQPGWKF 480
PB1      GSMAFYSRQGSAGPTQDILFSRSNVTFLQPRLDVAKNLAYIANSGPLWQNTTADQPGWKF 480
C36      GSMAFYSRQGSAGPTQDILFSRSNVTFLQPRLDVAKNLAYIANSGPLWQNTTADQPGWKF 480
LBL3     GSMAFYSRQGSAGPTQDILFSRSNVTFLQPRLDVAKNLAYIANSGPLWQNTTADQPGWKF 480
Phi33    GSLAFYSRQGSAGPTQDILFNRNSVTFFQPRLDVAKNLAYIANSGPLWQNTTADQPGWKF 480
LMA2     GSLAFYSRQGSAGPTQDILFNRNSVTFFQPRLDVAKNLAYIANSGPLWQNTTADQPGWKF 480
KPP12    GSMAFYSRQGSAGPTQDILFSRSNVTFLQPRLDVAKNLAYIANSGSLWQNTTADQPGWKF 480
JG024    GSLAFYSRQGSAGPTQDILFNRNSVTFFQPRLDVAKNLAYIANSGPLWQNTTADQPGWKF 480
PTP92    GSLAFYSRQGSAGPTQDILFNRNSVTFFQPRLDVAKNLAYIANSGPLWQNTTADQPGWKF 480
NH-4     GSLAFYSRQGSAGPTQDILFNRNSVTFFQPRLDVAKNLAYIANSGPLWQNTTADQPGWKF 480
14-1     GSLAFYSRQGSAGPTQDILFNRNSVTFFQPRLDVAKNLAYIANSGPIWQNTTADQPGWKF 480
PTP47    GSLAFYSRQGSAGPTQDILFNRNSVTFFQPRLDVAKNLAYIANSGPLWQNTTADQPGWKF 480
SN       GSLAFYSRQGSAGPTQDILFNRNSVTFFQPRLDVAKNLAYIANSGSLWQNTTADQPGWKF 480
         **:***************** * *** ***************** ***************

SPM-1    TFAQGVDANNNAVIAVNTTNPDGSYRSQIMRWDWASTNVIFNNRPLFAGQYVPWDSGNFD 540
F8       TFAQGVDANNNAVIAVNTTNPDGSYRSQIMRWDWASTNVIFNNRPLFAGQYVPWDSGNFD 540
PB1      TFAQGVDANNNAVIAVNTTNPDGSYRSQVMRWDWASTNVIFNNRPLFAGQYVPWDSGNFD 540
C36      TFAQGVDANNNAVIAVNTTNPDGSYRSQIMRWDWASTNVIFNNRPLFAGQYVPWDSGNFD 540
LBL3     TFAQGVDANNNAVIAVNTTNPDGSYRSQIMRWDWASTNVIFNNRPLFAGQYVPWDSGNFD 540
Phi33    TFAQGVDANNNAVIAVNTTNPDGSYRSQIMRWDWASTNVIFNNRPLFAGQYVPWDSGNFD 540
LMA2     TFAQGVDANNNAVIAVNTTNPDGSYRSQVMRWDWASTNVIFNNRPLFAGQYTPWDSGNFD 540
KPP12    TFAQGVDANNNAVIAVNTTNPDGSYRSQIMRWDWASTNVIFNNRPLFAGQYTPWDSGNFD 540
JG024    TFAQGVDANNNAVIAVNTTNPDGSYRSQVMRWDWASTNVIFNNRPLFAGQYTPWDSGNFD 540
PTP92    TFAQGVDANNNAVIAVNTTNPDGSYRSQVMRWDWASTNVIFNNRPLFAGQYTPWDSGNFD 540
NH-4     TFAQGVDANNNAVIAVNTTNPDGSYRSQVMRWDWASTNVIFNNRPLFAGQYTPWDSGNFD 540
14-1     TFAQGVDANNNAVIAVNTTNPDGSYRSQVMRWDWASTNVIFNDRPLFAGQYTPWDSGNFD 540
PTP47    TFAQGVDANNNAVIAVNTTNPDGSYRSQVMRWDWASTNVIFNNRPLFAGQYTPWDSGNFD 540
SN       TFAQGVDANNNAVIAVNTTNPDGSYRSQVMRWDWASTNVIFNNRPLFAGQYTPWDSGNFD 540
         *******************************:***************:*******:********

SPM-1    PATKLTVGTTNNISGPTGIRNTTSNTGNMNTWGSSSTTASYGNAALQIFGRGGGEPAAIY 600
F8       PATKLTVGTTNNISGPTGIRNTTSNTGNMNTWGSSSTTASYGNAALQIFGRGGGEPAAIY 600
PB1      PATKLTVGTTNNISGPTGIRNTTSNTGNMNTWGSSSTTASYGNAALQIFGRGGGEPAAIY 600
C36      PATKLTVGTTNNISGPTGIRNTTSNTGNMNTWGSSSTTASYGNAAVQIFGRGDGEPAAIY 600
LBL3     PATKLTVGTTNNISRPTGIRNTTSNTGNMNTWGSSSTTASYGNAALQIFGRGGGEPAAIY 600
Phi33    PSTKLTVNATNQIAGPTGIRNTNGNTGNMNTWGSGSTTASYGNAALQIFGKGGGEPAALY 600
LMA2     PSTKLTVNATNQIAGPTGIRNTNGNTGNMNTWGSSSTTASYGNAAIQIFGKGGGEPAAIY 600
KPP12    PSTKLTVNATNQIAGPTGIRNTNGNTGNMNTWGSSSTTASYGNAALQIFGKGGGEPAALY 600
JG024    PSTKLTVSATNQISGPTGIRNTNGNTGNMNTWGSGSTTASYGNAAIQIFGKGSGEPAAIY 600
PTP92    PSTKLTVSATNQISGPTGIRNTNGNTGNMNTWGSGSTTASYGNAAIQIFGKGGGEPAAIY 600
NH-4     PSTKLTVSATNQIAGPTGIRNTNGNTGNMNTWGSGSTTASYGNAAIQIFGKGSGEPAAIY 600
14-1     PSTKLTVSATNQIAGPTGIRNTNGNTGNMNTWGSGSTTASYGNAAIQIFGKGGGEPAAIY 600
PTP47    PSTKLTVSATNQIAGPTGIRNTNGNTGNMNTWGSGSTTASYGNAAIRIFGKGGGEPAAIY 600
SN       PSTKLTVRATNQIAGPTGIQNTNGNTGNMNTWGSGSTTASYGNAAIQIFGKGGGEPAAIY 600
         *:*****  ***:* ****:*** **:****************** *:***:* *****:*

SPM-1    FDNSQTGWYLGMDKDGQLKRAGWSLGNNSYVVTDESNIRMHVNGMSGAPVWGGQWFWGEW 660
F8       FDNSQTGWYLGMDKDGQLKRAGWSLGNNSYVVTDESNIRNHVNGMSGAPVWGGQWFWGEW 660
PB1      FDNSQTGWYLGMDKDGQLKRAGWSLGNNSYVVTDESNIRNHVNGMSGAPVWGGQWFWGEW 660
C36      FDNSQTGWYLGMDKDGQLKRAGWSLGNNSYVVTDESNIRFHVNSMAGTPVWGGNEFWGPW 660
LBL3     FDNSQTGWYLGMDKDGQLKRAGWSLGNNSYVVTDESNIRFHVNSMAGTPVWGGNEFWGPW 660
Phi33    FDNSQTGWYLGMDKDGQLKRAGWSLGNNAYVITDESNIRFHVNSMAGTPVWGGNEFWGPW 660
LMA2     FDNSQTGWYLGMDKDGQLKRAGWSLGNNSYVITDELNIRNHINGMAARPVWGGNEFWGPW 660
KPP12    FDNSQTGWYLGMDKDGQLKRAGWSLGNNAYVITDESNIRFHVNSMAGTPVWGGNEFWGSW 660
JG024    FDNSQTGWYLGMDKDGQLKRAGWSLGNNSYVITDESNIRTHINTMAARPIWGNVEFWGPW 660
PTP92    FDNSQTGWYLGMDKDGQLKRAGWSLGNNSYVITDESNIRTHINTMAARPIWGNVEFWGPW 660
NH-4     FDNSQTGWYLGMDKDGQLKRAGWSLGNNSYVITDESNIRTHINTMAARPIWGNVEFWGPW 660
14-1     FDNSQTGWYLGMDKDGRLKRAGWSLGNNSYVITDESNIRTHINTMAARPIWGNVEFWGPW 660
```

FIG. 5D

```
PTP47    FDNSQTGWYLGMDKDGQLKRAGWSLGNNSYVITDESNIRTHINTMAARPIWGNVEFWGPW 660
SN       FDNSQTGWYLGMDKDGQLKRAGWSLGNNSYVITDESNIRTHINTMAARPIWGGVEFWGPW 660
         ************:*:***********:**:*** *** *:* *:. *;**. *** *

SPM-1    NFNPNTKLTIKAGTQETSSTAIFSGTLPFAPIASLSDYSQAPLTIYN--SPTGPSAKPAV 718
F8       NFNPNTKLTIKAGTQETSSTAIFSGTLPFAPIASLSDYSQAPLTIYN--SPTGPSAKPAV 718
PB1      NFNPNTKLTIKAGTQETSSTAIFSGTLPFAPIASLSDYSQAPLTIYN--SPTGPSAKPAV 718
C36      NFNPNTKLTIKAGTQETSSTAIFSGTMPFAPIASLSDYSQAPLTIYN--SPTGPSAKPAV 718
LBL3     NFNPNTKLTIKAGTQETSSTAIFSGTMPFAPIASLSDYSQAPLTVYN--SPTGPSAKPAV 718
Phi33    NFNPNTKLTIKAGTQETSSTAIFSGTMPFAPIASLSDYSQAPLTVYN--APTGPSAKPAV 718
LMA2     NFNPNTKLTIKAGTQETSSTAIYSGTMPFAPIASLSDYSQAPLTIYN--APTGPSAKPAV 718
KPP12    NFNPNTKLTIKAGTQETSSTAIFSETMPFAPIASLSDYSQAPLTIYN--APTGPSAKPAV 718
JG024    NFDPNLKLTLNAFNDSSYTRMTNSGAKDVG-IASMTSYADAAMSFFNYEASNPTGPRAAV 719
PTP92    NFDPNLKLTLNAFNDSSYTRMTNSGAKDVG-IASMTSYADAAMSFFNYEASNPTGPRAAV 719
NH-4     NFNPNTKLTLGSFNDSQHTRMVNSAAKDVG-IASMTSYADAAMSFFNYEASTPTGNRAAV 719
14-1     NFDPNLKLTLNAFNDSSYTRMTNSGAKDVG-IASMTSYADAAMSFFNYEASNPTGPRAAV 719
PTP47    NFNPNTKLTLGSFNDGQHTRMVNSAAKDVG-IASMTSYADAAMSFFNYEASTPTGNRAAV 719
SN       NFNPNTKLTLGSFNDSQHTRMVNSAAKDVG-IASMTSYADAAMSFFNYEASTPTGNRAAV 719
         **:** ***:  : .:   :  *  :  ..  ***::.*::*.::.:*  :... .. :.**

SPM-1    IAFIRPGNWGAFFGIDTDNKLKWGGGSLGNNSREIADSSNIMNLWASNPTAPSWNGQTVW 778
F8       IAFIRPGNWGAFFGIDTDNKLKWGGGSLGNNSREIADSSNIMNLWASNPTAPSWNGQTVW 778
PB1      IAFIRPGNWGAFFGIDTDNKLKWGGGSLGNNSREIADSSNIMNLWASNPTAPSWNGQTVW 778
C36      IAFIRPGNWGAFFGIDTDNKLKWGGGSLGNSSREIADSSNIMNLWAANPTAPSWNGQTVW 778
LBL3     IAFIRPGNWGAFFGIDTDNKLKWGGGSLGNSSREIADSSNIMNLWAANPTAPTWNGQTIW 778
Phi33    IAFIRPGNWGAFFGIDTDNKLKWGGGSLGNSSREIADSSNIMNLWAANPTAPSWNGQTIW 778
LMA2     IAFIRPGNWGAFFGLDTDNKLKWGGGSLGNSSMEIADSSNIMNLWAANPTAPTWNGQTVW 778
KPP12    IAFIRPGNWGAFFGLDTDNKLKWGGGSLGNSSREIADSRNIMNLWAANPTAPTWNGQTVW 778
JG024    ISFVRNGSRGVLFGLDSDNKLKWGGYSLGAVAFEIADSNNLMSLWSSHAAAPNWNGQTIW 779
PTP92    ISFVRNGSRGVLFGLDSDNKLKWGGYSLGAVAFEIADSNNLMSLWSSHAAAPNWNGQTIW 779
NH-4     ISFVRNGARGVLFGLDTDNKLKWGGYSLGAVAFEIADSNNLMSLWSSHAAAPNWNGQTIW 779
14-1     ISFVRNGSRGVLFGLDSDNKLKWGGYSLGAVAFEIADSNNLMSLWSSHAAAPNWNGQTIW 779
PTP47    ISFVRNGARGVLFGLDTDNKLKWGGYSLGAVAFEIADSNNLMSLWSSHAAAPNWNGQTIW 779
SN       ISFVRNGARGVLFGLDTDNKLKWGGYSLGAVAFEIADSNNLMSLWSSHAAAPNWNGQTIW 779
         *:*:* *  *.:**:*:********* *** ;  :  *****  *:.*,** ,*****:*

SPM-1    RSGNFDPATKVDLNAANATNGSMIFNRISGTGSGIASSGRVGAINLQNGAHSGQAAAVTF 838
F8       RSGNFDPATKVDLNAANATNGSMIFNRISGTGSGIASSGRVGAINLQNGAHSGQAAAVTF 838
PB1      RSGNFDPATKVDLNAANATNGNMIFNRISGTGSGIASSGRVGAINLQNGAHSGQAAAVTF 838
C36      RSGNFDPATKVDLNAANATNGNMVFNRISGTGSGIASSGRVGAINLQNGAHSGQAAAVTF 838
LBL3     RSGNFDPATKVDLNAANATNGNMIFNRIAGTGSGIASSDRVGAISLQNGATAGAAAAVTF 838
Phi33    RSGNFDPATKVDLNAANATNGNMIFNRIAGTGSGIASSGRVGAINLQNGEHSGQAAAVTF 838
LMA2     RSGNFDPATKVDLNAPNATNGNMIFNRIAGTGSGIASSGRVGAISLQNGATAGAAAAVTF 838
KPP12    RSGNFDPATKVDLNAPNATNGNMIFNRIAGTGSGIASSGRVGAISLQNGATAGAAAAVTF 838
JG024    RSGNFNPDTKATLAARNTTSSPTIFS----YGASGIASTGQVGALVVENNSVTNTAAAITF 836
PTP92    RSGNFNPDTKATLAARNTTSSPTIFS----YGASGIASTGQVGALVVENNSVTNTAAAITF 836
NH-4     RSGNFNPDTKATLAARNTTSSPTIFS----YGASGIASTGQVGALVVENNSVTNTAAAITF 836
14-1     RSGNFNPDTKATLAARNTTSSPTIFS----YGASGIASTGQVGALVVENNSVTNTAAAITF 836
PTP47    RSGNFNPDTKATLAARNTTSSPTIFS----YGASGIASTGQVGALVVENNSVTNTAAAITF 836
SN       RSGNFNPDTKATLAARNTTSSPTIFS----YGASGIASTGQVGALVVENNSVTNTAAAITF 836
         *****:*  **. * * *:*..  :*.      .*****:.:***: ::*.  .  ***:**

SPM-1    ERGGSIFVNFGLDTDNVLKVGGGNLGANAYPVIHAGNYNNYINQALVQVGLGGVGSYGIF 898
F8       ERGGSIFVNFGLDTDNVLKVGGGNLGANAYPVIHAGNYNNYINQALVQVGLGGVGSYGIF 898
PB1      ERGGSIFVNFGLDTDNVLKVGGGNLGANAYPVIHAGNYNNYINQALVQVGLGGVGSYGIF 898
C36      ERGGSIFVNFGLDTDNVLKVGGGNLGANAYPVIHAGNYNNYINQALVQVGLGGVGSYGIF 896
LBL3     ERGGGFFVNFGLDTDNVLKVGGGNLGANAYPVIHAGNYNNYINQALVQVGLGGVGSYGIF 898
Phi33    ERGGSIFVNFGLDTDNVLKVGGGNLGANAYPVIHAGNYNNYINQALVQVGLEGVGSYGIF 898
LMA2     ERGGGFFVNFGLDTDNVLKVGGGNLGANAYPVIHAGNYNSYINQALVQVGLGGVGSYAAL 898
KPP12    ERGG-FFVNFGLDTDNVLKVGGGNLGANAYPVIHAGNYNSYINQALVQVGLGGVGSYAAL 897
JG024    HSPQKYQVNFGLDADNVVKIGGGTMGGVAYPIIHSGNYNNYINQALVQVGLGGVGSYAIL 896
PTP92    HSPQKYQVNFGLDADNVVKIGGGTMGGVAYPIIHSGNYNNYINQALVQVGLGGVGSYAIL 896
NH-4     HSPQKYQVNFGLDADNVVKIGGGTMGGVAYPIIHSGNYNNYINQALVQVGLGGVGSYAIL 896
```

FIG. 5E

```
14-1    HSPQKYQVNFGLDADNVVKIGGGTMGGVAYPIIHSGNYNNYINQALVQVGLGGVGSYGIF 896
PTP47   HSPQKYHVNFGLDADNVVKIGGGTMGGVAYPIIHSGNYNNYINQALVQVGLGEVGSYGIF 896
SN      HSPQKYQVNFGLDADNVVKIGGGTMGGVAYPIIHSGNYNNYINQALVQVGLGGVGSYGIF 896
           .   ******:***:*;***.:*. ***:**;****.***********  ****. :

SPM-1   AVLDNAAPIATVQPGVVVDGSILIYSSCAANYNSGQKPAGTWRCMGYVVNRDANTADSAT 958
F8      AVLDNAAPIATVQPGVVVDGSILIYSSCAANYNSGQKPAGTWRCMGYVVNRDANTADSAT 958
PB1     AVLDNAAPIATVQPGVVVDGSILIYSSCAANYNSGQKPAGTWRCMGYVVNRDANTPDSAT 958
C36     AVLDNAAPIATVQPGVVVDGSILIYSSCSANYNSGQRPAGTWRCMGYVVNRDANTPDSAT 959
LBL3    AVLDYAAPTATVQPGVIVDGSILIYSSCSAHYNSGQRPAGTWRCMGYVLNRDARDPDSAT 958
Phi33   AVLDNAAPTATVQPGVVVDGSILIYSSCAANYNSGKRPAGTWRCMGYVVNRDANTPDSAT 958
LMA2    AVYDTSAPASSVGPGTILDGSVLFYSSFNANFRSGTKPTGTWRCMGYILNRDGTNPDSAT 958
KPP12   AVYDTSAPASSVGPGTILDGSVLFYSSFDANFRSGTKPTGTWRCMGYVLNRDGTNPDSAA 957
JG024   AVLDTSAPAASIAPGTIMDSSKLFYSSCDSYRSSASPTGTWRCMGYVYNRDSTNGDSAS 956
PTP92   AVLDTSAPAASIAPGTIMDSSKLFYSSCDSYRSSASPTGTWRCMGYVYNRDSTNGDSAS 956
NH-4    AVLDTSAPAASIAPGTIMDSSKLFYSSCDSYRSSARPTGTWRCMGYVYNRDSTNGDSAS 956
14-1    AVLDNAAPIATVQPGVVVDGSILIYSSCAANYNSGQRPAGTWRCMGYVVNRDANTPDSAT 956
PTP47   AVLDYAAPTATVRPGVVVDGSILIYSSCAANYNSGQRPAGTWRCMGYVVNRDANTPDSAT 956
SN      AVLDNAAPTATVQPGVVVDGSILIYSSCAANYNSGQRPAGTWRCMGYVVNRDANTPDSAT 956
        ** * :** ::: **.::*.* *;***  : :.*. *:********; ***.   ***;

SPM-1   LFQRVT 964 (SEQ ID NO: 21)
F8      LFQRVT 964 (SEQ ID NO: 22)
PB1     LFQRVT 964 (SEQ ID NO: 23)
C36     LFQRVT 964 (SEQ ID NO: 24)
LBL3    LFQRVT 964 (SEQ ID NO: 25)
Phi33   LFQRVT 964 (SEQ ID NO: 26)
LMA2    LFQRVT 964 (SEQ ID NO: 27)
KPP12   LFQRVT 963 (SEQ ID NO: 28)
JG024   LFQRVT 962 (SEQ ID NO: 29)
PTP92   LFQRVT 962 (SEQ ID NO: 30)
NH-4    LFQRVT 962 (SEQ ID NO: 31)
14-1    LFQRVT 962 (SEQ ID NO: 32)
PTP47   LFQRVT 962 (SEQ ID NO: 33)
SN      LFQRVT 962 (SEQ ID NO: 34)
```

FIG. 6A

```
PTP92    1   GTGATCACACCCGAACTGATACCCAGTCCGTTTGCTGCGCAGGGCGACAA   50
             ||||||||||||||||||||||||.||||||||.||.|||||||.||
PTP47    1   GTGATCACACCCGAACTGATCCCCAGTCCGTTTGCCGCTCAGGGCGATAA   50

PTP92    51  AGACCCGATCCCGCAGACCTCTTCCACTGGCTTTGCCAACCTTCGCGACG   100
             |||||||||.||.||.|||||.||||||||||||.||.||||||||||||
PTP47    51  AGACCCGATTCCACAAACCTCCTCCACTGGCTTCGCAAACCTTCGCGACG   100

PTP92    101 GCTACACGCCGGACTACGAAATCAGCCTGGCGTCGAACAACCCGCAGGCC   150
             ||||.|||||||||||||||||||||||||||||||||||||||||||||
PTP47    101 GCTATACGCCGGACTACGAAATCAGCCTGGCGTCGAACAACCCGCAGGCC   150

PTP92    151 AAAGCGGTCGAGCGAAAGATTCAAAACCAACTCTTCTTCATCGCGACCCA   200
             |||||||||||||||.|||.|||||||||||||||||||||||||||||
PTP47    151 AAAGCGGTCGAGCGGAAAATTCAAAACCAACTCTTCTTCATCGCGACCCA   200

PTP92    201 GAACGCACAGGCGTGGCAGCGACAAATGGCGCCGCCGTGGTTTCAGGGCA   250
             ||||||||||||||||||||||||||||||||||||||||||||||||.||
PTP47    201 GAACGCACAGGCGTGGCAGCGACAAATGGCGCCGCCGTGGTTTCAGGACA   250

PTP92    251 TGCCTGGCGGCTACGAACAGAATGCAGAAGTCGTGCGCGTCGGCAATGAC   300
             ||||||||||||||||||||||||||||||||||||||||||||.||||||
PTP47    251 TGCCTGGCGGCTACGAACAGAATGCAGAAGTCGTGCGCGTCGGAAATGAC   300

PTP92    301 GGAATCATGCGCGCTATCGCTCCATGGTGAACGCAAACGCCAGCGATCC   350
             ||.||.||||||||.|||||.||||||||||||.||.||.||.|||||.||
PTP47    301 GGCATAATGCGGCGTTATCGTTCCATGGTGAATGCCAATGCGAGCGACCC   350

PTP92    351 TCTCAGCAGTACCACCTGGGAAGAGCAACCCGCCTGGTCAGTTATGCGCA   400
             |||||||||.||.||.|||||||||||.||||||||||.|||||.|..||||||.
PTP47    351 TCTCAGCAGCACGACTTGGGAAGAACAACCCGCATGGTCGGCGATGCGCT   400

PTP92    401 CCAACATACCGATGCCGGCTGGCGGCCCCGGTCTGTCTTCGGCGGCGAA   450
             |||||||.||||||||||||.||.|||||.||.||.||||||.|||||.|||
PTP47    401 CCAACATCCCGATGCCGGCCGGAGGCCCAGGCCTATCTTCTGGCGGAGAA   450

PTP92    451 GTCATCACCACCGGCCGCAACTTCAATGAATTGCTGAACGGAACCTGGGA   500
             ||||||||.|||||||||||||||||||.||.||.|.||.||.||.||||||
PTP47    451 GTCATCACGACCGGCCGCAACTTCAACGACCTGTTAAATGCGACGTGGGA   500

PTP92    501 ATTTTTCTCTGATGCAATCGTCGTGGCCTCTCAGAACGCTCCGGTGTATC   550
             .||.|||||||||.||.||||||..|.||.|||||||||.||.||.||.||||
PTP47    501 GTTCTTCTCTGATTCAGTGGTTATCGCTTCTCAGAATGCCCCCGTATATC   550

PTP92    551 CGGCGTCTGCGGCGCGGCAGCAGGAATGCTGGAGGCGAAATCTTGGGTG   600
             ||||.||.||.|||.||.||.|||||||||||||.|||||||||||||||
PTP47    551 CGGCTTCCGCTGGTGCCGCTGCTGGCATGTTGGAGGCGAAATCTTGGGTG   600

PTP92    601 TCCGGGTCAAATACGTTCTGCGTCCAACGCTACACTGATCGCGTCGGAAA   650
             ||||.||..||.||||||||||||||||||||||||||||||||||||.|||
PTP47    601 TCCGGAGCCAATACGTTCTGCGTCCAACGCTACACTGATCGCGTCGGGAA   650

PTP92    651 CGTCGCCGTGCGCGGGCTCAATGCCGGGGCCTGGACCAACTGGATGTACG   700
             ||||||.|||||||||||.|||||||||.||||||||.|||||||||||||.|
PTP47    651 CGTCGCTGTGCGCGGGCTTAATGCCGGAGCGTGGACCAACTGGATGTATG   700

PTP92    701 CTGTAAACGTCATGGCCCTCCAACACGGCCGTGTAACCTATGGAACCGCG   750
             |.|||||||||||||||||||||||||..||.||.||.||.|||||||..||||
PTP47    701 CGGTAAACGTCATGGCCCTTCAACAAGGTCGGGTCACCTATGGAGTCGCG   750

PTP92    751 GCCGGTCCGGCGAATGCCTACACCTTGACTCTCGTTCCGCAGATCCAAGG   800
             ||||.|||||||||.||.|||||||||.||.||.|||||||||||||||||
PTP47    751 GCCGGATCGGCGAACGCTTACACGTTGACGCTAGTTCCGCAGCTCCAAGG   800

PTP92    801 TGGTTTGGTAGATGGCATGATCCTTCGGGTCAAGTTCAACACCATGAACA   850
             ||||||||||||||||||||||||||||||||||||||||||||||||||
PTP47    801 TGGTTTGGTAGATGGCATGATCCTTCGGGTCAAGTTCAACACCATGAACA   850

PTP92    851 CCGCGCTACTACCATCAACGTCTCCGGACTCGGCGCCAAAGCCATCGTC   900
             ||.|||||||||||||||||||||||||||||||||||||||||||||||
PTP47    851 CCGGCGCTACTACCATCAACGTCTCCGGACTCGGCGCCAAAGCCATCGTC   900
```

FIG. 6B

```
PTP92   901  GGCGCGGCCAACTTCCCTCTCACTGGCGGCGAACTTGGCCAAGGACTCAT   950
             ||||||||||||||||||||| ||.||||||||||||||||||||||||
PTP47   901  GGCGCGGCCAACTTCCCTCTCACCGGCGGCGAACTTGGCCAAGGACTCAT   950

PTP92   951  CGCTGAGCTTGTCTTCGACGCAGCAGGCGACCGCTGGAGGATTCTGGCAG   1000
             |||||||||||||.|||||||||||||||||||||||||.||.||.||||
PTP47   951  CGCTGAGCTTGTATTCGACGCAGCAGGCGACCGCTGGAGAATCCTCGCAG   1000

PTP92  1001  GCGCGCCGCGCATCCAAGTCGGCAACGCCGATCAGGACTACCAGGCGCCG   1050
             ||||||.|| ||||||||| |||||||||||||||.||.|||||||.||.
PTP47  1001  GCGCGCCACGCATCCAAGTTGGCAACGCCGATCAAGATTACCAGGCCCCC   1050

PTP92  1051  AGTTGGAAGCAAGTTAAAGACTATGTCGAGTCCCAAAAGCTCACCGAAGT   1100
             ||.||||| ||.||.||.||.||.||.|||||||||||||||.||.||||
PTP47  1051  AGCTGGAAACAGGTGAAGGATTACGTCGCGTCCCAAAAGCTGACTGAAGT   1100

PTP92  1101  GGATTGGACGGATGTCGTCAACAAGCCGAACGTCGCTATCCAAGATACAA   1150
             |||.|||.|.||.||||||||||||||||||||||||||||||||.||.|
PTP47  1101  GGACTGGGCTGACGTCGTCAACAAGCCGAACGTCGCTATCCAAGCACCA   1150

PTP92  1151  CGCCGTGGTTCGCCAATCTGGAGCTGTCCGATGCTCGGCCTTTCATCGAT   1200
             |||||||||||||||||||||||||||||||||||||||||||||||||
PTP47  1151  CGCCGTGGTTCGCCAATCTGGAGCTGTCCGATGCTCGGCCTTTCATCGAT   1200

PTP92  1201  TTCCACTTCAACAGCAATCGCGCCAAAGATTTTGACTATCGGCTGATATC   1250
             |||||||||||||||||||||||||||||||||||||||||||||||||
PTP47  1201  TTCCACTTCAACAGCAATCGCGCCAAAGATTTTGACTATCGGCTGATATC   1250

PTP92  1251  TGAAGCAGACGGATCGCTGGCTTTCTATTCGCGGCAGGGGTCTGCTGGGC   1300
             ||||||||||||||||||||| ||||||||||||||||||||||||||||
PTP47  1251  TGAAGCAGACGGATCGCTGGCTTTCTATTCGCGGCAGGGGTCTGCTGGGC   1300

PTP92  1301  CTACCCAGGACATCCTGTTCAACCGAAATTCCGTGACTTTCTTCCAGCCG   1350
             |||||||||||||||||||||||||||||||||||||||||||||||||
PTP47  1301  CTACCCAGGACATCCTGTTCAACCGAAATTCCGTGACTTTCTTCCAGCCG   1350

PTP92  1351  CGACTCGATGTGGCGAAAAACCTCGCGTATATCGCGAACTCTGGCCCCCT   1400
             |||||||||||.||||||||||||||||||||||||||||||||||||||
PTP47  1351  CGACTCGATGTTGCGAAAAACCTCGCGTATATCGCGAACTCTGGCCCCCT   1400

PTP92  1401  TTGGCAGAACACCACCGCCGATCAGCCCGGTTGGAAATTCACCTTTGCAC   1450
             |||||||||||||||||||||||||||||||||||||||||||||||||
PTP47  1401  TTGGCAGAACACCACCGCCGATCAGCCCGGTTGGAAATTCACCTTTGCAC   1450

PTP92  1451  AAGGCGTGGACGCGAACAACAACGCGGTGATCGCAGTCAATACCACCAAT   1500
             ||| ||||||||||||||||||||||||||||||||||||||||||||||
PTP47  1451  AAGGCGTGGACGCGAACAACAACGCGGTGATCGCAGTCAATACCACCAAT   1500

PTP92  1501  CCGGACGGTTCCTATCGTTCACAGGTCATGCGATGGGACTGGGCGTCCAC   1550
             |||||||||||||||||||||||||||||||||||||||||||||||||
PTP47  1501  CCGGACGGTTCCTATCGTTCACAGGTCATGCGATGGGACTGGGCGTCCAC   1550

PTP92  1551  GAACGTCATATTCAACAACCGTCCGCTCTTCGCCGGTCAATACACCCCTT   1600
             ||||||||||||||||||||||||||||||||||||||||||||||||||
PTP47  1551  GAACGTCATATTCAACAACCGTCCGCTCTTCGCCGGTCAATACACCCCTT   1600

PTP92  1601  GGGATTCTGGGAACTTCGATCCTTCCACCAAGTTGACGGTGAGTGCCACG   1650
             ||||||||||||||||||||||||||||||||||||||||||||||||||
PTP47  1601  GGGATTCTGGGAACTTCGATCCTTCCACCAAGTTGACGGTGAGTGCCACG   1650

PTP92  1651  AACCAAATCTCCGGCCCAACCGGGATTCGGAATACCAACGGCAACACCGG   1700
             |||||||||.||||||||||||||||||||||||||||||||||||||||
PTP47  1651  AACCAAATCGCCGGCCCAACCGGGATTCGGAATACCAACGGCAACACCGG   1700

PTP92  1701  CAACATGAACACCTGGGGTTCCGGCTCCACGACGGCATCCTATGGCAATG   1750
             |||||||||||||||||||||||||||||||||||||||||||||||||
PTP47  1701  CAACATGAACACCTGGGGTTCCGGCTCCACGACGGCATCCTATGGCAATG   1750

PTP92  1751  CTGCCATTCAAATCTTCGGAAAAGGGGGCGGTGAGCCTGCCGCGATCTAT   1800
             |||||||||.|||||||||||||.||||||||||||||||||||||||||
PTP47  1751  CTGCCATTCGAATCTTCGGAAAAGGGGGCGGTGAGCCTGCCGCGATCTAT   1800

PTP92  1801  TTCGACAACTCCCAGACCGGATGGTATCTGGGCATGGACAAGGATGGACA   1850
             ||||||||||||||||||||||||||||||||||||||||||||||||||
PTP47  1801  TTCGACAACTCCCAGACCGGATGGTATCTGGGCATGGACAAGGATGGACA   1850

PTP92  1851  GCTCAAGCGGGCCGGCTGGTCC▓▓▓▓GCAATAACTCCTATGTGATCACCG   1900
```

FIG. 6C

```
                        |||||||||||||||||||||||||||||||||||||||||||||
PTP47    1851 GCTCAAGCGGGCCGGCTGGTCGAGCGGCAATAACTCCTATGTGATCACCG     1900

PTP92    1901 ACGAATCCAACATCCGAACCCATATCAACACAATGGCTGCGCGCCCGATT    1950
              ||||||||||||||||||||||||||||||||||||||||||||||||||
PTP47    1901 ACGAATCCAACATCCGAACCCATATCAACACAATGGCTGCGCGCCCGATT    1950

PTP92    1951 TGGGGGAATGTCGAGTTCTGGGGTCCGTGGAACTTCGATCCGAATCTTAA    2000
              ||||||||.|||||||||||||||||||||||||||||.||||.||
PTP47    1951 TGGGGGAATGTCGAGTTCTGGGGTCCGTGGAACTTCAATCCTAA------    1994

PTP92    2001 ACTCAC---TTTGAACGCT-------TTCAATGATAGC---TCATACACCA    2038
              |||   .|||  |||||        ||||||||..||  .||| ||||
PTP47    1995 ---CACGAAGTTG-ACGCTTGGCTCATTCAATGACGGCCAGCAT--ACCA    2038

PTP92    2039 AACGGACCAACAGCGGCGCGAAAGACGTTGGTATCGCGTCCATGACGAGT    2088
              ||||..||.|||||.||.||.||.||.||.||.|||||||||||.
PTP47    2039 AACGGGTCAACAGCGCCGCGAAGGATGTAGGAATTGCGTCCATGACGAGC    2088

PTP92    2089 TATGCTGATGCGGCCATGTCATTCTTCAACTATGAAGCCTCGAATCCGAC    2138
              ||||.||.||.|||.||||.|||||||||||||||.|||.|||.|||||
PTP47    2089 TATGCGGACGCGGCTATGTCGTTCTTCAACTATGAGGCTTCGACGCCGAC    2138

PTP92    2139 CGGGCCGCGCGGCCGTTATTTCGTTCGTGAGAAATGGATCGCGTGGAG    2188
              ||||...||.||.||.||.|||||||||.||.|.|||.||..|.||.||.|
PTP47    2139 CGGGAATCGTGCTGCTGTAATTTCGTTTGTTCGTAACGGGCACGAGGCG    2186

PTP92    2189 TGCTATTCGGCTTGGATTCTGACAACAAGCTGAAATGGGGCGGCTATTCT    2238
              |.||.||||||.|||||..|.|||||||||||||||||||||||||||||
PTP47    2189 TTCTGTTCGGCCTGGACACGGACAACAAGCTGAAATGGGGCGGCTATTCT    2238

PTP92    2239 CTAGGTGCCGTCGCGTTCGAGATTGCCGACTCCAACAACCTCATGAGCCT    2288
              ||||||||||||||||||||||||||||||||||||||||||||||||||
PTP47    2239 CTAGGTGCCGTCGCGTTCGAGATTGCCGACTCCAACAACCTCATGAGCCT    2288

PTP92    2289 GTGGTCATCCCACGCTGCCGCGCCGAACTGGAACGGGCAGACCATCTGGA    2338
              ||||||||||||||||||||||||||||.|||||.||||||||||||||
PTP47    2289 GTGGTCATCCCACGCTGCCGCGCCGAACTGGAACGGGCAGACCATCTGGA    2338

PTP92    2339 GGTCGGGAAACTTCAACCCAGACACCAAGGCGACTTTGGCAGCTCGCAAT    2388
              |||||||||||||||||||||||||||||||||||||||||||||||||
PTP47    2339 GGTCGGGAAACTTCAACCCAGACACCAAGGCGACTTTGGCAGCTCGCAAT    2388

PTP92    2389 ACGACGTCATCCCCTACAATATTCAGTTATGGGGCGTCCGGAATCGCATC    2438
              ||||||||||||||||||||||||||||||||||||||||||||||||||
PTP47    2389 ACGACGTCATCCCCTACAATATTCAGTTATGGGGCGTCCGGAATCGCATC    2438

PTP92    2439 AACCGGACAGGTCGGTGCGTTGGTTGTGGAAAACAACAGCGTCACCAATA    2488
              ||||||||||||||||||||||||||||||||||||||||||||||||||
PTP47    2439 AACCGGACAGGTCGGTGCGTTGGTTGTGGAAAACAACAGCGTCACCAATA    2488

PTP92    2489 CCGCAGCCGCCATCACGTTCCATTCGCCGCAGAAATATCACGTCAACTTC    2538
              |||||||||||||||||||||||||||||||||||||||.||||||||||
PTP47    2489 CCGCAGCCGCCATCACGTTCCATTCGCCGCAGAAATATCATGTCAACTTC    2538

PTP92    2539 GGCCTGGATGCGGACAACGTGGTAAAGATCGGTGGCGGCACAATGGGCGG    2588
              ||||||||||||||||||||||||||||||||||||||||||||||||||
PTP47    2539 GGCCTGGATGCGGACAACGTGGTAAAGATCGGTGGCGGCACAATGGGCGG    2588

PTP92    2589 CGTAGCATATCCCATCATCCACTCCGGCAACTACAACAACTACATCAACC    2638
              ||||||||||||||||||||||||||||||||||||||||||||||||||
PTP47    2589 CGTAGCATATCCCATCATCCACTCCGGCAACTACAACAACTACATCAACC    2638

PTP92    2639 AGGCGCTGGTTCAGGTAGGTCTTGGCGGCGTCGGTTCCTACGCGATCCTT    2688
              ||||||||||||||||.||||||||||||.||||||||..||.|.|||.||
PTP47    2639 AGGCGCTGGTTCAGGTGGGTCTTGGCGAAGTCGGTTCCTATGCATCTTT    2688

PTP92    2689 GCCCTATTGGACACCTCCGCGCCGGCAGCGTCCATTGCCCCGAGACGAT    2738
              |.|..|||.|||.|.|||.||.||.|||.||.||.||.|||||...|||
PTP47    2689 GCCCTTCTGGACTATGCCGCTCCAACCGCGACCGTTCGACCGAGGTGGT    2738

PTP92    2739 CATGGACAGTTCCAAGCTGTTCTCCGGTCCTGCGATTCGACCTATCGCA    2788
              ..|||.|||||||..||.||.||.||.|||||.||||...|.|.||| ||
PTP47    2739 TGTGGACGGTTCCATTCTCATCTCGGTCTTGCGCCGCAAACTA----CA    2785

PTP92    2789 GCAGDG---CCAGTCCGACGGGCACCTGGCGCTGCAGCCGTATCT-GTA    2834
              ..||||   ..||.||.|.|.||||||||||||||..||||.|| ||
```

FIG. 6D

```
PTP47    2786 ATAGCGGTCAAAGGCCTGCCGGAACTTGGCGCTGCAGGGGATATGTAGT-    2834

PTP92    2835 TAACCGAGACTCCACCAACGGC----GACTCGGCATCCCTATTCCAGCGG    2880
              .||||.||..|||.||   |    ||||.||..|||.|||||||.
PTP47    2835 CAACCGGGATGCCAACA----CTCCTGACTCCGCGACCCTTTTCCAGCGA    2880

PTP92    2881 GTAACGTAAGGGG    2889 (SEQ ID NO: 35)
              ||.||||||||
PTP47    2881 GTGACGTAAGGGG    2889 (SEQ ID NO: 36)
```

FIG. 7A

```
PTP92    MITPELIPSPFAAQGDKDPIPQTSSTGFANLRDGYTPDYEISLASNNPQAKAVERKIQNQ
PTP47    MITPELIPSPFAAQGDKDPIPQTSSTGFANLRDGYTPDYEISLASNNPQAKAVERKIQNQ
         ************************************************************

PTP92    LFFIATQNAQAWQRQMAPPWFQGMPGGYEQNAEVVRVGNDGIMRRYRSMVNANASDPLSS
PTP47    LFFIATQNAQAWQRQMAPPWFQDMPGGYEQNAEVVRVGNDGIMRRYRSMVNANASDPLSS
         ********************** *************************************

PTP92    TTWEEQPAWSVMRTNIPMPAGGPGLSSGGEVITTGRNFNELLNGTWEFFSDAIVVASQNA
PTP47    TTWEEQPAWSAMRSNIPMPAGGPGLSSGGEVITTGRNFNDLLNGTWEFFSDSVVIASQNA
         ********** **.**********************:**********.;*;*****

PTP92    PVYPASAGAAAGMLEAKSWVSGSNTFCVQRYTDRVGNVAVRGLNAGAWTNWMYAVNVMAL
PTP47    PVYPASAGAAAGMLEAKSWVSGANTFCVQRYTDRVGNVAVRGLNAGAWTNWMYAVNVMAL
         **********************;*************************************

PTP92    QHGRVTYGTAAGPANAYTLTLVPQIQGGLVDGMILRVKFNTMNTGATTINVSGLGAKAIV
PTP47    QQGRVTYGVAAGSANAYTLTLVPQLQGGLVDGMILRVKFNTMNTGATTINVSGLGAKAIV
         *;******.***.***********;***********************************

PTP92    GAANFPLTGGELGQGLIAELVFDAAGDRWRILAGAPRIQVGNADQDYQAPSWKQVKDYVE
PTP47    GAANFPLTGGELGQGLIAELVFDAAGDRWRILAGAPRIQVGNADQDYQAPSWKQVKDYVA
         ***********************************************************.

PTP92    SQKLTEVDWTDVVNKPNVAIQDTTPWFANLELSDARPFIDFHFNSNRAKDFDYRLISEAD
PTP47    SQKLTEVDWADVVNKPNVAIQDTTPWFANLELSDARPFIDFHFNSNRAKDFDYRLISEAD
         *********;**************************************************

PTP92    GSLAFYSRQGSAGPTQDILFNRNSVTFFQPRLDVAKNLAYIANSGPLWQNTTADQPGWKF
PTP47    GSLAFYSRQGSAGPTQDILFNRNSVTFFQPRLDVAKNLAYIANSGPLWQNTTADQPGWKF
         ************************************************************

PTP92    TFAQGVDANNNAVIAVNTTNPDGSYRSQVMRWDWASTNVIFNNRPLFAGQYTPWDSGNFD
PTP47    TFAQGVDANNNAVIAVNTTNPDGSYRSQVMRWDWASTNVIFNNRPLFAGQYTPWDSGNFD
         ************************************************************

PTP92    PSTKLTVSATNQISGPTGIRNTNGNTGNMNTWGSGSTTASYGNAAIQIFGKGGGEPAAIY
PTP47    PSTKLTVSATNQIAGPTGIRNTNGNTGNMNTWGSGSTTASYGNAAIRIFGKGGGEPAAIY
         *************;********************************;*************

PTP92    FDNSQTGWYLGMDKDGQLKRAGWSLSNNSYVITDESNIRTHINTMAARPIWGNVEFWGPW
PTP47    FDNSQTGWYLGMDKDGQLKRAGWSLSNNSYVITDESNIRTHINTMAARPIWGNVEFWGPW
         ************************************************************

PTP92    NFDPNLKLTLNAFNDSSYTRVTNSGAKDVGIASMTSYADAAMSFFNYEASNPTGPRAAVI
PTP47    NFNPNTKLTLGSFNDGQHTRVVNSAAKDVGIASMTSYADAAMSFFNYEASTPTGNRAAVI
         **;**.****.;***..;*****;************************.****.*****

PTP92    SFVRNGSRGVLFGLDSDNKLKWGGYSLGAVAFEIADSNNLMSLWSSHAAAPNWNGQTIWR
PTP47    SFVRNGARGVLFGLDTDNKLKWGGYSLGAVAFEIADSNNLMSLWSSHAAAPNWNGQTIWR
         ******;********;********************************************

PTP92    SGNFNPDTKATLAARNTTSSPTIFSYGASGIASTGQVGALVVENNSVTNTAAAITFHSPQ
PTP47    SGNFNPDTKATLAARNTTSSPTIFSYGASGIASTGQVGALVVENNSVTNTAAAITFHSPQ
         ************************************************************
```

FIG. 7B

```
PTP92    KYQVNFGLDADNVVKIGGGTMGGVAYPIIHSGNYNNYINQALVQVGLGGVGSYAILAXLD
PTP47    KYHVNFGLDADNVVKIGGGTMGGVAYPIIHSGNYNNYINQALVQVGLGEVGSYGIFAXLD
         **.*********************************************** ****.*.****

PTP92    TSAPAASIAPGXIMDSSKLFYXSCDSTYRSSASPTGTWRCMXYVYNRDSTNGDSASLFQR
PTP47    YAAPTATVRPGXVVDGSILIYXSCAANYNSGQRPAGTWRCMXYVVNRDANTPDSATLFQR
         :**:*:: **.::*.* *:**** :.*.*.  *:********* ***::. ***:****

PTP92    VT  (SEQ ID NO: 30)
PTP47    VT  (SEQ ID NO: 33)
         **
```

FIG. 8

MITPELIPSPFAAQGDKDPIPQTSSTGFANLRDGYTPDYEISLASNNPQAKAVERKIQNQLF
FIATQNAQAWQRQMAPPWFQGMPGGYEQNAEVVRVGNDGIMRRYRSMVNANAIDPLSSTTWE
EQPAWSVMRSNIPMPAGGPGLSSGGEVITTGRNFNDLLNGTWEFFSDSVVVASQNAPVYPAS
AGAAAGMLEAKSWVSGANTFCVQRYTDRVGNVAVRGLNAGAWTNWMYAVNVMALQQGRVTYG
VAAGSANAYTLTLVPQLQGGLVDGMILRVKFNTMNTGASTINVSGLGAKAIVGAANFPLTGG
ELGQGLIAELVFDAAGDRWRILAGAPRIQVGNADQDYQAPSWKQVKDYVASQKLTEVDWADV
VNKPNVAIQDTTPWFANLELSDARPFIDFHFNSNRAKDFDYRLISEADGSLAFYSRQGSAGP
TQDILFNRNSVTFFQPRLDVAKNLAYIANSGPLWQNTTADQPGWKFTFAQGVDANNNAVIAV
NTTNPDGSYRSQIMRWDWASTNVIFNNRPLFAGQYVPWDSGNFDPSTKLTVNATNQIAGPTG
IRNTNGNTGNMNTWGSGSTTASYGNAALQIFGKGGGEPAALYFDNSQTGWYLGMDKDGQLKR
AGWSL*NNSYVITDESNIRTHINTMAARPIWGNVEFWGPWNFNPNTKLTLGSFNDGQHTR*T*
*NSGAKDVGIASMTSYADAAMSFFNYEASNPTGPRAAVISFVRNGSRGVLFGLDSDNKLKWGG*
*YSLGAVAFEIADSNNLMSLWSSHAAAPNWNGQTIWRSGNFNPDTKATLAARNTTSSPTIFSY*
*GASGIASTGQVGALVVENNSVTNTAAAITFHSPQKYQVNFGLDADNVVKIGGGTMGGVAYPI*
*IHSGNYNNYINQALVQVGLGGVGSYAILA*LDYAAPTATVRPG*IMDSSKLFY*SCDSTYRS*
*SASPTGTWRCM*YVYNRDSINGDSASLFQRVT*

(SEQ ID NO: 37)

MODIFYING BACTERIOPHAGE

RELATED APPLICATION INFORMATION

This application is a U.S. National Phase Application submitted under 35 U.S.C. 371 based on International Application No. PCT/EP2017/058468 filed Apr. 7, 2017 (published as WO2017/174809 on Oct. 12, 2017) which claims the benefit of United Kingdom Patent Application 1606013.9 filed Apr. 8, 2016, each of which is hereby incorporated by reference in its entirety.

SEQUENCE LISTING DISCLOSURE

This application includes as part of its disclosure a biological sequence listing which is being concurrently submitted through EFS-Web. Said biological sequence listing is contained in a file named "43297o3401.txt" which was created on Oct. 8, 2018, and has a size of 138,613 bytes, and is hereby incorporated by reference in its entirety.

INTRODUCTION

The present invention relates to a method for producing hybrid bacteriophage host range determinant (HRD) sequences. The present invention is particularly suited for providing a recombinant phage bearing hybrid HRDs having a broad host range.

BACKGROUND

The World Health Organisation's 2014 report on global surveillance of antimicrobial resistance reveals that antibiotic resistance is a global problem that is jeopardising the ability to treat common infections in the community and hospitals. Without urgent action, the world is heading towards a post-antibiotic era, in which common infections and minor injuries, which have been treatable for decades, can once again kill (WHO, 2014). Antibiotic resistance complicates patients' recovery from even minor operations and is increasingly causing treatment failures. In fact, there are now strains of some genera of bacteria circulating globally which are resistant to all available antibiotics. Such strains commonly fall within the scope of the so-called ESKAPE pathogens—*Enterococcus faecium, Staphylococcus aureus, Klebsiella pneumoniae, Acinetobacter baumannii, Pseudomonas aeruginosa* and *Enterobacter* species (Boucher et al., 2009). The term ESKAPE pathogens was coined by Boucher et al., to emphasize that these bacteria currently cause a majority of hospital infections in the US and Europe and can effectively "escape" the majority, if not all, available antibiotics with panantibiotic-resistant infections now occurring. The death rate for patients with serious infections caused by common bacteria treated in hospitals is approximately twice that of patients with infections caused by the same non-resistant bacteria, e.g. people with methicillin-resistant *Staphylococcus aureus* (MRSA) infections are estimated to be 64% more likely to die than people with a non-resistant form of the infection (WHO, 2014). Of the Gram positive bacteria, methicillin resistant *S. aureus* continues to be a major cause of morbidity and mortality in hospitals in the US and Europe. However, in more recent years, several highly resistant Gram negative pathogens, including *Acinetobacter* species, multidrug resistant (MDR) *P. aeruginosa*, and carbapenem-resistant *Klebsiella* species and *Escherichia coli*, have emerged as major pathogens causing serious, and sometimes untreatable, infections. Advances in medicine mean that increasingly complex procedures take place: and these advances are leading to a growing number of elderly patients and patients undergoing surgery, transplantation, and chemotherapy all of which will produce an even greater number of immunocompromised individuals at risk of these infections (Walker et al., 2009). This phenomenon has led to a greater dependence on, and requirement for, effective antibiotics.

*P. aeruginosa* is one bacterium which is frequently multi-drug resistant (MDR) having intrinsic resistance due to low permeability of its outer membrane limiting drugs getting into the cell, and a multitude of efflux pumps to expel any drugs that successfully manage to enter the cell. *P. aeruginosa* is also acquiring additional resistance mechanisms, including resistance to the "antibiotics of last resort" for Gram negatives, the carbapenems. *P. aeruginosa* causes approximately 10% of all hospital acquired infections and is the second leading cause of hospital-acquired pneumonia, which accounts for 50% of all hospital-acquired infection prescribing. *P. aeruginosa* infections in hospitals commonly require intravenous (IV) treatment with current standard of care for *P. aeruginosa* infections dictating that patients are treated with at least two antibiotics. Unfortunately, resistance frequently develops in patients during therapy. With so few new classes of antibiotic developed and approved for market within the last 30-40 years, there is a critical need for novel, safe and effective antibacterial agents.

One alternative to current antibiotics is bacteriophage-based medicines. Bacteriophage (or phage) have been used as medicines for the treatment of bacterial infections since the 1920s or 30s.

Recent developments include the use of phage as the basis for modification to make tailored gene delivery vehicles, which can be used for the delivery of genes encoding toxic proteins to target pathogenic bacteria. Such an approach is described in the SASPject system (WO2009/019293), in which bacteriophage are engineered to be non-lytic, thus ultimately non-viable, and to carry a SASP gene expression cassette, which is delivered into the targeted bacteria, which leads to rapid SASP expression. SASP are Small Acid-soluble Spore Proteins, which protect the DNA of Gram positive bacterial endospores during dormancy. However, upon expression of SASP in vegetative cells, rapid binding of SASP to the cell's DNA in a non-sequence specific manner (Nicholson et al., 1990) leads to rapid cell death.

However, generally, bacteriophage are specific to their bacterial host. Thus a phage specific to one bacterial host may be of little use when seeking to treat an infection caused by another bacterial host which the phage cannot infect. For useful medicines, the challenge is to provide bacteriophage compositions which can be used to treat infection from a variety of bacterial strains in an effective way.

One way to meet this challenge is by selecting for bacteriophage based upon their ability to infect a broad range of bacterial strains (broad host range phage). However, this approach is limited, as a single phage usually has insufficient host range due to the plasticity of the bacterial cell surface, especially in Gram negative bacteria (Carlton, 1999; Kutateladze and Adamia, 2010).

Another way is to select a mixture or a "cocktail" of phage to ensure broad coverage across the range of bacterial strains. To this end, cocktails of wild type phage have been used to ensure sufficient spectrum of activity against clinical strains of bacteria (Burrowes and Harper, 2012). Such cocktails can consist of up to 20 different and unrelated phage (Abedon 2008). However, the manufacturing and testing such a large cocktail of phage can be complex.

Therefore there remains a need to provide improved bacteriophage having a broad host range for use in treating bacterial infections in medicine as well as inhibiting or preventing bacterial cell growth in medical and non-medical situations.

SUMMARY OF INVENTION

The present invention provides a method for producing one or more hybrid bacteriophage host range determinant (HRD) sequences, which comprises: (1) identifying at least two DNA sequences, each encoding an HRD in a series of regions in the DNA sequence, wherein the HRDs are different from one another, (2) incorporating each region into a vector in which each region is flanked by a recognition site of a restriction enzyme capable of cutting DNA at a specific cleavage site outside of the recognition sequence, so that the cleavage site of the restriction enzyme is situated at the boundary of each region, wherein the cleavage site sequences of the regions from an individual series are different from one another and wherein the cleavage site sequences at the boundaries of corresponding regions from different series are the same; (3) treating the vectors with a restriction enzyme capable of cutting DNA at a specific cleavage site outside of the recognition sequence so as to generate a mixture of the regions; and (4) treating the mixture of the regions with a ligase to ligate them to form an array of DNA sequences encoding an array of hybrid HRDs.

In an aspect the present invention provides a method for producing one or more hybrid bacteriophage host range determinant (HRD) sequences, which comprises: (1) identifying at least two DNA sequences, each encoding an HRD in a series of regions in the DNA sequence, wherein the HRDs are different from one another, (2) incorporating each region into a vector in which each region is flanked by a Type IIS or Type IIB restriction enzyme recognition site so that the cleavage site of the Type IIS or Type IIB restriction enzyme is situated at the boundary of each region, wherein the cleavage site sequences of the regions from an individual series are different from one another and wherein the cleavage site sequences at the boundaries of corresponding regions from different series are the same; (3) treating the vectors with a Type IIS or Type IIB restriction enzyme so as to generate a mixture of the regions; and (4) treating the mixture of the regions with a ligase to ligate them to form an array of DNA sequences encoding an array of hybrid HRDs The method of the present invention allows for identifying regions of bacteriophage host range determinant (HRD) proteins which are both essential and sufficient for determining the host range conferred by an HRD protein, when such regions are incorporated into the sequence of a chimeric HRD protein, where two or more heterologous HRD proteins form the chimeric protein. In so doing, the invention provides a method for engineering bacteriophage to carry chimeric HRD proteins, so that the host specificity of the bacteriophage may be altered, for instance by one phage acquiring the host range of two or more bacteriophage upon acquisition of a single chimeric HRD protein carrying sequence from two or more heterologous HRD proteins. The method finds particular utility in creating, and selecting for, chimeric HRD proteins where regions of the HRD proteins are mixed, such that chimeric HRD proteins may be derived from two or more HRD sequences which have been split into two or more regions. The method is summarised schematically in FIG. 3.

There are known examples of engineered phage which have gained the host range of another closely related phage, by forming hybrid HRD proteins. However, these examples have failed to broaden the host range of bacteriophage, and allowed for only insignificant recombination events, and thus are of limited use. The examples involved the use of two phage sharing a conserved protein-protein interaction region (e.g. tail attachment region), usually in the N-terminal end of the protein, with a more divergent receptor binding region, usually in the C-terminal end of the protein. Hybrid phage HRD proteins are created by swapping the divergent receptor binding region from the two phage, utilising homologous recombination. As an example, Duplessis and Moineau (2001) selected for recombinant *Streptococcus thermophilus* DT1 phage which were provided with the putative HRD protein gene sequence from a related phage, MD4, as a substrate for recombination. The sequencing of the HRD protein genes from the recombinant phage showed that the recombination sites lay outside of a region encoding a variable region in the C-terminus of the protein. The recombinant phage inherited the host range of the donating MD4 phage, but had lost the host range of the parent DT1 phage.

In the known example described above, the reliance upon homologous recombination to generate sequence diversity in the HRD protein gene limits the number of possible variant sequences which could be produced. There are limitations on the site at which recombination can occur—sequence identity is required, and therefore the regions swapped must be flanked by sequence homologous to the target phage. The frequency of recombination varies according to the level of identity between two sequences (lower identity causing a lower frequency of recombination) and the length of homology (shorter regions of identity leading to a lower frequency of recombination), resulting in a range of recombination frequencies of $10^{-5}$ to $10^{-9}$ recombination events per viable cell in *E. coli* (Watt et al., 1985). Thus the exchange of sequences within the "variant" regions of an HRD protein are unlikely, due to the low sequence homology found in these sequences, so recombination generally happens between conserved regions of the proteins only. The likelihood of more than one region of the DNA sequence being replaced by homologous recombination is extremely low as the replacement of a single section of DNA by homologous recombination requires a minimum of two recombination events, whereas to replace an additional section of DNA would require another two recombination events, and thus four in total. Thus methods which rely solely upon recombination for generating chimeric HRD proteins, such as those described, are only likely to return recombinant phage carrying HRD proteins with a single region of variable sequence replaced by the corresponding region from a related HRD protein: there is little chance of genetic exchange, and hence chimera formation, within the DNA sequences encoding the variable regions of HRD proteins. The methods described in the art are likely to give rise to chimeric HRD proteins where a single section of heterologous sequence has been exchanged to create chimeras from a maximum of 2 donor HRD protein genes On the other hand, it has surprisingly been found that, using the method of the present invention, bacteriophage can be created which carry the host range of two or more bacteriophage, gaining the host range of the phage donating HRD sequences, thereby broadening or otherwise improving the host range.

The method of the present invention generates phage carrying genes encoding chimeric HRD proteins, where the variable region of the chimeric HRD protein consists of two or more variable region sequences from two or more phage. This method relies upon the use of a restriction enzyme that is capable of recognising a specific DNA sequence, i.e. its recognition sequence, and cleaving DNA at a specific cleavage site outside of the recognition sequence. The term "restriction enzyme" will be used hereafter in the present specification to mean a "restriction enzyme that is capable of recognising a specific DNA sequence, i.e. its recognition sequence, and cleaving DNA at a specific cleavage site outside of the recognition sequence". In an aspect, the restriction enzyme is a Type IIS or Type IIB restriction enzyme. Type IIS restriction enzymes cut the DNA at a specific location outside of its recognition site. Type IIB restriction enzymes cut the DNA at specific locations outside of and on both sides of its recognition site. The restriction enzyme is used in accordance with the present method to create libraries of HRD gene sequences, such that selected sections of the HRD gene sequences may be combined in an ordered manner, independently of DNA homology (sequence identity), from 2 or more HRD gene sequences, from 2 or more phage. The library of chimeric HRD gene sequences may be used to create a library of recombinant phage, and methods are provided to select recombinant phage possessing the combined host range conferred by the component HRD proteins. Homologous recombination occurs between the conserved sequences flanking the chimeric variable regions, and thus the generation of sequence variation in regions of the HRD gene encoding the variable protein sequences is dependent upon the random joining of fragments by ligation, rather than being dependent upon multiple recombination events. In an aspect, 2, 3, 4, 5, 6, 7, 8, 9, 10 or more DNA sequences are identified in step (1). The method is based upon a Golden Gate shuffling technique (Engler et al., 2009), which describes the shuffling of the DNA coding sequences of 3 different trypsinogens.

In an aspect, at least two DNA sequences may be identified by HRD nucleotide sequence alignment, HRD amino acid sequence alignment or HRD protein structure alignment. The method of the present invention finds particular utility in the creation of libraries from genes for HRD proteins with amino acid sequence homology; alternatively the method is particularly useful for the creation of chimeric analogous proteins, which are not necessarily homologous in DNA or protein sequence, but which may be aligned utilising structure-based alignment algorithms, where regions of conserved protein sequence or structure may be identified. Proteins may be aligned using programmes which make alignments based upon sequence similarity (e.g. BLAST, Needle (EMBOSS) or Clustal Omega) or based upon structural alignments (e.g. TM-Align). Providing the HRD protein sequences or structures can be aligned, DNA coding sequences for the proteins may be aligned without the requirement of DNA sequence homology. The aligned sequences may be split into 2 or more regions. In an aspect, the sequences are split into 2, 3, 4, 5, 6, 7, 8, 9, 10 or more regions. Such regions may be chosen according to sequence or structural characteristics. For instance, regions may be identified which are similar or dissimilar (according to protein sequence homology or structural similarity). Alternatively, regions of the protein may be chosen arbitrarily.

In an aspect, the restriction enzyme recognition sites may be added to each region. Each region may be flanked by a unique sequence, which may be a 3, 4 or 5 (or more) base pair (bp) sequence (depending on the particular restriction enzyme), which acts as the cut site for a restriction enzyme when such regions are cloned into a suitable plasmid vector.

In an aspect, the Type IIS restriction enzyme may selected from BsaI, BpiI, BcoDI, BbvI, BbsI, BsmAI, BsmFI, FokI, SfaNI, BfuAI, BsmBI, BspMI, BtgZI, Esp3I and isoschizomers of these enzymes. These are examples of Type IIS restriction enzymes which yield a 4 base overhang upon digestion. The Type IIS restriction enzyme may also be selected from EarI, BspQI, SapI, and isoschizomers of these enzymes. These are examples of Type IIS restriction enzyme which yield a 3 base overhang upon digestion. The Type IIS restriction enzyme may also be selected from HgaI. In an aspect, the Type IIB restriction enzyme may selected from AlfI, AloI, BaeI, BsgI, BplI, BsaXI, CspCI, FalI, PpiI, PsrI and isoschizomers of these enzymes. There are many other examples of Type IIB and Type IIS restriction enzymes which could be suitable for use in the method of the present invention. Such enzymes can be found listed on the websites of molecular biology reagent companies such as New England Biolabs or Thermo Scientific.

The use of restriction enzymes allows the cut site to be chosen within the HRD DNA sequence regions, as the recognition site can be added in sequences flanking these regions, upon cloning. Alternatively, the recognition sites can be added by incorporation into PCR primers, to make PCR products which carry restriction enzyme recognition and cleavage sites.

The sequences chosen to delineate the selected regions in the DNA sequences must consist of the 3, 4 or 5 base pair sequence which will form the cleavage site of the restriction enzyme. These 3, 4 or 5 bp cleavage site sites are equivalent to the sequences Engler et al. (2009) refer to as "recombination sites". Each 3, 4 or 5 base cleavage site must be unique for one end of each region.

In an aspect, the cleavage site sequence of at least one of the regions may be formed by changing the nucleotide base sequence of the region without changing the amino acid sequence encoded by the region. If one or more of the DNA sequences chosen does not contain an exact match to the selected 3 or 4 bp sequence, sequences may be altered without changing the coding sequence of the protein. This can be achieved by changing the base which corresponds to the "wobble" position of a 3 bp codon. The advantage of this aspect of the invention is that, together with the selection of an appropriate restriction enzyme, a restriction site may be incorporated almost at any desired position, without affecting the coding sequence of the protein.

In an aspect, the regions may be amplified or synthesised prior to incorporation into the vectors. Each region of a chosen coding sequence may be amplified by PCR or synthesised, so that restriction sites are engineered into the regions thus:

Recognition_site/
Cleavage_site_UHRD_REGION\Cleavage_site_2\Recognition_site

In an aspect, the amplified or synthesised sequences of each region may be cloned into a plasmid vector. Alternatively, after the recognition sites and cleavage sites are engineered into the regions as described above, for instance by way of PCR primers to provide a PCR product, sequences of each region need not be cloned into a plasmid. In this aspect the sequences of each region may be digested by the restriction enzyme as described below. In this respect, the DNA sequence comprising the recognition sites and cleavage sites and the region, such as the PCR product, may be understood to fall within the meaning of the term "vector" as defined in steps (2) and (3).

Thus a library of HRD sequences may be created, each library carrying the DNA coding sequences from 2 or more regions of each HRD protein, of which there may be 2 or more. For instance, an HRD protein could be split into 6 regions based upon sequence homology or structural similarity to other HRD proteins. In this example the 6 regions could be designated regions A, B, C, D, E and F, ordered, in this example, from the 5' to 3' coding sequence of the gene. Phage which provide HRD sequences for construction of DNA fragment libraries are designated "donor" phage. In this example, a library from donor phage 1 may be created, where the DNA fragments may be designated 1A, 1B, 1C, 1D, 1E and 1F. For the HRD protein of donor phage 2, a library of fragments may be created designated 2A, 2B, 2C, 2D, 2E and 2F. Phage 1 and 2 may have different host ranges. These DNA sequence may be cloned into plasmid vectors, such that the recognition sites for the restriction enzymes are located outside the coding sequence of the gene fragments (FIG. 4A). Alternatively, these DNA sequences of the gene fragments need not be cloned into a plasmid vector. Each fragment may be flanked by the recognition site for the same restriction enzyme, and the cleavage site would be different for each fragment, but designed such that fragments could only ligate together in an ordered manner. For instance DNA C would be flanked by a cleavage site which would only allow ligation of DNA fragment B at the 5' end and D at the 3' end. This is guaranteed by selection of a unique 3 or 4 base sequence (corresponding to a recognition sequence for a particular restriction enzyme) at the end of each region. Thus the fragments would always ligate together in order A-B-C-D-E-F, without the addition of restriction recognition site sequences to the coding sequence of the fragments. Therefore, plasmid clones carrying chimeras of the two HRD sequences would be formed, e.g. 1 A2B1C2D1E2F, by ligating the fragments into a delivery vector, in between sequences which flank the HRD protein DNA sequence from the target phage (FIG. 4B).

In an aspect, the method may further comprise step (5) of incorporating each hybrid HRD from the array of hybrid HRDs into a delivery vector to form an array of delivery vectors.

In an aspect, steps (3) and (4) may be carried out in a single reaction. In another aspect, where the method further comprises step (5), steps (3), (4) and (5) may be carried out in a single reaction. This may involve adding both the restriction enzyme and ligase, and if appropriate, the delivery vector, together with a mixture of the vectors from step (2) at the same time to allow both the restriction and ligation to occur in a single reaction. In other words, the mixture of regions generated in step (3), and if appropriate, the delivery vector, may be treated with the ligase without isolating or separating the restriction enzyme from the mixture. This is advantageous, since it provides for a simplified process. Further, the lack of a separation step ensures the mixture retains all the regions produced by step (3) that may otherwise be lost or reduced during a separation step after step (3). Thus the donor plasmids are cut by the restriction enzyme, and the chimeras formed by ligation. The ligated chimeras cannot be re-cut by the restriction enzyme because the ligated sequence no longer contains the recognition site.

In an aspect, the method of the present invention may further comprise the following steps: (a) the array of delivery vectors is contacted with first host cells so as to introduce each delivery vector into a first host cell to form an array of transformed first host cells; (b) the array of transferred first host cells is infected with a target phage; (c) phage replication and recombination are effected; (d) recombinant phage are screened; and (e) recombinant phage bearing hybrid HRDs are selected.

A library of such plasmids may be constructed as described above. The number of different HRD protein chimeras that could be created can be calculated from the number of HRD protein gene sequences (H) to the power of the number of regions, or fragments (F), i.e. $H^F$. The library of plasmids may be transferred into a bacterial host for the target phage, by standard methods such as electroporation or conjugation. The target phage may be one of the donor phage which provides HRD DNA sequence, from an identified varied region of an HRD protein, to form one component of the plasmid library. Thus, in an aspect, the target phage may comprise one of the at least two DNA sequences that encode an HRD. Alternatively, the target phage might not be a donor phage, instead only DNA sequences for HRD proteins which are homologous or analogous to the HRD protein for the target phage may be provided in the DNA fragment libraries. The host cell library may be infected by the target phage and a lysate obtained. Some of the phage in the lysate may be recombinant phage, which have acquired the chimeric HRD sequences from the plasmid library by recombination.

In an aspect, the steps (d) and (e) may comprise propagating recombinant phage on a second host cell which is a host for phage bearing a hybrid HRD and not a host for the target phage. Useful recombinant phage may be selected by screening for the formation of plaques, when the lysate is mixed with a strain or strains which are the host for one or more of the donor phage which have contributed HRD sequences to the DNA fragment libraries, but are not the normal host for the target phage. This step usefully selects against phage which have not acquired the chimeric HRD sequences from the plasmid library by recombination. In an aspect, the method of the present invention may further comprise the steps: (f) the selected recombinant phage bearing hybrid HRDs are contacted with the first host cells so as to infect the first host cells; (g) phage replication is effected; and (h) recombinant phage bearing hybrid HRDs capable of infecting the first host cell and the second host cell are selected.

In an aspect of the present invention, step (e) may comprise selecting a recombinant phage bearing hybrid HRDs which confer a host range which is broader than a host range of the target phage. In another aspect of the present invention, step (e) may comprise selecting a recombinant phage bearing hybrid HRDs which confer a host range comprising host ranges of the HRD sequences encoded by the at least two DNA sequences. In this aspect, the overall host range conferred by the hybrid HRDs may not necessarily be broader than the combined host ranges of the original HRD sequences encoded by the at least two DNA sequences, or that of the target phage. Nonetheless, it will be appreciated that this aspect is still advantageous, particularly if the overall host range covers a plurality of target bacteria which are particularly pathogenic, resistant to antibiotics, or otherwise difficult to treat, etc. In the above examples the recombinant phage may be screened on the host for Phage 1, which is not a host for Phage 2, and the host for Phage 2 which is not the host for Phage 1. The recombinant phage may be screened sequentially, by plaquing on one host, isolating phage from plaques formed on that host, and then screening these plaques on the second host. Alternatively, the recombinant phage could be screened by plaquing against the two hosts simultaneously, identifying clear plaques where the phage has been able to infect both host strains. By isolating plaques in such screens, phage can be obtained which carry chimeric HRD protein genes which convey an altered host range to the target phage, such that the chimeric HRD proteins confer the host range of both of the component HRD proteins to the chimeric HRD proteins selected. The phage HRD protein genes from the isolated phage may be PCR amplified and sequenced. Thus regions of the HRD proteins which confer a particular host range may be identified.

The above technique can be performed with more than two phage HRD sequences. For instance a library of HRD regions from 3 phage HRD proteins may be created. The desired recombinant phage may be recovered by screening against 3 host strains, where each host strain is a host for only one of the 3 phage and not the other 2. In this way, chimeric HRD proteins may be selected which are able to infect all 3 strains. Similarly 4, or more, HRD protein sequences may be selected and the technique applied.

An alternative approach would be to re-create active phage particles using an in vitro packaging system (Rosenberg et al., 1985), in combination with the DNA fragments from the plasmid library of HRD sequences, to transfect a suitable host strain to propagate the reconstituted phage. Such phage may be host range tested, in order to isolate phage with the desired characteristics, as described herein.

Another approach would be to use the DNA fragments from the library, together with the rest of the genome sequence from the target phage, to create cell-free transcription-translation system to create engineered phage particles in vitro (Shin et al., 2012). Such phage may be host range tested, in order to isolate phage with the desired characteristics, as described herein.

A further approach would be to use the DNA fragments in the plasmid library, together with the phage genome DNA, and transfecting a suitable host, to construct viable phage using a recombineering approach, such as Bacteriophage Recombineering of Electroporated DNA (BRED) (Marinelli et al., 2008). Such phage may be host range tested, in order to isolate phage with the desired characteristics, as described herein.

In a further aspect of the invention, step (e) may comprise selecting a recombinant phage bearing hybrid HRDs having a broad host range as defined by more than 50% of a collection of at least 35 and preferably more than 50 clinical isolates, from a plurality of different infection sites and including range of antibiotic resistance phenotypes.

According to the present invention it is preferred to select a recombinant phage bearing hybrid HRDs on the basis of a broadened host range. A broad host range may be defined as the ability to infect >50% of a diverse collection or clinical isolates, of at least 35 and preferably totalling >50 in number. Such isolates should be from a range of geographical locations, including Europe, the Americas, and Asia, should carry a diverse range of antibiotic resistance phenotypes, including multi-drug resistant (MDR) strains, and should be from a diverse range of infection sites, such as strains cultured from blood, lung and skin infections. Such isolates can be obtained from public strain collections such as the American Type Culture Collection (ATCC) and the National Collection of Type Cultures (NCTC).

According to the present invention, 2 or more phage are required to provide divergent HRD protein sequences. Suitable phage may be isolated by screening for phage capable of infecting a single chosen bacterial species. In this way several phage may be isolated which infect different isolates of that species. For instance, Gram negative bacteria show high degree of variation in their cell surface, where the binding receptors for phage commonly reside (Wang et al., 2010; Rakhuba et al., 2010). Bacterial strains may also be typed by the anti-sera that can be raised against their cell surface antigens, so-called serotyping (Faure et al., 2003; Lu et al., 2014). For instance, in *P. aeruginosa*, there are 20 serotypes (Faure et al., 2003; Lu et al., 2014). In *K. pneumoniae* the polysaccharide surface capsule in the major source of surface variation and an important virulence factor, and 78 capsule types have been found by molecular typing methods (Pan et al., 2013). If the use of a modified bacteriophage is as a medicine, it is advantageous for that modified bacteriophage be able to bind and infect as many different isolates of that species as possible, to address the spectrum of activity of such a modified phage for the treatment of bacterial infections. Thus, the use of HRD proteins from several phage which infect the same bacterial species, where the cumulative host range of these bacteriophage is greater than any single component bacteriophage, is advantageous.

Alternatively, this technique may be applied to create bacteriophage may be isolated which are able to infect more than one bacterial species. For instance a bacteriophage may be isolated which infects one species, and another bacteriophage may be isolated which infects another. Their host range may be mutually-exclusive. Such bacteriophage could provide HRD protein sequence which could be used, in the way described, to create modified bacteriophage to be used as medicines, where the modified bacteriophage are able to target 2 or more bacterial species, providing a broad spectrum anti-bacterial agent.

In the former case, where phage are required to target a single bacterial species, phage may be isolated by screening samples for infectivity against the chosen species. For instance, phage may be isolated which infect *Pseudomonas aeruginosa*, by screening for phage from environmental sources which are able to form plaques on representative *P. aeruginosa* strains (Gill and Hyman, 2010). Isolated phage may have their whole genomes sequenced and annotated.

The approach described in the present invention is particularly advantageous as compared to the previous approaches to broaden or improve the host range of a bacteriophage composition, such as the "cocktail" approach described previously. The present invention is useful in improving phage compositions such as the SASPject system, which is described in greater detail below. In particular, the present invention may be used to broaden the host range of a SASPject vector. A single SASPject vector could replace the need to use two or more SASPject vectors, if the host range of multiple SASPject vectors were combined and thereby broadened using the methods of the present invention. One advantage is that there would be fewer component phage to manufacture (i.e. if the host range of a single phage produced in accordance with the invention were broadened, compared to the case where the desired host range is conferred by two or more phage in a mixture). This is an important aspect of a pharmaceutical preparation: the costs of manufacture will be reduced. Further, in accordance with the invention, fewer phages, possibly just one phage, will be required to provide the equivalent breadth in host range provided by the "cocktail" approach described previously, thus reducing the complexity of a pharmaceutical preparation.

In an aspect, the HRDs may comprise tail fibre proteins. Each tail fibre protein may comprise a receptor binding region for binding to the target bacteria and a region linking the receptor binding region to the body of the bacteriophage. The receptor binding region may be a C-terminal receptor binding region and the region linking the C-terminal receptor binding region to the body of the bacteriophage may be an N-terminal region. The N-terminal region may comprise amino acids 1 to 628 of the tail fibre protein and the C-terminal region may comprise amino acids 629 to 964 of the tail fibre protein, based on the amino acid sequence of bacteriophage Phi33.

Tail fibre proteins are commonly found to be proteins responsible for the initial recognition/binding to the host bacterium, for instance in phage T4, T5 and T7 (Rakhuba et al., 2010). Alternatively other HRD may be baseplate proteins. Phage genomes may be searched for potential HRD sequences by assessing the homology of all proteins in the phage genome to known sequences, using BLAST searches.

It is advantageous to identify phage tail fibre proteins which share sequence identity of greater than 90% in the N-terminal region. For example several phage—Phi33, PTP47, PTP92 and C36—with a broad host range for *P. aeruginosa* strains (each of these phage infect >60%, when analysed against 260 strains), have been isolated/identified and their genomes sequenced. Analysis of the genome sequences of Phi33, PTP47, PTP92 and C36 reveals that they contain genes encoding putative tail fibre proteins with a high level of sequence identity in the N-terminal region (>95% amino acid sequence identity), following a 2 sequence BLAST alignment, compared to the Phi33 tail fibre amino acids 1-628 (amino acid identity in parentheses): C36 (96%), PTP47 (98%), PTP92 (97%). BLAST searches have shown that these 4 phages are related to 10 other deposited phage genome sequences which, together, form the family of PB1-like phage: PB1, SPM1, F8, LBL3, KPP12, LMA2, SN, JG024, NH-4, 14-1 (Ceyssens et al., 2009). The homology of these putative tail fibre proteins was assessed. Following a 2 sequence BLAST alignment, compared to the Phi33 tail fibre protein (amino acid identity in parentheses): LBL3 (96%), SPM-1 (95%), F8 (95%), PB1 (95%), KPP12 (94%), LMA2 (94%), SN (87%), 14-1 (86%), JG024 (83%), NH-4 (83%), C36 (96%), PTP47 (86%), PTP92 (83%). An alignment of all 14 of the aforementioned phage tail fibre proteins is shown in FIGS. 5A-5E.

Analysis of the annotated tail fibre protein sequences from these 14 phages reveals that the N-terminal region of the proteins—equivalent to Phi33 tail fibre amino acids 1-628—show an even higher level of sequence identity at the amino acid level than the sequence identity of these proteins over their entire length, in the range of 96-100% for all 14 proteins. Following a 2 sequence BLAST alignment, compared to the N-terminal amino acids 1-628 of the Phi33 tail fibre protein (amino acid identity in parentheses): LBL3 (96%), SPM-1 (96%), F8 (96%), PB1 (96%), KPP12 (98%), LMA2 (99%), SN (99%), 14-1 (97%), JG024 (97%), NH-4 (97%), PTP47 (98%), C36 (96%), PTP92 (97%). However, the C-terminal region of the protein—equivalent to Phi33 tail fibre amino acids 629-964—is not as conserved as the N-terminal region in some of the proteins, the range of sequence identity being typically 57-96%. Following a 2 sequence BLAST alignment, compared to the C-terminal 629-964 amino acids of the Phi33 tail fibre protein (amino acid identity in parentheses): LBL3 (94%), SPM-1 (93%), F8 (93%), PB1 (94%), KPP12 (87%), LMA2 (85%), SN (65%), 14-1 (65%), JG024 (57%), NH-4 (57%), PTP47 (64%), C36 (96%), PTP92 (57%). Analysis of phage tail fibres from other, well characterised, phage has shown that they possess an N-terminal tail base plate binding region and a C-terminal receptor binding region (Veesler and Cambillau, 2011). In experimental analysis of their bacterial strain host range, using plaque assay or growth inhibition tests, the phage Phi33, PTP47, PTP92 and C36 have overlapping but non-identical host range (FIG. 1). Taken together with the established evidence for the role of the C-terminal region of phage tail fibres being involved in bacterial host receptor binding, and the sequence variation in the C-terminal region of these 4 phage, and their similar but non-identical host range, it is postulated that the C-terminal variation is associated with host range in the phage assessed.

It is thus provided, according to this invention, that the genes for homologous tail fibre proteins can be taken from two or more of these exemplified phage and combined, via the methods described, to form chimeric tail fibre proteins, in particular where the C-terminal variable region of the chimeric tail fibre proteins contains sequences from two or more of these phage in a mixed fashion. In such a way, the C-terminal region of such tail fibre proteins may be delineated into 2 or more regions, and these regions may be fused together in an ordered fashion, to create variation in the C-terminal region of the protein, and allow selection of variants for improved host range.

The method of the present invention was used to select recombinant tail fibre proteins which conferred improved host range to a homologous target phage. The tail fibre DNA and protein sequences from phage PTP92 and PTP47 were aligned (FIGS. 6A-6D and 7A-7B). The DNA sequence for the C-terminal amino acids 629-964 from phage PTP92 and PTP47 was used to create a library of six regions for each phage using the methods described herein. The unique cleavage sites, which delineate each of the six regions, are shown in FIGS. 7A and 7B. A library of chimeric tail fibre proteins was created in *E. coli*, such that the chimeric sequences were flanked by regions homologous to the sequences flanking the DNA sequence encoding amino acids 629-964 of the Phi33 tail fibre protein. The library was transferred to *P. aeruginosa*, and these cells were infected with phage Phi33 and recombinant phage were isolated, by selecting phage which were able to plaque on a host exclusive for PTP92 (but not Phi33 or PTP47) and a host exclusive for PTP47 (but not Phi33 or PTP92). Host range testing of the recombinant phage identified one phage isolate, PTP238, which was able to plaque on strains infected by either PTP92 or PTP47 (FIG. 1). In this way PTP238, had acquired the host range of both PTP92 and PTP47, when assessed on the strains tested, and its host range was improved, compared to the target phage, Phi33. Sequence analysis showed that PTP238 carried a chimeric tail fibre protein with 2 sequence regions from the C-terminal sequence regions of the PTP47 tail fibre protein and 4 sequence regions from the C-terminal sequence regions of the PTP92 tail fibre protein (FIG. 6).

In an aspect, the recombinant phage bearing hybrid HRDs produced in accordance with the present invention are provided with a gene encoding a protein which is toxic to a target bacterium. Such a gene may encode an α/β-type small acid-soluble spore protein (SASP). The SASP is preferably a SASP-C. The SASP-C may be from *Bacillus megaterium*.

As an alternative to conventional antibiotics, one family of proteins which demonstrate broad spectrum antibacterial activity inside bacteria comprises the α/β-type small acid-soluble spore proteins (known as SASP). Inside bacteria, SASP bind to the bacterial DNA: visualisation of this process, using cryoelectron microscopy, has shown that SspC, the most studied SASP, coats the DNA and forms protruding domains and modifies the DNA structure (Francesconi et al., 1988; Frenkiel-Krispin et al., 2004) from B-like (pitch 3.4 nm) towards A-like (3.18 nm; A-like DNA has a pitch of 2.8 nm). The protruding SspC motifs interact with adjacent DNA-SspC filaments packing the filaments into a tight assembly of nucleo-protein helices. In 2008, Lee et al. reported the crystal structure at 2.1 Å resolution of an α/β-type SASP bound to a 10-bp DNA duplex. In the complex, the α/β-type SASP adopt a helix-turn-helix motif, interact with DNA through minor groove contacts, bind to approximately 6 bp of DNA as a dimer and the DNA is in an A-B type conformation. In this way DNA replication is halted and, where bound, SASP prevent DNA transcription. SASP bind to DNA in a non-sequence specific manner (Nicholson et al., 1990) so that mutations in the bacterial DNA do not affect the binding of SASP. Sequences of α/ß-type SASP may be found in appendix 1 of WO02/40678, including SASP-C from *Bacillus megaterium* which is the preferred a/B-type SASP. WO02/40678 describes the use as an antimicrobial agent of bacteriophage modified to incorporate a SASP gene.

Bacteriophage vectors modified to contain a SASP gene have generally been named SASPject vectors. Once the SASP gene has been delivered to a target bacterium, SASP is produced inside those bacteria where it binds to bacterial DNA and changes the conformation of the DNA from B-like towards A-like. Production of sufficient SASP inside target bacterial cells causes a drop in viability of affected cells.

In particularly preferred embodiments, the method of the present invention may be used to engineer improved SASPject vectors carrying chimeric tail fibre genes, created and selected by this method, together with a SASP gene under the control of a selected promoter. Such SASPject vectors would have improved host range in comparison to the wild-type, unmodified, bacteriophage upon which they are based.

The SASP gene may be chosen from any one of the genes encoding the SASP disclosed in Appendix 1 of WO02/40678. In a preferred arrangement the SASP is SASP-C. The SASP-C may be from *Bacillus megaterium*.

In one aspect, the term 'SASP' as used in the present specification refers to a protein with α/β-type SASP activity, that is, the ability to bind to DNA and modify its structure from its B-like form towards its A-like form, and not only covers the proteins listed in appendix 1 of WO02/40678, but also any homologues thereof, as well as any other protein also having α/β-type SASP activity. In an alternative aspect, the term 'SASP' as used in the specification refers to any protein listed in appendix 1 of WO02/40678, or any homologue having at least 70%, 75%, 80%, 85%, 90%, 92%, 94%, 95%, 96%, 98% or 99% sequence identity with any one of the proteins listed in appendix 1 of WO02/40678. In another alternative aspect, the term 'SASP' as used in the specification refers to any protein listed in appendix 1 of WO02/40678.

It is preferred that the SASP gene is under the control of a constitutive promoter which is advantageously sufficiently strong to drive production of toxic levels of SASP when the modified bacteriophage is present in multiple copies in the target bacterium. Useful constitutive promoters include pdhA for pyruvate dehydrogenase E1 component alpha sub units, rpsB for the 30S ribosomal protein S2, pgi for glucose-6-phosphate isomerase and the fructose bisphosphate aldolase gene promoter fda/fba. Preferred regulated promoters, active during infection, are lasB for elastase. These promoters are typically from *P. aeruginosa*. Promoters having a sequence showing at least 90% sequence identity to these promoter sequences may also be used.

BRIEF DESCRIPTION OF THE SEVERAL VIEWS OF THE DRAWINGS

FIG. 1. Infectivity of phage PTP238, Phi33, PTP47 and PTP92. Infectivity assessed by inoculating phage on to agar seeded with *P. aeruginosa* bacteria (strains listed in figure), and assessing the growth of the bacterial lawn in the region of the inoculum. Growth inhibition is marked +, indicating that the phage infects the host strain. Strains which are not infected by the phage are marked.

FIGS. 2A-2B. Summary of HRD modules 1A-1F and 2A-2F. The sequences of the cleavage sites (cs) and their abbreviations are shown, along with the sequences of the module fragments that could be generated by synthesis, and the plasmids that could be constructed by cloning these fragments into a derivative of pUC57 from which the native BsaI restriction site has been silently removed.

Figure 3:
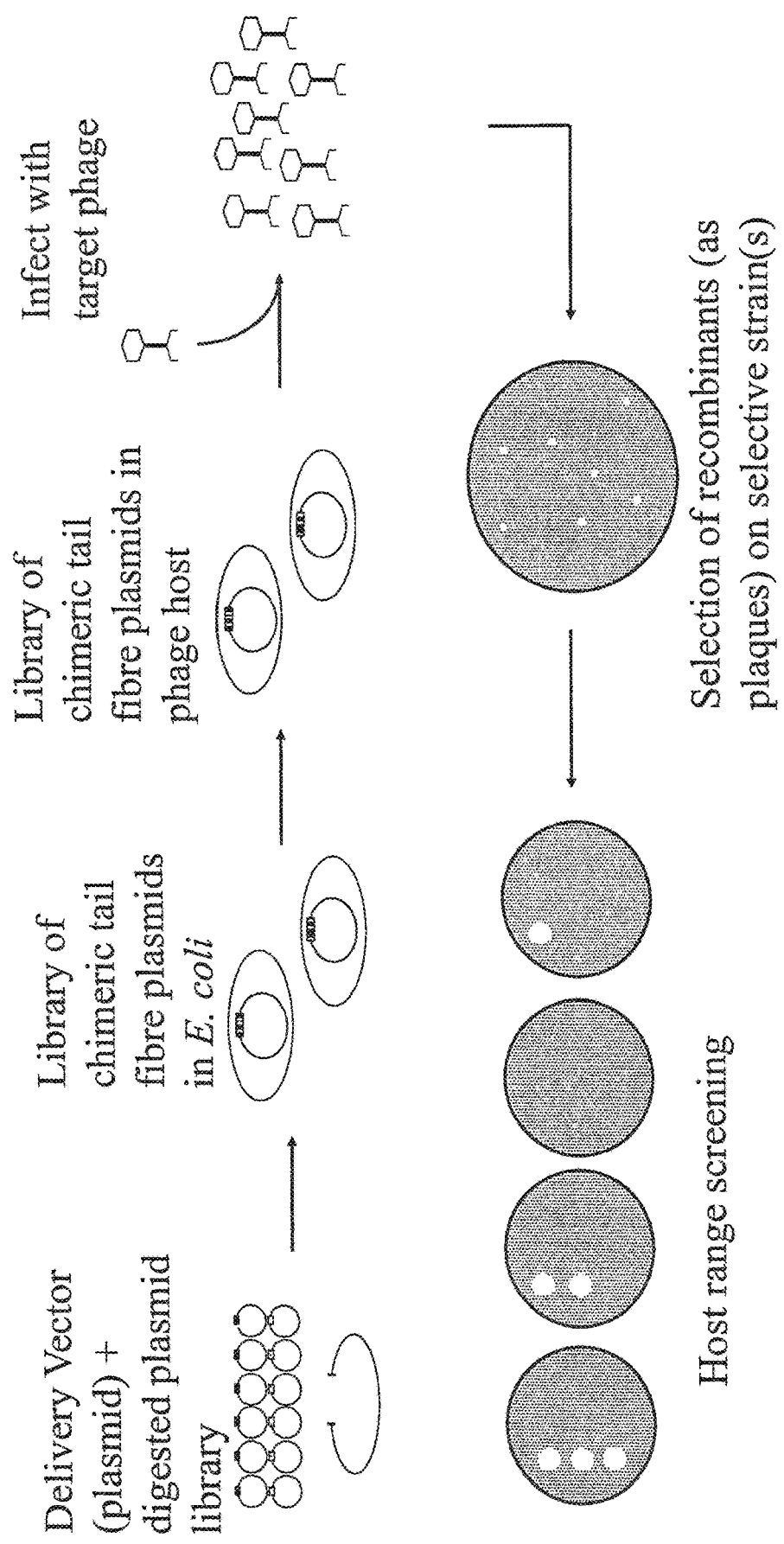
FIG. 3. Schematic summarising the method for creating recombinant bacteriophage carrying chimeric HRD protein, following construction of a chimeric HRD library.
Figure 4A:
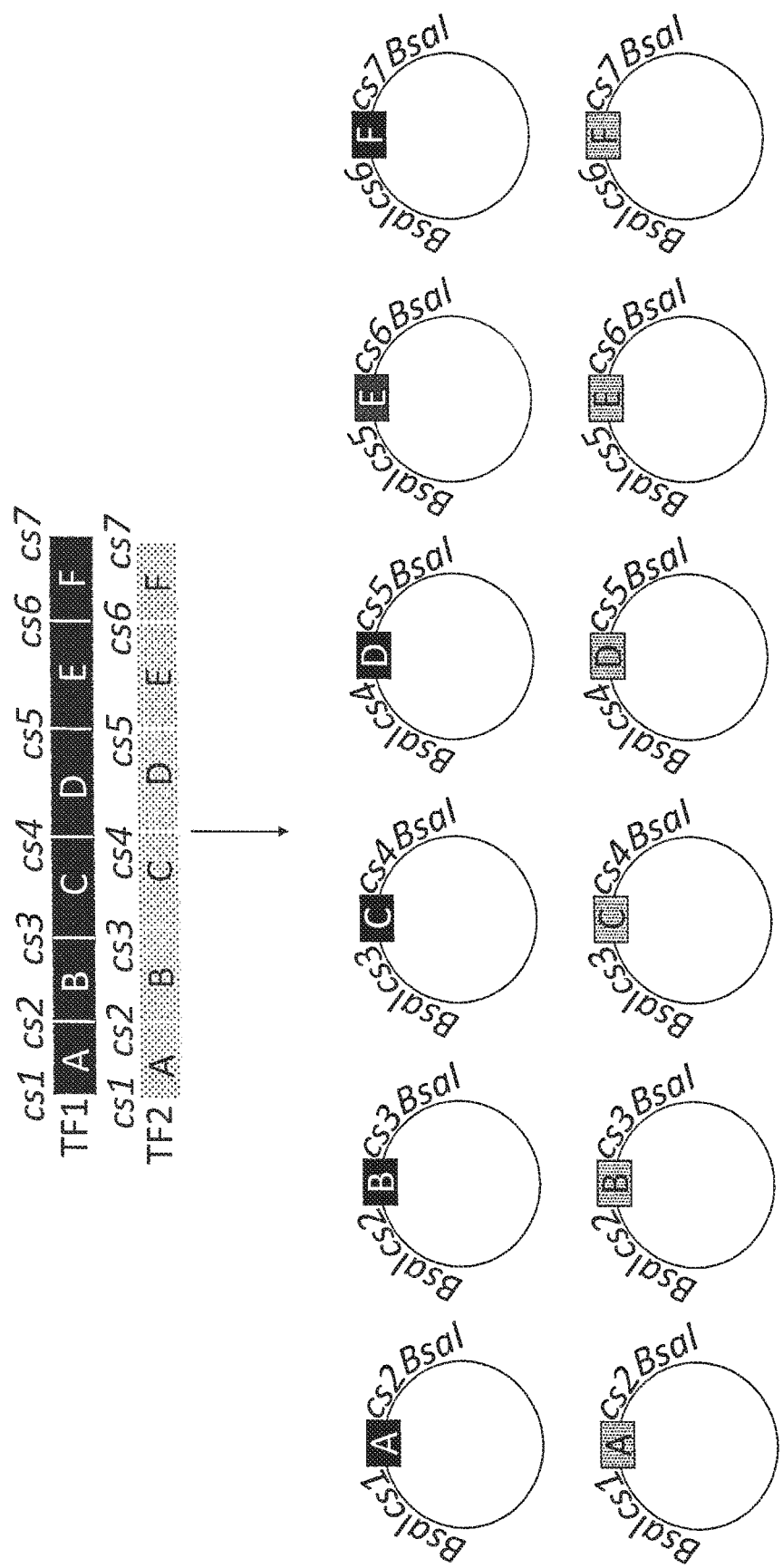
FIGS. 4A-4B. Schematic summary of the method of the present invention for the creation of a phage carrying in chimeric HRD proteins. (A) For each phage, set of six plasmids are created to contain the coding sequence for six regions (labelled A-F) of the phage's HRD protein (HRD1 and 2). Each region is delineated by a cleavage site (labelled cs1-7): specific for the junction (or termini) of each region. When cloned in the plasmid: the cleavage sites are flanked by recognition sites for a Type IIS restriction enzyme (BsaI in this instance). For the example shown there are two phage HRD sequences, HRD1 and HRD2 from phage 1 and 2 respectively, and thus 12 plasmids created in total. (B) The 12 plasmids, together with a plasmid delivery vector, are digested with a BsaI and ligated together in a one-pot reaction to form plasmids which carry the coding sequence for chimeric HRD proteins which are randomly mixed in the six regions A-F, flanked homology arms (HA) for recombination with the target have. A delivery vector carrying a mixture of DNA sequences is shown as an example.

FIGS. 5A-5E. CLUSTAL Omega multiple sequence alignment of the tail fibre proteins from Phage SPM-l, F8, PBl, C36, LBL3, Phi33, LMA2, KPP12, JG024, PTP92, NH-4, 14-1, PTP47, SN. Sequence divergent C-terminal region shaded in grey, sequence conserved N-terminal region unshaded.sss FIGS. 6A-6D. Needle (EMBOSS) pairwise alignment of the tail fibre genes from Phage PTP92 and PTP47. The sequences used as cleavage sites, when cloned into plasmid vectors with flanking restriction enzyme recognition sites, are shaded in black. Nucleotides shown in bold and underlined are changed to corresponding nucleotide sequence in the second aligned sequence upon synthesis and cloning. The translated protein sequence is preserved upon nucleotide sequence change.

FIGS. 7A-7B. CLUSTAL Omega multiple sequence alignment of the tail fibre proteins from Phage PTP92 and PTP47. The residues which correspond to the boundaries of the DNA sequence regions cloned in the plasmid libraries are shown shaded in black.

FIG. 8. Sequence of the tail fibre protein from PTP238. Sequences PTP92 are shown in bold and sequences from PTP47 are underlined. The remainder of the sequences is from Phi33, The boundaries of the sequence regions are marked by residues which are shaded black.

FIGS. 9A-9C. A schematic diagram showing one way of isolating recombinant bacteriophage that have acquired the host range of two or more donor bacteriophage.

DETAILED DESCRIPTION OF INVENTION

Summary of a method for the genetic modification of a bacteriophage such that it carries chimeric tail fibre variants that confer a desired altered host range.

As an example only, it is shown here how the amino acid sequences of phage host range determinants, such as those from PTP92 and PTP47 may be aligned, and how the regions of conservation and variation thus identified may be used to divide one of the HRD-encoding genes (such as that from PTP92) into several modules. The sequence alignment can then be used to divide any other HRD-encoding genes under consideration (in this example, PTP47) into positionally-corresponding modules.
Figure 4B:
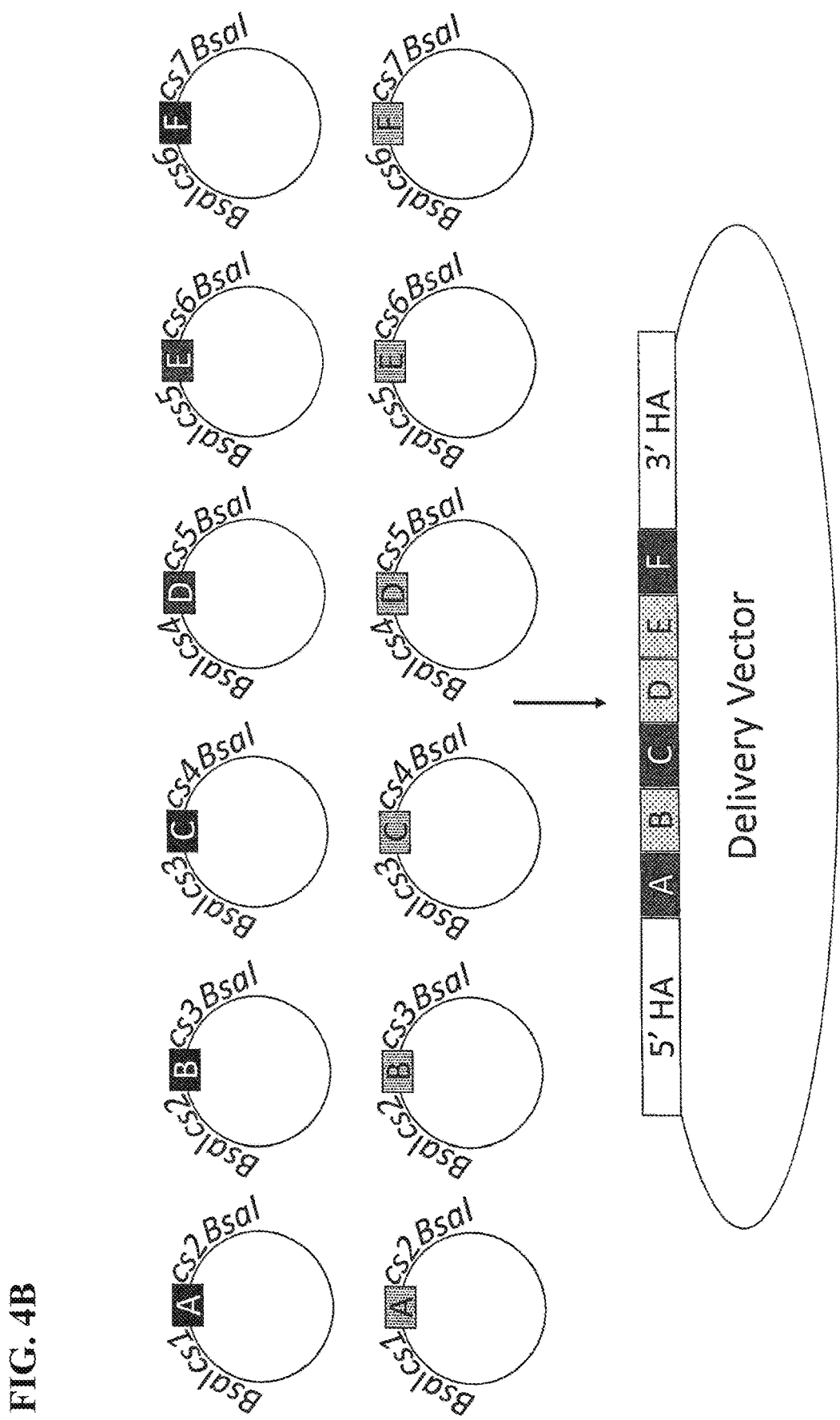

It is shown how the HRD modules thus defined from PTP92 and PTP47 may each be flanked by TypeIIS (BsaI) restriction sites and suitable cleavage sites (cs). It is then shown how a plasmid library consisting of every possible combination of PTP92 and PTP47 HRD modules may be constructed by Golden Gate assembly, to form a plasmid library of chimeric HRDs.

There are several ways in which phages carrying non-native genetic DNA sequences can be constructed and the following is an example of such methods. One way in which genes can be removed and added to the phage genome is by using homologous recombination. Here, it is shown, as an example, how the chimeric HRDs can be cloned in between a Phi33 sequence located immediately upstream of the corresponding identified variable region of the Phi33 HRD, and another Phi33 sequence located immediately downstream of the corresponding Phi33 HRD. These Phi33 sequences can act as regions of homology for homologous recombination with Phi33 bacteriophage. The resulting plasmid library of chimeric HRDs cloned in between Phi33 regions of homology can then be transferred to a *P. aeruginosa* strain that is a host for Phi33, PTP92 and PTP47.

To isolate Phi33 derivatives which have undergone recombination with the chimeric HRDs library, a Phi33 lysate may be made on a mixed culture of *P. aeruginosa*, each cell of which carries a representative of the chimeric HRDs library, and where each representative of the chimeric HRDs library is present in the mixed culture. The resulting lysate may then be propagated on a *P. aeruginosa* strain that is a host for PTP92, but not Phi33 or PTP47, to isolate recombinant phage that have acquired the plaquing ability of PTP92. A second round of phage propagation may be carried on the same PTP92 host *P. aeruginosa* strain to enrich the resulting lysate for the desired recombinant phage that have acquired the plaquing ability of PTP92. This second lysate may then be plagued on a *P. aeruginosa* strain that is a host for PTP47, but not Phi33 or PTP47, as a means of isolating recombinant phage that have acquired the plaquing ability of PTP47. After plaque purification on the same PTP47 host *P. aeruginosa* strain, individual plaques may then be tested for plaquing on the *P. aeruginosa* strain that is a host for PTP92, but not PTP47 or Phi33. Phages that plaque on both the PTP47 discriminatory host and the PTP92 discriminatory host have acquired the host range of both PTP47 and PTP92, and are likely to carry genes encoding chimeric HRD proteins. The HRD region from phage thus identified may be amplified by PCR and sequenced, or alternatively genomic DNA from the phage may be isolated and submitted to whole genome sequencing, to identify the sequence of the chimeric HRD that confers the desired dual host range of PTP92 and PTP47 upon the recombinant Phi33 derivatives.

Experimental Procedures

PCR reactions to generate DNA for cloning purposes may be carried out using Herculase II Fusion DNA polymerase (Agilent Technologies), depending upon the melting temperatures ($T_m$) of the primers, according to manufacturer's instructions. Alternatively, DNA for cloning may be obtained via custom DNA synthesis, for example by GenScript or DNA 2.0. PCR reactions for screening purposes may be carried out using Taq DNA polymerase (NEB), depending upon the $T_m$ of the primers, according to manufacturer's instructions. Unless otherwise stated, general molecular biology techniques, such as restriction enzyme digestion, agarose gel electrophoresis, T4 DNA ligase-dependent ligations, competent cell preparation and transformation may be based upon methods described in Sambrook et al., (1989). Enzymes may be purchased from New England Biolabs or Thermo Scientific. DNA may be purified from enzyme reactions and prepared from cells using Qiagen DNA purification kits. Plasmids may be transferred from *E. coli* strains to *P. aeruginosa* strains by conjugation, mediated by the conjugation helper strain *E. coli* HB101 (pRK2013). A chromogenic substrate for β-galactosidase, S-gal, that upon digestion by β-galactosidase forms a black precipitate when chelated with ferric iron, may be purchased from Sigma (S9811).

Primers may be obtained from Sigma Life Science. Where primers include recognition sequences for restriction enzymes, additional 2-6 nucleotides may be added at the 5' end to ensure digestion of the PCR-amplified DNA.

Standard clonings may be achieved by ligating DNAs overnight with T4 DNA ligase and then transforming them into *E. coli* cloning strains, such as DH5a or TOP10, with isolation on selective medium, as described elsewhere (Sambrook et al., 1989). Clonings involving TypeIIS restriction enzymes may be achieved by incubating the DNAs simultaneously with T4 DNA ligase and with the relevant TypeIIS restriction enzyme, in T4 DNA ligase buffer, using a thermal cycler programmed as follows:

| Temperature | Time | Number of cycles |
|---|---|---|
| 37° C. | 2 hours | 1 |
| 37° C. | 2 minutes | 50 |
| 16° C. | 3 minutes | |
| 50° C. | 5 minutes | 1 |
| 80° C. | 5 minutes | 1 |
| 16° C. | Hold | 1 |

An *E. coli/P. aeruginosa* broad host range vector, such as pSM1484A, may be used to transfer genetic material between *E. coli* and *P. aeruginosa*. This type of vector is otherwise known as a delivery vector. Plasmid pSM1484A is a previously engineered construct carrying a broad-host-range, low copy origin of replication from a *P. aeruginosa* plasmid, an *E. coli*-specific high-copy origin of replication from plasmid pUC19, the oriT origin of transfer from plasmid RP4, a tetracycline resistance marker, and sequence modified from phage Phi33. The latter sequence comprises the conserved region of Phi33's HRD, silently mutated to suppress an intrinsic BsaI site, followed by a CTCGtGAGACC (SEQ ID NO: 1) BsaI site containing cs1 (CTCG), a lacZa reporter gene, a second BsaI site GGTCTCaAATG (SEQ ID NO: 2) containing cs7 (AATG), and finally sequence from Phi33 corresponding to sequence downstream of the HRD gene's stop codon in the native genome.

Detection of Phi33-like phage (PB1-like phage family) conserved N-terminal tail fibre regions by PCR 1. Primers for the detection of Phi33-like phage-like tail fibre genes in experimental phage samples may be designed as follows:

The DNA sequences of the tail fibre genes from all sequenced Phi33-like phage (including Phi33, PB1, NH-4, 14-1, LMA2, KPP12, JG024, F8, SPM-1, LBL3, PTP47, C36, PTP92 and SN) may be aligned using Clustal Omega, which is available on the EBI website, and the approximately 2 kb-long highly conserved region mapping to the gene's 5' sequence may be thus identified (positions 31680-33557 in the PB1 genome sequence, Acc. EU716414). Sections of 100% identity among the 11 tail fibre gene sequences may be identified by visual inspection. Three pairs of PCR primers targeting selected absolutely conserved regions, and amplifying PCR products no longer than 1 kb may be chosen as follows: pair B4500 and B4501, defining a 193 bp-long region; pair B4502 and B4503, defining a 774 bp-long region; and pair B4504 and B4505, defining a 365 bp-long region.

Primer B4500 consists of sequence of PB1 phage genome (Acc. EU716414) ranging from position 31680 to 31697. Primer B4501 consists of sequence of PB1 phage genome (Acc. EU716414) ranging from position 31851 to 31872. Primer B4502 consists of sequence of PB1 phage genome (Acc. EU716414) ranging from position 31785 to 31804. Primer B4503 consists of sequence of PB1 phage genome (Acc. EU716414) ranging from position 32541 to 32558. Primer B4504 consists of sequence of PB1 phage genome (Acc. EU716414) ranging from position 32868 to 32888. Primer B4505 consists of sequence of PB1 phage genome (Acc. EU716414) ranging from position 33213 to 33232.

```
B4500
                          (SEQ ID NO: 3)
5'-GTGATCACACCCGAACTG-3'

B4501
                          (SEQ ID NO: 4)
5'-CGATGAAGAAGAGTTGGTTTTG-3'

B4502
                          (SEQ ID NO: 5)
5'-ACGCCGGACTACGAAATCAG-3'

B4503
                          (SEQ ID NO: 6)
5'-TCCGGAGACGTTGATGGT-3'

B4504
                          (SEQ ID NO: 7)
5'-CCTTTCATCGATTTCCACTTC-3'

B4505
                          (SEQ ID NO: 8)
5'-TTCGTGGACGCCCAGTCCCA-3'
```

2. Phi33-like tail fibre genes may be detected in experimental phage samples as follows:

Plaques of isolated phage of environmental origin may be picked from agar plates and added to water and incubated for 30 minutes, making plaque soak outs. The plaque soak outs may be diluted and a portion added to PCR reactions containing one or all of the above primer pairs, and PCR may be performed according to a standard protocol. PCR products may be visualised on a 1.5% agarose gel with ethidium bromide staining, and evaluated for their size. PCR products of the correct size for the primer pair used may be gel-extracted and submitted to an external facility for sequencing. Sequencing results may be compared with the available tail fibre gene sequences in order to confirm the identity of the PCR product.

An example of the construction of chimeric HRDs from two parental HRDs.

Selection of Module Boundaries

1. The amino acid sequences of the parental HRDs may be aligned using ClustalOmega and regions of highest sequence conservation may be so identified (FIGs. 7A-7B).
2. To generate chimeric HRDs comprising six modules, seven 4 nt cleavage sites (cs1 to cs7; FIGS. 2A-2B) may be selected from the most highly conserved regions of the alignment, according to the criteria previously outlined. As an example, i) cs1 (CTCG) forms the 5' boundary of module A (FIGS. 7A-7B; FIGS. 2A-2B) and is identical to that engineered into the acceptor site of the recipient plasmid, the delivery vector pSM1484A, at the junction between the conserved and hyper-variable regions of either HRD's full-length DNA sequence; ii) cs2 corresponds to GGAT, 162 nt downstream of cs1; iii) cs3, introducing a silent point mutation in HRD1, corresponds to GCGG 646 nt downstream of cs2; iv) cs4, introducing a silent point mutation in HRD1, corresponds to GGGA 37 nt downstream of cs3; v) cs5, introducing a silent point mutation in HRD1, corresponds to ACTC 28 nt downstream of cs4; vi) cs6 corresponds to TGGG 56 nt downstream of cs5; and finally, vii) cs7, corresponding to AATG 64 nt downstream of cs6, immediately downstream of the HRD stop codon, is identical to that engineered into the acceptor site of the recipient plasmid, the delivery vector pSM1484A.

Design and Cloning of Module Sequences

1. DNA fragments consisting of the different modules, flanked by suitable cs on either side, and with inverted BsaI restriction sites on either end of the DNA fragment may be generated by custom DNA synthesis. These services are widely available from companies such as Genscript and DNA2.0. The sequences of modules A-F, including flanking BsaI restriction sites and 4 bp cs, for both PTP92 and PTP47, are shown in FIGS. 2A-2B. As an alternative to custom DNA synthesis, another option may be to amplify the modules by PCR, with appropriate primers that incorporate the BsaI restriction sites and 4nt cs, using PTP92 or PTP47 DNA as template for the reactions.
2. Custom synthesised DNA modules may be subcloned into a suitable *E. coli* plasmid vector that lacks intrinsic BsaI restriction sites, and which uses an alternative selectable marker to that being used on the delivery vector. If pSM1484A is used as the delivery vector, the selectable marker for the module vectors must be something other than tetracycline resistance. A suitable vector could be a derivative of pUC57 from which the intrinsic BsaI restriction site has been silently removed (pUC57(–BsaI)). A library of clones in pUC57(–BsaI), each carrying a different module, may be thus generated. An example of the DNA sequences cloned in such a library is shown in FIGS. 2A-2B.

Construction of a Plasmid Library Containing Chimeric HRD, and Subsequent Transfer to *E. coli*

1. The acceptor plasmid, pSM1484A, and the module plasmids, pSMG1 to pSMG12 (FIGS. 2A-2B) may be prepared using standard methods, then quantified using a nanodrop, or by gel electrophoresis and comparison with a known standard.
2. The quantities of pSM1484A and pSMG1 to pSMG12 to use in each digestion/ligation reaction should be calculated such that the delivery vector (pSM1484A) and each of the modules A-F are present in equimolar amounts in the reaction. As an example, the amount of pSM1484A may be fixed at 200 ng in a 20 µl reaction.

The quantity of module plasmid (Q) (e.g. pSMG1, pSMG2, pSMG3, pSMG4, pSMG5, pSMG6, pSMG7, pSMG8, pSMG9, pSMG10, pSMG11 or pSMG12) required may be calculated according to the equation:

$$Q = \frac{\frac{M}{A} \times P}{N}$$

Where

M is the sequence length of the module plasmid (or DNA fragment length, if linear DNA molecules are being used instead of plasmids) in base pairs A is the sequence length of the delivery vector in base pairs Q is the quantity of module plasmid (or linear DNA fragment, if these are being used instead of plasmids) required in ng P is the amount of delivery vector being used in the reaction in ng N is the number of alternatives available for each module Taking pSMG1 as an example, M=2894 bp A=14039 bp P may be fixed at 200 ng, as described above N=2 (in this example, there are two alternatives for the module, i.e. module 1A and module 2A, originating from the HRD of PTP92 and PTP47 respectively).

Quantity of pSMG1 required per 200 ng of delivery vector, $$pSM1484A = \frac{\frac{2894}{14039} \times 200}{2}$$
$$= 20 \text{ ng}$$

3. The delivery vector and all of the module plasmids may then be mixed according to the calculated values in a single, 20 µl one-tube reaction that also contains T4 DNA ligase buffer, BsaI (20 Units), and T4 DNA ligase (40 Units). The assembled reaction may be placed in a thermal cycler for incubation at alternating temperatures as follows: 37° C. for 2 hours, then 50× (37° C., 2 minutes; 16° C., 3 minutes), then 50° C., 5 minutes, then 80° C., 10 minutes, and finally hold at 16° C.
4. The reaction may then be isopropanol-precipitated, resuspended in water and used to transform E. coli DH10B, according to standard protocols.
5. Successful clones derived from pSM1484A may be isolated by plating transformants onto medium containing tetracycline. Additionally, the plates may also contain a suitable substrate to visualise β-galactosidase activity, such as the chromogenic substrate S-gal. If required, clones carrying pSM1484A derivatives in which the lacZa reporter gene has been replaced by an insert between the vector BsaI restriction sites will appear white on S-gal plates, and thus may be distinguished from clones carrying the parental pSM1484A plasmids, which retain the lacZa reporter, and so will appear black on S-gal plates.
6. E. coli transformants containing the plasmid library may be harvested by aseptically scraping white colonies off the transformation plates, pooling them and resuspending in 10 ml LB. Ideally, $10^5$-$10^6$ transformant colonies should be pooled. The pooled library mixture may be either used directly, or may be stored in 25% glycerol (final concentration) at −20° C. for future use.

Figure 9A:
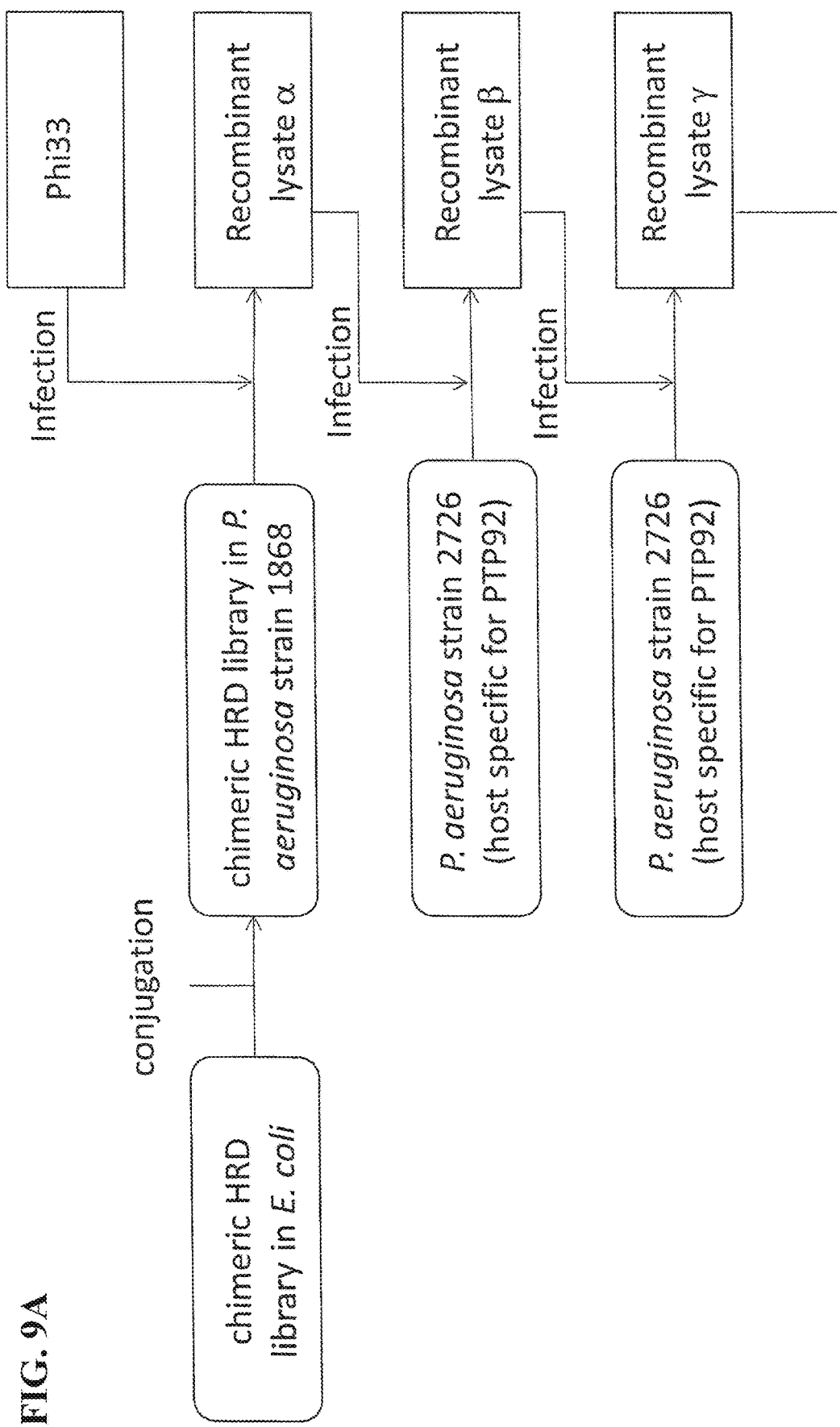
Figure 9B:
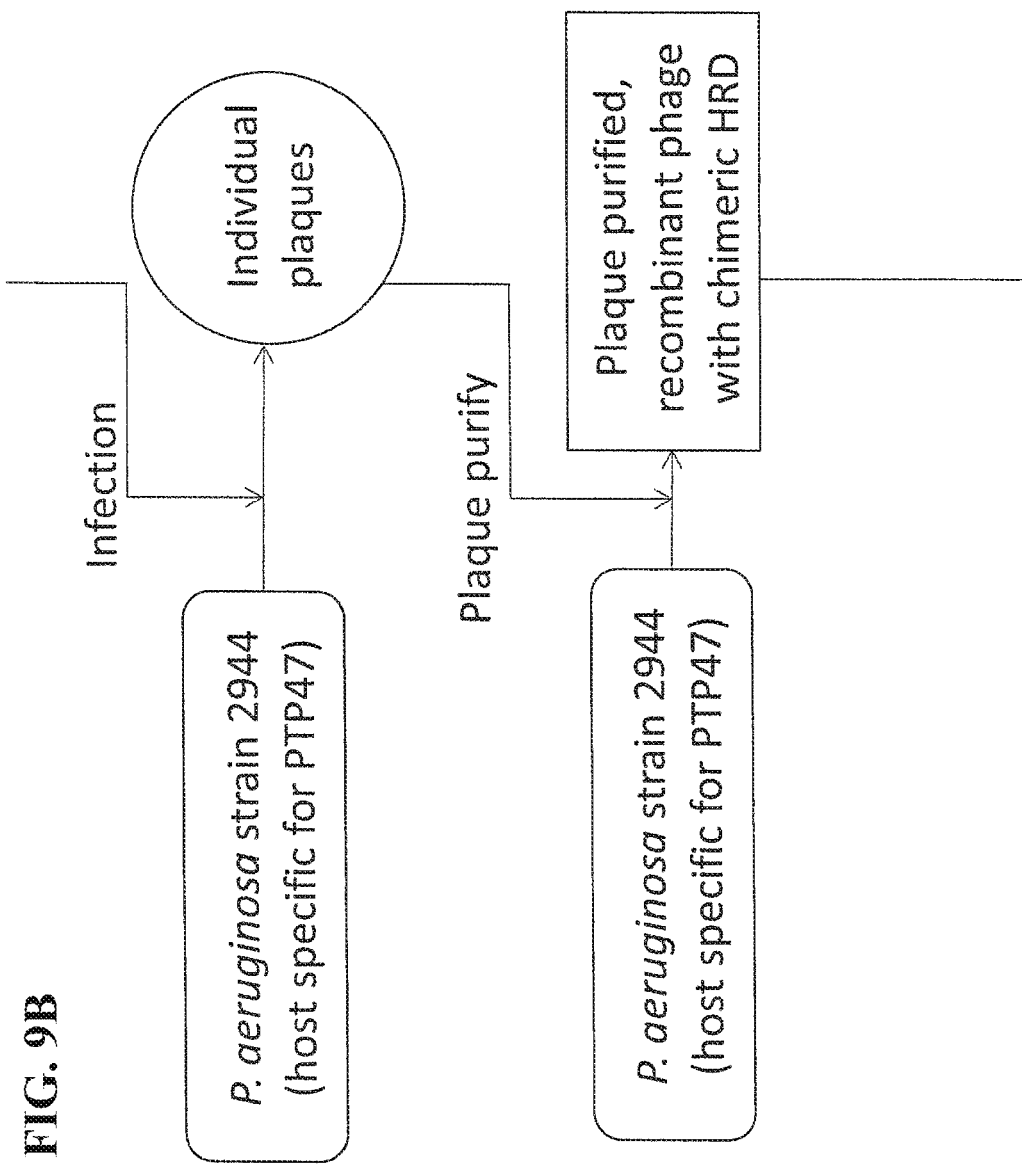
Figure 9C:
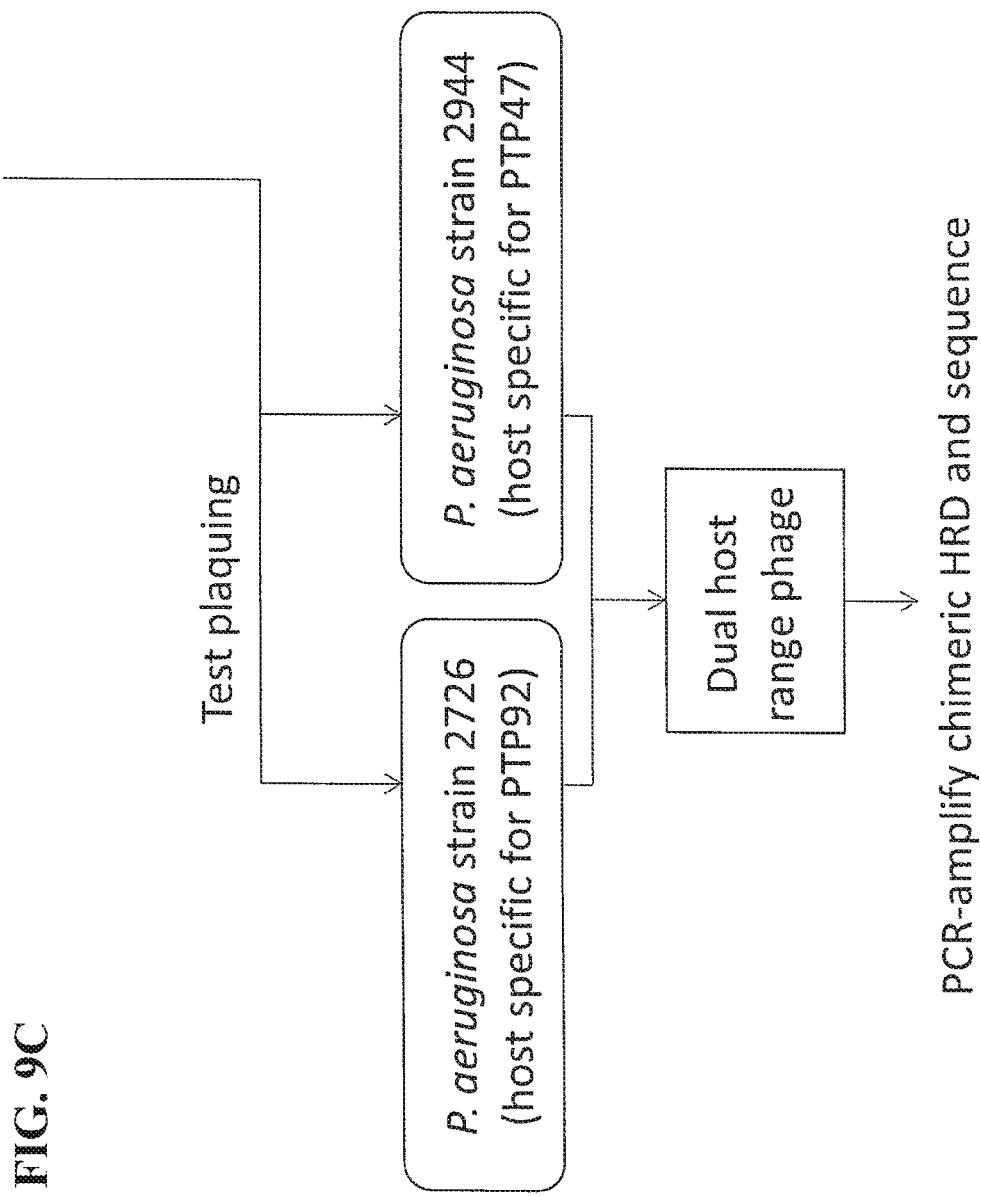

Generation of Phage Carrying Chimeric HRD, Via Recombination with the Plasmid Library 1. The pool of E. coli transformants harbouring the plasmid library may be used directly, or the glycerol stocks can be used to inoculate a fresh culture, for further work.
2. The plasmid library may be transferred from the pool of E. coli transformants, to P. aeruginosa strain 1868, which is a host for all three phage (Phi33, PTP47 and PTP92), by conjugation (FIGS. 9A-9C). Transformants may be selected on the basis of acquisition of tetracycline resistance.
3. The P. aeruginosa transformants containing the plasmid library may be harvested by aseptically scraping colonies off the transformation plates and pooling them and resuspending in 10 ml LB. Ideally, $10^5$-$10^6$ transformant colonies should be pooled. The pooled library mixture may either be used directly, or may be stored in 25% glycerol (final concentration) at −20° C. for future use.
4. The pool of P. aeruginosa transformants harbouring the plasmid library may then be used as a host on which a Phi33 phage lysate can be made (FIGS. 9A-9C). The resulting lysate (lysate α; FIGS. 9A-9C) should contain recombinant phage that have acquired chimeric HRD by homologous recombination with the plasmid library.
5. Lysate α, the Phi33 recombinant library, may then be plagued on Pseudomonas strain 2726, that is a host for PTP92, but not PTP47 or Phi33, and a new lysate made (lysate β), to isolate recombinant phage that have acquired the PTP92 host range associated with acquisition of elements of HRD1 (FIGS. 9A-9C).
6. Lysate 13 can then be re-plaqued on Pseudomonas strain 2726 and a second new lysate made (lysate 7), to enrich the phage library for candidates that have the PTP92 host range (FIGS. 9A-9C).
7. To isolate recombinant phage that have also acquired the PTP47 host range, lysate γ may be plagued on Pseudomonas strain 2944 that is a host for PTP47, but not PTP92 or Phi33 (FIGS. 9A-9C).
8. Individual plaques resulting from step 7 may be plaque purified on Pseudomonas strain 2944, and re-tested on Pseudomonas strain 2726, to confirm acquisition of the host ranges of both PTP92 and PTP47 (FIGS. 9A-9C).
9. The HRD region from the resulting purified phage that have the desired host range may be amplified by PCR using primers that bind to Phi33 genomic sequences located upstream and downstream of the regions of homology that were cloned into pSM1484A. The PCR product may then be sequenced to determine the sequence of the chimeric HRD (FIGS. 9A-9C).
10. One such phage that acquired the ability to plaque on both the PTP92 host (2726) and the PTP47 host (2944) was PTP238. Sequence analysis of the HRD of PTP238 revealed that it carried a chimeric HRD with the module organisation A2-B1-C2-D1-E1-F1, where modules designated '1' originated from PTP92, and modules designated '2' originated from PTP47. The amino acid sequence of the HRD from PTP238 is shown in FIG. 8.

REFERENCES

Abedon S T. (2008). Bacteriophage Ecology: Population Growth, Evolution, an Impact of Bacterial Viruses. Cambridge. Cambridge University Press. Chapter 1.

Boucher, H. W., Talbot, G. H., Bradley, J. S., Edwards, J. E., Gilbert, D., Rice, L. B., & Bartlett, J. (2009). Bad bugs, no drugs: no ESKAPE! An update from the Infectious Diseases Society of America. *Clinical Infectious Diseases*, 48: 1-12.

Burrowes, B., & Harper, D. R. (2012). Phage Therapy of Non-wound Infections. *Bacteriophages in Health and Disease: Bacteriophages in Health and Disease*, Chapter 14: 203-216.

Carlton, R. M. (1999). Phage therapy: past history and future prospects. Arclzivum *Immunologiae et Therapiae Experimentalis-English Edition* 47:267-274.

Ceyssens P, Miroshnikov K, Mattheus W, Krylov V, Robben J, Noben J, Vanderschraeghe S, Sykilinda N, Kropinski A M, Volckaert G, Mesyanzhinov V, Lavigne R. (2009). Comparative analysis of the widespread and conserved PB1-like viruses infecting *Pseudomonas aeruginosa. Env. Microbiol.* 11:2874-2883.

Duplessis, M. and Moineau, S., 2001. Identification of a genetic determinant responsible for host specificity in *Streptococcus thermophilus* bacteriophages. Molecular microbiology, 41(2), pp. 325-336.

Engler, C., Gruetzner, R., Kandzia, R. and Marillonnet, S., 2009. Golden gate shuffling: a one-pot DNA shuffling method based on type IIs restriction enzymes. PloS one, 4(5), p.e5553. Francesconi, S. C., MacAlister, T. J., Setlow, B., & Setlow, P. (1988). Immunoelectron microscopic localization of small, acid-soluble spore proteins in sporulating cells of *Bacillus subtilis. J Bacteriol.*, 170: 5963-5967.

Faure, K., Shimabukuro, D., Ajayi, T., Allmond, L. R., Sawa, T. and Wiener-Kronish, J. P., 2003. O-antigen serotypes and type III secretory toxins in clinical isolates of *Pseudomonas aeruginosa*. Journal of clinical microbiology, 41(5), pp. 2158-2160.

Frenkiel-Krispin, D., Sack, R., Englander, J., Shimoni, E., Eisenstein, M., Bullitt, E. & Wolf, S. G. (2004). Structure of the DNA-SspC complex: implications for DNA packaging, protection, and repair in bacterial spores. *J. Bacteriol.* 186:3525-3530.

Gill J J, Hyman P. (2010). Phage Choice, Isolation and Preparation for Phage therapy. *Current Pharmaceutical Biotechnology*. 11:2-14.

Kutateladze, M., & Adamia, R. (2010). Bacteriophages as potential new therapeutics to replace or supplement antibiotics. *Trends Biotechnol.* 28:591-595.

Lee, K. S., Bumbaca, D., Kosman, J., Setlow, P., & Jedrzejas, M. J. (2008). Structure of a protein—DNA complex essential for DNA protection in spores of *Bacillus* species. *Proc. Natl. Acad. Sci.* 105:2806-2811.

Lu, Q., Eggimann, P., Luyt, C. E., Wolff, M., Tamm, M., Francois, B., Mercier, E., Garbino, J., Laterre, P. F., Koch, H. and Gafner, V., 2014. *Pseudomonas aeruginosa* serotypes in nosocomial pneumonia: prevalence and clinical outcomes. Crit Care, 18(1), p. R17.

Marinelli, L. J., Piuri, M., Swigoňová, Z., Balachandran, A., Oldfield, L. M., van Kessel, J. C. and Hatfull, G. F., 2008. BRED: a simple and powerful tool for constructing mutant and recombinant bacteriophage genomes. PLoS One, 3(12), p.e3957.

Nicholson W L, Setlow B, Setlow P. (1990). Binding of DNA in vitro by a small, acid-soluble spore protein from *Bacillus subtilis* and the effect of this binding on DNA topology. *J Bacteriol.* 172:6900-6906.

Pan, Y. J., Lin, T. L., Chen, Y. H., Hsu, C. R., Hsieh, P. F., Wu, M. C. and Wang, J. T., 2013. Capsular types of *Klebsiella pneumoniae* revisited by wzc sequencing. PLoS One, 8(12), p.e80670.

Rakhuba D V, Kolomiets E I, Szwajcer Dey E, Novik E I. (2010). Bacteriophage Receptors, Mechanisms of Phage Adsorption and Penetration into Host Cell. *Polish J. Microbiol.* 59:145-155.

Rosenberg, S. M., Stahl, M. M., Kobayashi, I. and Stahl, F. W., 1985. Improved in vitro packaging of coliphage lambda DNA: a one-strain system free from endogenous phage. Gene, 38(1), pp. 165-175.

Sambrook, J., Fritsch, E. F., & Maniatis, T. (1989). *Molecular cloning* (Vol. 2, pp. 14-9). New York: Cold Spring Harbor Laboratory Press.

Shin, J. G., 2012. Molecular Programming with a Transcription and Translation Cell-Free Toolbox: From Elementary Gene Circuits to Phage Synthesis (Doctoral dissertation, UNIVERSITY OF MINNESOTA).

Veesler D, Cambillau C. (2011). A Common Evolutionary Origin for Tailed-Bacteriophage Functional Modules and Bacterial Machineries. *Microhiol Mol Biol Rev.* 75:423-433.

Walker, B., Barrett, S., Polasky, S., Galaz, V., Folke, C., Engstrom, G., & de Zeeuw, A. (2009). Looming global-scale failures and missing institutions. *Science*, 325:1345-1346.

Wang, L., Wang, Q. and Reeves, P. R., 2010. The variation of O antigens in gram-negative bacteria. In Endotoxins: Structure, Function and Recognition (pp. 123-152). Springer Netherlands.

Watt, V. M., Ingles, C. J., Urdea, M. S. and Rutter, W. J., 1985. Homology requirements for recombination in *Escherichia coli*. Proceedings of the National Academy of Sciences, 82(14), pp. 4768-4772.

WHO (2014) Antimicrobial resistance: global report on surveillance 2014.

The invention claimed is:

1. A method for producing one or more hybrid bacteriophage host range determinant (HRD) sequences, which comprises:

(1) identifying at least two DNA sequences, each encoding an HRD in a series of regions in the DNA sequence, wherein the HRDs are different from one another, (2) incorporating each region into a vector in which each region is flanked by a recognition site of a restriction enzyme capable of cutting DNA at a specific cleavage site outside of the recognition sequence, so that the cleavage site of the restriction enzyme is situated at the boundary of each region, wherein the cleavage site sequences of the regions from an individual series are different from one another and wherein the cleavage site sequences at the boundaries of corresponding regions from different series are the same;

(3) treating the vectors with a restriction enzyme capable of cutting DNA at a specific cleavage site outside of the recognition sequence so as to generate a mixture of the regions; and (4) treating the mixture of the regions with a ligase to ligate them to form an array of DNA sequences encoding an array of hybrid HRDs.

2. The method according to claim 1 wherein the restriction enzyme is selected from a Type IIB restriction enzyme and a Type IIS restriction enzyme.

3. The method according to claim 1, wherein steps (3) and (4) are carried out in a single reaction.

4. The method according to claim 1, wherein the restriction enzyme recognition sites are added to each region.

5. The method according to claim 1, wherein the regions are amplified or synthesised prior to incorporation into the vectors.

6. The method according to claim 1, wherein the cleavage site sequence of at least one of the regions is formed by changing the nucleotide base sequence of the region without changing the amino acid sequence encoded by the region.

7. The method according to claim 1, which further comprises (5) incorporating each hybrid HRD from the array of hybrid HRDs into a delivery vector to form an array of delivery vectors.

8. The method according to claim 7, wherein:

(a) the array of delivery vectors is contacted with first host cells so as to introduce each delivery vector into a first host cell to form an array of transformed first host cells;

(b) the array of transferred first host cells is infected with a target phage;

(c) phage replication and recombination are effected;

(d) recombinant phage are screened; and (e) recombinant phage bearing hybrid HRDs are selected.

9. The method according to claim 8, wherein steps (d) and (e) comprise propagating recombinant phage on a second host cell which is a host for phage bearing a hybrid HRD and not a host for the target phage.

10. The method according to claim 9, further comprising the steps:

(f) the selected recombinant phage bearing hybrid HRDs are contacted with the first host cells so as to infect the first host cells;

(g) phage replication is effected; and (h) recombinant phage bearing hybrid HRDs capable of infecting the first host cell and the second host cell are selected.

11. The method according to claim 1, wherein the at least two DNA sequences are identified by HRD nucleotide sequence alignment, HRD amino acid sequence alignment or HRD protein structure alignment.

12. The method according to claim 1, wherein the HRDs comprise tail fibre proteins, or tail fibre proteins wherein each tail fibre protein comprises a receptor binding region for binding to the target bacteria and a region linking the receptor binding region to the body of the bacteriophage.

13. The method according to claim 12, wherein the receptor binding region is a C-terminal receptor binding region and the region linking the C-terminal receptor binding region to the body of the bacteriophage is an N-terminal region.

14. The method according to claim 13, wherein the N-terminal region comprises amino acids 1 to 628 of the tail fibre protein and the C-terminal region comprises amino acids 629 to 964 of the tail fibre protein, based on the amino acid sequence of bacteriophage Phi33.

15. The method according to claim 2, wherein the Type IIS restriction enzyme is selected from BsaI, BpiI, BcoDI, BbvI, BbsI, BsmAI, BsmFI, FokI, SfaNI, BfuAI, BsmBI, BspMI, BtgZI, and Esp3I, or an isoschizomer thereof, or wherein the Type IIS restriction enzyme is selected from EarI, BspQI and SapI, or an isoschizomer thereof, or wherein the Type IIS restriction enzyme is HgaI, or an isoschizomer thereof, and/or wherein the Type IIB restriction enzyme is selected from AlfI, AloI, BaeI, BsgI, BplI, BsaXI, CspCI, FalI, PpiI and PsrI, or an isoschizomer thereof.

16. The method according to claim 8 wherein the recombinant phage bearing hybrid HRDs are provided with a gene encoding a protein which is toxic to a target bacterium.

17. The method according to claim 16 wherein the gene encodes an α/β-type small acid-soluble spore protein (SASP), a SASP-C, or a SASP-C from *Bacillus megaterium*.

18. The method according to claim 8, wherein step (e) comprises selecting a recombinant phage bearing hybrid HRDs which confer a host range which is broader than a host range of the target phage.

19. The method according to claim 8, wherein step (e) comprises selecting a recombinant phage bearing hybrid HRDs which confer a host range comprising the host ranges of the HRD sequences encoded by the at least two DNA sequences.

20. The method according to claim 8, wherein step (e) comprises selecting a recombinant phage bearing hybrid HRDs having a broad host range as defined by more than 50% of a collection of at least 35 and preferably more than 50 clinical isolates, from a plurality of different infection sites and including range of antibiotic resistance phenotypes.

* * * * *

SEQUENCE LISTING

<160> NUMBER OF SEQ ID NOS: 37

<210> SEQ ID NO 1
<211> LENGTH: 11
<212> TYPE: DNA
<213> ORGANISM: Artificial Sequence
<220> FEATURE:
<223> OTHER INFORMATION: BsaI site containing cs1

<400> SEQUENCE: 1
ctcgtgagac c                                                          11

```
<210> SEQ ID NO 2
<211> LENGTH: 11
<212> TYPE: DNA
<213> ORGANISM: Artificial Sequence
<220> FEATURE:
<223> OTHER INFORMATION: BsaI site containing cs7

<400> SEQUENCE: 2
ggtctcaaat g                                                             11

<210> SEQ ID NO 3
<211> LENGTH: 18
<212> TYPE: DNA
<213> ORGANISM: Artificial Sequence
<220> FEATURE:
<223> OTHER INFORMATION: primer based on PB1 phage genome

<400> SEQUENCE: 3
gtgatcacac ccgaactg                                                      18

<210> SEQ ID NO 4
<211> LENGTH: 22
<212> TYPE: DNA
<213> ORGANISM: Artificial Sequence
<220> FEATURE:
<223> OTHER INFORMATION: primer based on PB1 phage genome

<400> SEQUENCE: 4
cgatgaagaa gagttggttt tg                                                 22

<210> SEQ ID NO 5
<211> LENGTH: 20
<212> TYPE: DNA
<213> ORGANISM: Artificial Sequence
<220> FEATURE:
<223> OTHER INFORMATION: primer based on PB1 phage genome

<400> SEQUENCE: 5
acgccggact acgaaatcag                                                    20

<210> SEQ ID NO 6
<211> LENGTH: 18
<212> TYPE: DNA
<213> ORGANISM: Artificial Sequence
<220> FEATURE:
<223> OTHER INFORMATION: primer based on PB1 phage genome

<400> SEQUENCE: 6
tccggagacg ttgatggt                                                      18

<210> SEQ ID NO 7
<211> LENGTH: 21
<212> TYPE: DNA
<213> ORGANISM: Artificial Sequence
<220> FEATURE:
<223> OTHER INFORMATION: primer based on PB1 phage genome

<400> SEQUENCE: 7
cctttcatcg atttccactt c                                                  21

<210> SEQ ID NO 8
<211> LENGTH: 20
<212> TYPE: DNA
<213> ORGANISM: Artificial Sequence
<220> FEATURE:
<223> OTHER INFORMATION: primer based on PB1 phage genome
```

```
<400> SEQUENCE: 8
ttcgtggacg cccagtccca                                                20

<210> SEQ ID NO 9
<211> LENGTH: 184
<212> TYPE: DNA
<213> ORGANISM: Artificial Sequence
<220> FEATURE:
<223> OTHER INFORMATION: source phage PTP92

<400> SEQUENCE: 9
ggtctcactc ggcaataact cctatgtgat caccgacgaa tccaacatcc gaacccatat    60
caacacaatg gctgcgcgcc cgatttgggg gaatgtcgag ttctggggtc cgtggaactt   120
cgatccgaat cttaaactca ctttgaacgc tttcaatgat agctcataca ccaggattga   180
gacc                                                               184

<210> SEQ ID NO 10
<211> LENGTH: 184
<212> TYPE: DNA
<213> ORGANISM: Artificial Sequence
<220> FEATURE:
<223> OTHER INFORMATION: source phage PTP47

<400> SEQUENCE: 10
ggtctcactc ggcaataact cctatgtgat caccgacgaa tccaacatcc gaacccatat    60
caacacaatg gctgcgcgcc cgatttgggg gaatgtcgag ttctggggtc cgtggaactt   120
caatcctaac acgaagttga cgcttggctc attcaatgac ggccagcata ccaggattga   180
gacc                                                               184

<210> SEQ ID NO 11
<211> LENGTH: 668
<212> TYPE: DNA
<213> ORGANISM: Artificial Sequence
<220> FEATURE:
<223> OTHER INFORMATION: source phage PTP92

<400> SEQUENCE: 11
ggtctcagga tgaccaacag cggcgcgaaa gacgttggta tcgcgtccat gacgagttat    60
gctgatgcgg ccatgtcatt cttcaactat gaagcctcga atccgaccgg ccgcgcgcg   120 gccgttattt cgttcgtgag aaatggatcg cgtggagtgc tattcggctt ggattctgac   180
aacaagctga atggggcgg ctattctcta ggtgccgtcg cgttcgagat tgccgactcc   240
aacaacctca tgagcctgtg gtcatcccac gctgccgcgc cgaactggaa cgggcagacc   300
atctggaggt cgggaaactt caacccagac accaaggcga ctttggcagc tcgcaatacg   360
acgtcatccc ctacaatatt cagttatggg gcgtccggaa tcgcatcaac cggacaggtc   420
ggtgcgttgg ttgtggaaaa caacagcgtc accaataccg cagccgccat cacgttccat   480
tcgccgcaga aatatcaggt caacttcggc ctggatgcgc acaacgtggt aaagatcggt   540
ggcggcacaa tgggcggcgt agcatatccc atcatccact ccggcaacta caacaactac   600
atcaaccagg cgctggttca ggtaggtctt ggcggcgtcg gttcctacgc gatccttgcg   660
gtgagacc                                                           668

<210> SEQ ID NO 12
<211> LENGTH: 668
<212> TYPE: DNA
<213> ORGANISM: Artificial Sequence
```

```
<220> FEATURE:
<223> OTHER INFORMATION: source phage PTP47

<400> SEQUENCE: 12
ggtctcagga tggtcaacag cgccgcgaag gatgtaggaa ttgcgtccat gacgagctat      60
gcggacgcgg ctatgtcgtt cttcaactat gaggcttcga cgccgaccgg gaatcgtgct     120
gctgtaattt cgtttgttcg taacggggca cgaggcgttc tgttcggcct ggacacggac     180
aacaagctga atggggcgg ctattctcta ggtgccgtcg cgttcgagat tgccgactcc      240
aacaacctca tgagcctgtg gtcatcccac gctgccgcgc cgaactggaa cgggcagacc     300
atctggaggt cggaaaactt caacccagac accaaggcga ctttggcagc tcgcaatacg     360
acgtcatccc ctacaatatt cagttatggg gcgtccggaa tcgcatcaac cggacaggtc     420
ggtgcgttgg ttgtggaaaa caacagcgtc accaataccg cagccgccat cacgttccat     480
tcgccgcaga aatatcatgt caacttcggc ctggatgcgg acaacgtggt aaagatcggt     540
ggcggcacaa tgggcggcgt agcatatccc atcatccact ccggcaacta caacaactac     600
atcaaccagg cgctggttca ggtgggtctt ggcgaagtcg gttcctatgg catctttgcg     660
gtgagacc                                                              668

<210> SEQ ID NO 13
<211> LENGTH: 59
<212> TYPE: DNA
<213> ORGANISM: Artificial Sequence
<220> FEATURE:
<223> OTHER INFORMATION: source phage PTP92

<400> SEQUENCE: 13
ggtctcagcg gtattggaca cctccgcgcc ggcagcgtcc attgcccggg gatgagacc       59

<210> SEQ ID NO 14
<211> LENGTH: 59
<212> TYPE: DNA
<213> ORGANISM: Artificial Sequence
<220> FEATURE:
<223> OTHER INFORMATION: srouce phage PTP47

<400> SEQUENCE: 14
ggtctcagcg gttctggact atgccgctcc aaccgcgacc gttcgaccgg gatgagacc       59

<210> SEQ ID NO 15
<211> LENGTH: 50
<212> TYPE: DNA
<213> ORGANISM: Artificial Sequence
<220> FEATURE:
<223> OTHER INFORMATION: module PTP92

<400> SEQUENCE: 15
ggtctcaggg aacgatcatg gacagttcca agctgttcta ctctgagacc                 50

<210> SEQ ID NO 16
<211> LENGTH: 50
<212> TYPE: DNA
<213> ORGANISM: Artificial Sequence
<220> FEATURE:
<223> OTHER INFORMATION: source phage PTP47

<400> SEQUENCE: 16
ggtctcaggg agtggttgtg gacggttcca ttctcatcta ctctgagacc                 50

<210> SEQ ID NO 17
```

-continued

```
<211> LENGTH: 78
<212> TYPE: DNA
<213> ORGANISM: Artificial Sequence
<220> FEATURE:
<223> OTHER INFORMATION: source phage PTP92

<400> SEQUENCE: 17
ggtctcaact cgtcctgcga ttcgacctat cgcagcagcg ccagtccgac gggcacctgg    60
cgctgcatgg gtgagacc                                                  78

<210> SEQ ID NO 18
<211> LENGTH: 78
<212> TYPE: DNA
<213> ORGANISM: Artificial Sequence
<220> FEATURE:
<223> OTHER INFORMATION: source phage PTP47

<400> SEQUENCE: 18
ggtctcaact cgtcttgcgc cgcaaactac aatagcggtc aaaggcctgc cggaacttgg    60
cgctgcatgg gtgagacc                                                  78

<210> SEQ ID NO 19
<211> LENGTH: 86
<212> TYPE: DNA
<213> ORGANISM: Artificial Sequence
<220> FEATURE:
<223> OTHER INFORMATION: source phage PTP92

<400> SEQUENCE: 19
ggtctcatgg ggtatgtgta taaccgagac tccaccaacg gcgactcggc atccctattc    60
cagcgggtaa cgtaaaatgt gagacc                                         86

<210> SEQ ID NO 20
<211> LENGTH: 86
<212> TYPE: DNA
<213> ORGANISM: Artificial Sequence
<220> FEATURE:
<223> OTHER INFORMATION: source phage PTP47

<400> SEQUENCE: 20
ggtctcatgg gatatgtagt caaccgggat gccaacactc ctgactccgc gaccctttc    60 cagcgagtga cgtaaaatgt gagacc                                         86

<210> SEQ ID NO 21
<211> LENGTH: 964
<212> TYPE: PRT
<213> ORGANISM: Bacteriophage SPM1

<400> SEQUENCE: 21

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95
```

-continued

```
Val Gly Asn Asp Gly Ile Met Arg Arg Tyr Arg Ser Met Val Asn Ala
            100                 105                 110
Asn Ala Ser Asp Pro Leu Ser Thr Thr Trp Glu Glu Gln Pro Ala
        115                 120                 125
Trp Ser Val Met Arg Ser Asn Ile Pro Met Pro Ala Gly Gly Ser Gly
    130                 135                 140
Leu Ser Ser Gly Gly Glu Val Ile Thr Gly Arg Asn Phe Asn Asp
145                 150                 155                 160
Leu Leu Asn Gly Thr Trp Glu Phe Phe Ser Asp Ser Val Val Ala
                165                 170                 175
Ser Gln Asn Ala Pro Val Tyr Pro Ala Ser Ala Gly Ala Ala Gly
            180                 185                 190
Met Leu Glu Ala Lys Ser Trp Val Ser Gly Ala Asn Thr Phe Cys Val
        195                 200                 205
Gln Arg Tyr Thr Asp Arg Val Gly Asn Val Ala Val Arg Gly Leu Asn
    210                 215                 220
Ala Gly Ala Trp Thr Asn Trp Met Tyr Ala Val Asn Val Met Ala Leu
225                 230                 235                 240
Gln Gln Gly Arg Val Thr Tyr Gly Val Ala Ala Gly Ser Ala Asn Ala
                245                 250                 255
Tyr Thr Leu Thr Leu Val Pro Gln Leu Gln Gly Gly Leu Val Asp Gly
            260                 265                 270
Met Val Leu Arg Val Lys Phe Asn Ala Met Asn Thr Gly Ala Ser Thr
        275                 280                 285
Ile Asn Val Ser Gly Phe Gly Ser Lys Ala Ile Val Gly Ala Ala Asn
    290                 295                 300
Phe Pro Leu Thr Gly Gly Glu Leu Gly Gln Gly Leu Ile Ala Glu Leu
305                 310                 315                 320
Val Phe Asp Ala Thr Gly Asp Arg Trp Arg Ile Leu Ala Gly Ala Pro
                325                 330                 335
Arg Ile Gln Val Gly Asn Ala Asp Gln Asp Tyr Gln Ala Pro Ser Trp
            340                 345                 350
Lys Gln Val Lys Asp Tyr Val Ala Ser Gln Lys Leu Thr Glu Val Asp
        355                 360                 365
Trp Ala Asp Val Val Asn Lys Pro Asn Val Ala Ile Gln Asp Thr Thr
    370                 375                 380
Pro Trp Phe Ala Asn Leu Glu Leu Ser Asp Ala Arg Pro Phe Ile Asp
385                 390                 395                 400
Phe His Phe Asn Asn Asn Arg Ala Lys Asp Phe Asp Tyr Arg Phe Ile
                405                 410                 415
Ser Glu Ala Asp Gly Ser Met Ala Phe Tyr Ser Arg Gln Gly Ser Ala
            420                 425                 430
Gly Pro Thr Gln Asp Ile Leu Phe Ser Arg Ser Asn Val Thr Phe Leu
        435                 440                 445
Gln Pro Arg Leu Asp Val Ala Lys Asn Leu Ala Tyr Ile Ala Asn Ser
    450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Asn Ala Val Ile Ala Val
                485                 490                 495
Asn Thr Thr Asn Pro Asp Gly Ser Tyr Arg Ser Gln Ile Met Arg Trp
            500                 505                 510
```

-continued

Asp Trp Ala Ser Thr Asn Val Ile Phe Asn Asn Arg Pro Leu Phe Ala
                515                 520                 525

Gly Gln Tyr Val Pro Trp Asp Ser Gly Asn Phe Asp Pro Ala Thr Lys
530                 535                 540

Leu Thr Val Gly Thr Thr Asn Ile Ser Gly Pro Thr Gly Ile Arg
545                 550                 555                 560

Asn Thr Thr Ser Asn Thr Gly Asn Met Asn Thr Trp Gly Ser Ser Ser
                565                 570                 575

Thr Thr Ala Ser Tyr Gly Asn Ala Ala Leu Gln Ile Phe Gly Arg Gly
                580                 585                 590

Gly Gly Glu Pro Ala Ala Ile Tyr Phe Asp Asn Ser Gln Thr Gly Trp
                595                 600                 605

Tyr Leu Gly Met Asp Lys Asp Gly Gln Leu Lys Arg Ala Gly Trp Ser
                610                 615                 620

Leu Gly Asn Asn Ser Tyr Val Val Thr Asp Glu Ser Asn Ile Arg Asn
625                 630                 635                 640

His Val Asn Gly Met Ser Gly Ala Pro Val Trp Gly Gly Gln Trp Phe
                645                 650                 655

Trp Gly Glu Trp Asn Phe Asn Pro Asn Thr Lys Leu Thr Ile Lys Ala
                660                 665                 670

Gly Thr Gln Glu Thr Ser Ser Thr Ala Ile Phe Ser Gly Thr Leu Pro
                675                 680                 685

Phe Ala Pro Ile Ala Ser Leu Ser Asp Tyr Ser Gln Ala Pro Leu Thr
                690                 695                 700

Ile Tyr Asn Ser Pro Thr Gly Pro Ser Ala Lys Pro Ala Val Ile Ala
705                 710                 715                 720

Phe Ile Arg Pro Gly Asn Trp Gly Ala Phe Phe Gly Ile Asp Thr Asp
                725                 730                 735

Asn Lys Leu Lys Trp Gly Gly Ser Leu Gly Asn Asn Ser Arg Glu
                740                 745                 750

Ile Ala Asp Ser Ser Asn Ile Met Asn Leu Trp Ala Ser Asn Pro Thr
                755                 760                 765

Ala Pro Ser Trp Asn Gly Gln Thr Val Trp Arg Ser Gly Asn Phe Asp
770                 775                 780

Pro Ala Thr Lys Val Asp Leu Asn Ala Ala Asn Ala Thr Asn Gly Ser
785                 790                 795                 800

Met Ile Phe Asn Arg Ile Ser Gly Thr Gly Ser Ile Ala Ser Ser
                805                 810                 815

Gly Arg Val Gly Ala Ile Asn Leu Gln Asn Gly Ala His Ser Gly Gln
                820                 825                 830

Ala Ala Ala Val Thr Phe Glu Arg Gly Gly Ser Ile Phe Val Asn Phe
                835                 840                 845

Gly Leu Asp Thr Asp Asn Val Leu Lys Val Gly Gly Asn Leu Gly
850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Val Gly Ser Tyr Gly
                885                 890                 895

Ile Phe Ala Val Leu Asp Asn Ala Ala Pro Ile Ala Thr Val Gln Pro
                900                 905                 910

Gly Val Val Val Asp Gly Ser Ile Leu Ile Tyr Ser Ser Cys Ala Ala
                915                 920                 925

Asn Tyr Asn Ser Gly Gln Lys Pro Ala Gly Thr Trp Arg Cys Met Gly

```
            930                935                940
Tyr Val Val Asn Arg Asp Ala Asn Thr Ala Asp Ser Ala Thr Leu Phe
945                950                955                960

Gln Arg Val Thr

<210> SEQ ID NO 22
<211> LENGTH: 964
<212> TYPE: PRT
<213> ORGANISM: Bacteriophage F8

<400> SEQUENCE: 22

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Asn Ile Pro Met Pro Ala Gly Gly Ser Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ala Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Gly Ser Ala Asn Ala
                245                 250                 255

Tyr Thr Leu Thr Leu Val Pro Gln Leu Gln Gly Gly Leu Val Asp Gly
            260                 265                 270

Met Val Leu Arg Val Lys Phe Asn Ala Met Thr Gly Ala Ser Thr
        275                 280                 285

Ile Asn Val Ser Gly Phe Gly Ser Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
```

```
            340                 345                 350
Lys Gln Val Lys Asp Tyr Val Ala Ser Gln Lys Leu Thr Glu Val Asp
            355                 360                 365
Trp Ala Asp Val Val Asn Lys Pro Asn Val Ala Ile Gln Asp Thr Thr
        370                 375                 380
Pro Trp Phe Ala Asn Leu Glu Leu Ser Asp Ala Arg Pro Phe Ile Asp
385                 390                 395                 400
Phe His Phe Asn Asn Arg Ala Lys Asp Phe Asp Tyr Arg Phe Ile
                405                 410                 415
Ser Glu Ala Asp Gly Ser Met Ala Phe Tyr Ser Arg Gln Gly Ser Ala
            420                 425                 430
Gly Pro Thr Gln Asp Ile Leu Phe Ser Arg Ser Asn Val Thr Phe Leu
        435                 440                 445
Gln Pro Arg Leu Asp Val Ala Lys Asn Leu Ala Tyr Ile Ala Asn Ser
    450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Ala Val Ile Ala Val
                485                 490                 495
Asn Thr Thr Asn Pro Asp Gly Ser Tyr Arg Ser Gln Ile Met Arg Trp
            500                 505                 510
Asp Trp Ala Ser Thr Asn Val Ile Phe Asn Asn Arg Pro Leu Phe Ala
            515                 520                 525
Gly Gln Tyr Val Pro Trp Asp Ser Gly Asn Phe Asp Pro Ala Thr Lys
        530                 535                 540
Leu Thr Val Gly Thr Thr Asn Asn Ile Ser Gly Pro Thr Gly Ile Arg
545                 550                 555                 560
Asn Thr Thr Ser Asn Thr Gly Asn Met Asn Thr Trp Gly Ser Ser Ser
                565                 570                 575
Thr Thr Ala Ser Tyr Gly Asn Ala Ala Leu Gln Ile Phe Gly Arg Gly
            580                 585                 590
Gly Gly Glu Pro Ala Ala Ile Tyr Phe Asp Asn Ser Gln Thr Gly Trp
        595                 600                 605
Tyr Leu Gly Met Asp Lys Asp Gly Gln Leu Lys Arg Ala Gly Trp Ser
    610                 615                 620
Leu Gly Asn Asn Ser Tyr Val Val Thr Asp Glu Ser Asn Ile Arg Asn
625                 630                 635                 640
His Val Asn Gly Met Ser Gly Ala Pro Val Trp Gly Gly Gln Trp Phe
                645                 650                 655
Trp Gly Glu Trp Asn Phe Asn Pro Asn Thr Lys Leu Thr Ile Lys Ala
            660                 665                 670
Gly Thr Gln Glu Thr Ser Ser Thr Ala Ile Phe Ser Gly Thr Leu Pro
        675                 680                 685
Phe Ala Pro Ile Ala Ser Leu Ser Asp Tyr Ser Gln Ala Pro Leu Thr
    690                 695                 700
Ile Tyr Asn Ser Pro Thr Gly Pro Ser Ala Lys Pro Ala Val Ile Ala
705                 710                 715                 720
Phe Ile Arg Pro Gly Asn Trp Gly Ala Phe Phe Gly Ile Asp Thr Asp
                725                 730                 735
Asn Lys Leu Lys Trp Gly Gly Gly Ser Leu Gly Asn Asn Ser Arg Glu
            740                 745                 750
Ile Ala Asp Ser Ser Asn Ile Met Asn Leu Trp Ala Ser Asn Pro Thr
        755                 760                 765
```

```
Ala Pro Ser Trp Asn Gly Gln Thr Val Trp Arg Ser Gly Asn Phe Asp
            770                 775                 780
Pro Ala Thr Lys Val Asp Leu Asn Ala Ala Asn Ala Thr Asn Gly Ser
785                 790                 795                 800
Met Ile Phe Asn Arg Ile Ser Gly Thr Gly Ser Gly Ile Ala Ser Ser
                805                 810                 815
Gly Arg Val Gly Ala Ile Asn Leu Gln Asn Gly Ala His Ser Gly Gln
            820                 825                 830
Ala Ala Ala Val Thr Phe Glu Arg Gly Gly Ser Ile Phe Val Asn Phe
            835                 840                 845
Gly Leu Asp Thr Asp Asn Val Leu Lys Val Gly Gly Asn Leu Gly
            850                 855                 860
Ala Asn Ala Tyr Pro Val Ile His Ala Gly Asn Tyr Asn Asn Tyr Ile
865                 870                 875                 880
Asn Gln Ala Leu Val Gln Val Gly Leu Gly Gly Val Gly Ser Tyr Gly
            885                 890                 895
Ile Phe Ala Val Leu Asp Asn Ala Ala Pro Ile Ala Thr Val Gln Pro
                900                 905                 910
Gly Val Val Val Asp Gly Ser Ile Leu Ile Tyr Ser Ser Cys Ala Ala
            915                 920                 925
Asn Tyr Asn Ser Gly Gln Lys Pro Ala Gly Thr Trp Arg Cys Met Gly
            930                 935                 940
Tyr Val Val Asn Arg Asp Ala Asn Thr Ala Asp Ser Ala Thr Leu Phe
945                 950                 955                 960
Gln Arg Val Thr

<210> SEQ ID NO 23
<211> LENGTH: 964
<212> TYPE: PRT
<213> ORGANISM: Bacteriophage PB1

<400> SEQUENCE: 23

Met Ile Thr Pro Glu Leu Ile Pro Ser Pro Phe Ala Ala Gln Gly Asp
1               5                   10                  15
Lys Asp Pro Ile Pro Gln Thr Ser Ser Thr Gly Phe Ala Asn Leu Arg
            20                  25                  30
Asp Gly Tyr Thr Pro Asp Tyr Glu Ile Ser Leu Ala Ser Asn Asn Pro
        35                  40                  45
Gln Ala Lys Ala Val Glu Arg Lys Ile Gln Asn Gln Leu Phe Phe Ile
50                  55                  60
Ala Thr Gln Asn Ala Gln Ala Trp Gln Arg Gln Met Ala Pro Pro Trp
65                  70                  75                  80
Phe Gln Gly Met Pro Gly Gly Tyr Glu Gln Asn Ala Glu Val Val Arg
                85                  90                  95
Val Gly Asn Asp Gly Ile Met Arg Arg Tyr Arg Ser Met Val Asn Ala
            100                 105                 110
Asn Ala Ser Asp Pro Leu Ser Ser Thr Thr Trp Glu Glu Gln Pro Ala
        115                 120                 125
Trp Ser Val Met Arg Ser Asn Ile Pro Met Pro Ala Gly Gly Pro Gly
        130                 135                 140
Leu Ser Ser Gly Gly Glu Val Ile Thr Thr Gly Arg Asn Phe Asn Asp
145                 150                 155                 160
Leu Leu Asn Gly Thr Trp Glu Phe Phe Ser Asp Ser Val Val Val Ala
                165                 170                 175
```

```
Ser Gln Asn Ala Pro Val Tyr Pro Ala Ser Gly Ala Ala Gly
            180                 185                 190

Met Leu Glu Ala Lys Ser Trp Ile Ser Gly Ser Asn Thr Phe Cys Val
            195                 200                 205

Gln Arg Tyr Thr Asp Arg Val Gly Asn Val Ala Val Arg Gly Leu Asn
            210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Val Asn Thr Gly Ala Ser Thr
            275                 280                 285

Ile Asn Val Ser Gly Phe Gly Ala Lys Ala Ile Val Gly Ala Ala Asn
            290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
385                 390                 395                 400

Phe His Phe Asn Asn Asn Arg Ala Lys Asp Phe Asp Tyr Arg Phe Ile
                405                 410                 415

Ser Glu Ala Asp Gly Ser Met Ala Phe Tyr Ser Arg Gln Gly Ser Ala
            420                 425                 430

Gly Pro Thr Gln Asp Ile Leu Phe Ser Arg Ser Asn Val Thr Phe Leu
            435                 440                 445

Gln Pro Arg Leu Asp Val Ala Lys Asn Leu Ala Tyr Ile Ala Asn Ser
            450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
            500                 505                 510

Asp Trp Ala Ser Thr Asn Val Ile Phe Asn Asn Arg Pro Leu Phe Ala
            515                 520                 525

Gly Gln Tyr Val Pro Trp Asp Ser Gly Asn Phe Asp Pro Ala Thr Lys
            530                 535                 540

Leu Thr Val Gly Thr Thr Asn Asn Ile Ser Gly Pro Thr Gly Ile Arg
545                 550                 555                 560

Asn Thr Thr Ser Asn Thr Gly Asn Met Asn Thr Trp Gly Ser Ser Ser
                565                 570                 575

Thr Thr Ala Ser Tyr Gly Asn Ala Ala Leu Gln Ile Phe Gly Arg Gly
            580                 585                 590
```

```
Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
        610                 615                 620

Leu Gly Asn Asn Ser Tyr Val Val Thr Asp Glu Ser Asn Ile Arg Asn
625                 630                 635                 640

His Val Asn Gly Met Ser Gly Ala Pro Val Trp Gly Gln Trp Phe
            645                 650                 655

Trp Gly Glu Trp Asn Phe Asn Pro Asn Thr Lys Leu Thr Ile Lys Ala
            660                 665                 670

Gly Thr Gln Glu Thr Ser Ser Thr Ala Ile Phe Ser Gly Thr Leu Pro
            675                 680                 685

Phe Ala Pro Ile Ala Ser Leu Ser Asp Tyr Ser Gln Ala Pro Leu Thr
            690                 695                 700

Ile Tyr Asn Ser Pro Thr Gly Pro Ser Ala Lys Pro Ala Val Ile Ala
705                 710                 715                 720

Phe Ile Arg Pro Gly Asn Trp Gly Ala Phe Gly Ile Asp Thr Asp
            725                 730                 735

Asn Lys Leu Lys Trp Gly Gly Gly Ser Leu Gly Asn Asn Ser Arg Glu
            740                 745                 750

Ile Ala Asp Ser Ser Asn Ile Met Asn Leu Trp Ala Ser Asn Pro Thr
            755                 760                 765

Ala Pro Ser Trp Asn Gly Gln Thr Val Trp Arg Ser Gly Asn Phe Asp
            770                 775                 780

Pro Ala Thr Lys Val Asp Leu Asn Ala Ala Asn Ala Thr Asn Gly Asn
785                 790                 795                 800

Met Ile Phe Asn Arg Ile Ser Gly Thr Gly Ser Gly Ile Ala Ser Ser
            805                 810                 815

Gly Arg Val Gly Ala Ile Asn Leu Gln Asn Gly Ala His Ser Gly Gln
            820                 825                 830

Ala Ala Ala Val Thr Phe Glu Arg Gly Gly Ser Ile Phe Val Asn Phe
            835                 840                 845

Gly Leu Asp Thr Asp Asn Val Leu Lys Val Gly Gly Gly Asn Leu Gly
            850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Val Gly Ser Tyr Gly
            885                 890                 895

Ile Phe Ala Val Leu Asp Asn Ala Ala Pro Ile Ala Thr Val Gln Pro
            900                 905                 910

Gly Val Val Val Asp Gly Ser Ile Leu Ile Tyr Ser Ser Cys Ala Ala
            915                 920                 925

Asn Tyr Asn Ser Gly Gln Lys Pro Ala Gly Thr Trp Arg Cys Met Gly
            930                 935                 940

Tyr Val Val Asn Arg Asp Ala Asn Thr Pro Asp Ser Ala Thr Leu Phe
945                 950                 955                 960

Gln Arg Val Thr

<210> SEQ ID NO 24
<211> LENGTH: 964
<212> TYPE: PRT
<213> ORGANISM: Bacteriophage C36

<400> SEQUENCE: 24
```

```
Met Ile Thr Pro Glu Leu Ile Pro Ser Pro Phe Ala Ala Gln Gly Asp
 1               5                  10                 15

Lys Asp Pro Ile Pro Gln Thr Ser Ser Thr Gly Phe Ala Asn Leu Arg
             20                  25                  30

Asp Gly Tyr Thr Pro Asp Tyr Glu Ile Ser Leu Ala Ser Asn Asn Pro
             35                  40                  45

Gln Ala Lys Ala Val Glu Arg Lys Ile Gln Asn Gln Leu Phe Phe Ile
 50                  55                  60

Ala Thr Gln Asn Ala Gln Ala Trp Gln Arg Gln Met Ala Pro Pro Trp
 65                  70                  75                  80

Phe Gln Gly Met Pro Gly Gly Tyr Glu Gln Asn Ala Glu Val Val Arg
                 85                  90                  95

Val Gly Asn Asp Gly Ile Met Arg Arg Tyr Arg Ser Met Val Asn Ala
             100                 105                 110

Asn Ala Ser Asp Pro Leu Ser Ser Thr Thr Trp Glu Glu Gln Pro Ala
             115                 120                 125

Trp Ser Val Met Arg Ser Ser Ile Pro Met Pro Ala Gly Gly Pro Gly
             130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Val Ala
                 165                 170                 175

Ser Gln Asn Ala Pro Val Tyr Pro Ala Ser Ala Gly Ala Ala Ala Gly
                 180                 185                 190

Met Leu Glu Ala Lys Ser Trp Ile Ser Gly Ser Asn Thr Phe Cys Val
                 195                 200                 205

Gln Arg Tyr Thr Asp Arg Val Gly Asn Val Ala Val Arg Gly Leu Asn
                 210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Pro Ala Asn Ala
                 245                 250                 255

Tyr Thr Leu Thr Leu Val Pro Gln Leu Gln Gly Gly Leu Val Asp Gly
                 260                 265                 270

Met Ile Leu Arg Val Lys Phe Asn Thr Val Asn Thr Gly Ala Ser Thr
                 275                 280                 285

Ile Asn Val Ser Gly Phe Gly Ala Lys Ala Ile Val Gly Ala Ala Asn
                 290                 295                 300

Phe Pro Leu Thr Gly Gly Glu Leu Gly Gln Gly Leu Ile Ala Glu Leu
305                 310                 315                 320

Val Phe Asp Ala Thr Gly Asp Arg Trp Arg Ile Leu Ala Gly Ala Pro
                 325                 330                 335

Arg Ile Gln Val Gly Asn Ala Asp Gln Asp Tyr Gln Ala Pro Ser Trp
                 340                 345                 350

Lys Gln Val Lys Asp Tyr Val Ala Ser Gln Lys Leu Thr Glu Val Asp
                 355                 360                 365

Trp Ala Asp Val Val Asn Lys Pro Asn Val Ala Ile Gln Asp Thr Thr
                 370                 375                 380

Pro Trp Phe Ala Asn Leu Glu Leu Ser Asp Ala Arg Pro Phe Ile Asp
385                 390                 395                 400

Phe His Phe Asn Asn Asn Arg Ala Lys Asp Phe Asp Tyr Arg Phe Ile
                 405                 410                 415

Ser Glu Ala Asp Gly Ser Met Ala Phe Tyr Ser Arg Gln Gly Ser Ala
```

```
            420                 425                 430
Gly Pro Thr Gln Asp Ile Leu Phe Ser Arg Ser Asn Val Thr Phe Leu
            435                 440                 445
Gln Pro Arg Leu Asp Val Ala Lys Asn Leu Ala Tyr Ile Ala Asn Ser
450                 455                 460
Gly Pro Leu Trp Gln Asn Thr Thr Ala Asp Gln Pro Gly Trp Lys Phe
465                 470                 475                 480
Thr Phe Ala Gln Gly Val Asp Ala Asn Asn Ala Val Ile Ala Val
            485                 490                 495
Asn Thr Thr Asn Pro Asp Gly Ser Tyr Arg Ser Gln Ile Met Arg Trp
            500                 505                 510
Asp Trp Ala Ser Thr Asn Val Ile Phe Asn Asn Arg Pro Leu Phe Ala
            515                 520                 525
Gly Gln Tyr Val Pro Trp Asp Ser Gly Asn Phe Asp Pro Ala Thr Lys
            530                 535                 540
Leu Thr Val Gly Thr Thr Asn Ile Ser Gly Pro Thr Gly Ile Arg
545                 550                 555                 560
Asn Thr Thr Ser Asn Thr Gly Asn Met Asn Thr Trp Gly Ser Ser Ser
            565                 570                 575
Thr Thr Ala Ser Tyr Gly Asn Ala Ala Val Gln Ile Phe Gly Arg Gly
            580                 585                 590
Asp Gly Glu Pro Ala Ala Ile Tyr Phe Asp Asn Ser Gln Thr Gly Trp
            595                 600                 605
Tyr Leu Gly Met Asp Lys Asp Gly Gln Leu Lys Arg Ala Gly Trp Ser
            610                 615                 620
Leu Gly Asn Asn Ser Tyr Val Val Thr Asp Glu Ser Asn Ile Arg Phe
625                 630                 635                 640
His Val Asn Ser Met Ala Gly Thr Pro Val Trp Gly Gly Asn Glu Phe
            645                 650                 655
Trp Gly Pro Trp Asn Phe Asn Pro Asn Thr Lys Leu Thr Ile Lys Ala
            660                 665                 670
Gly Thr Gln Glu Thr Ser Ser Thr Ala Ile Phe Ser Gly Thr Met Pro
            675                 680                 685
Phe Ala Pro Ile Ala Ser Leu Ser Asp Tyr Ser Gln Ala Pro Leu Thr
            690                 695                 700
Ile Tyr Asn Ser Pro Thr Gly Pro Ser Ala Lys Pro Ala Val Ile Ala
705                 710                 715                 720
Phe Ile Arg Pro Gly Asn Trp Gly Ala Phe Phe Gly Ile Asp Thr Asp
            725                 730                 735
Asn Lys Leu Lys Trp Gly Gly Ser Leu Gly Asn Ser Ser Arg Glu
            740                 745                 750
Ile Ala Asp Ser Ser Asn Ile Met Asn Leu Trp Ala Ala Asn Pro Thr
            755                 760                 765
Ala Pro Ser Trp Asn Gly Gln Thr Val Trp Arg Ser Gly Asn Phe Asp
            770                 775                 780
Pro Ala Thr Lys Val Asp Leu Asn Ala Ala Asn Ala Thr Asn Gly Asn
785                 790                 795                 800
Met Val Phe Asn Arg Ile Ser Gly Thr Gly Ser Gly Ile Ala Ser Ser
            805                 810                 815
Gly Arg Val Gly Ala Ile Asn Leu Gln Asn Gly Ala His Ser Gly Gln
            820                 825                 830
Ala Ala Ala Val Thr Phe Glu Arg Gly Gly Ser Ile Phe Val Asn Phe
            835                 840                 845
```

```
Gly Leu Asp Thr Asp Asn Val Leu Lys Val Gly Gly Asn Leu Gly
        850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Gly Val Gly Ser Tyr Gly
                885                 890                 895

Ile Phe Ala Val Leu Asp Asn Ala Ala Pro Ile Ala Thr Val Gln Pro
                900                 905                 910

Gly Val Val Asp Gly Ser Ile Leu Ile Tyr Ser Ser Cys Ser Ala
            915                 920                 925

Asn Tyr Asn Ser Gly Gln Arg Pro Ala Gly Thr Trp Arg Cys Met Gly
        930                 935                 940

Tyr Val Val Asn Arg Asp Ala Asn Thr Pro Asp Ser Ala Thr Leu Phe
945                 950                 955                 960

Gln Arg Val Thr

<210> SEQ ID NO 25
<211> LENGTH: 964
<212> TYPE: PRT
<213> ORGANISM: Bacteriophage LBL3

<400> SEQUENCE: 25

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
            35                  40                  45

Gln Ala Lys Ala Val Glu Arg Lys Ile Gln Asn Gln Leu Phe Phe Ile
        50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Asn Ile Pro Met Pro Ala Gly Gly Pro Gly
130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255
```

-continued

Tyr Thr Leu Thr Leu Val Pro Gln Leu Gln Gly Gly Leu Val Asp Gly
            260             265             270

Met Ile Leu Arg Val Lys Phe Asn Thr Met Asn Thr Gly Ala Ser Thr
            275             280             285

Ile Asn Val Ser Gly Phe Gly Ala Lys Ala Ile Val Gly Ala Ala Asn
    290             295             300

Phe Pro Leu Thr Gly Gly Glu Leu Gly Gln Gly Leu Ile Ala Glu Leu
305             310             315             320

Val Phe Asp Ala Thr Gly Asp Arg Trp Arg Ile Leu Ala Gly Ala Pro
            325             330             335

Arg Ile Gln Val Gly Asn Ala Asp Gln Asp Tyr Gln Ala Pro Ser Trp
            340             345             350

Lys Gln Val Lys Asp Tyr Val Ala Ser Gln Lys Leu Thr Glu Val Asp
            355             360             365

Trp Ala Asp Val Val Asn Lys Pro Asn Val Ala Ile Gln Asp Thr Thr
    370             375             380

Pro Trp Phe Ala Asn Leu Glu Leu Ser Asp Ala Arg Pro Phe Ile Asp
385             390             395             400

Phe His Phe Asn Asn Arg Ala Lys Asp Phe Asp Tyr Arg Phe Ile
            405             410             415

Ser Glu Ala Asp Gly Ser Met Ala Phe Tyr Ser Arg Gln Gly Ser Ala
            420             425             430

Gly Pro Thr Gln Asp Ile Leu Phe Ser Arg Ser Asn Val Thr Phe Leu
            435             440             445

Gln Pro Arg Leu Asp Val Ala Lys Asn Leu Ala Tyr Ile Ala Asn Ser
    450             455             460

Gly Pro Leu Trp Gln Asn Thr Thr Ala Asp Gln Pro Gly Trp Lys Phe
465             470             475             480

Thr Phe Ala Gln Gly Val Asp Ala Asn Asn Ala Val Ile Ala Val
            485             490             495

Asn Thr Thr Asn Pro Asp Gly Ser Tyr Arg Ser Gln Ile Met Arg Trp
    500             505             510

Asp Trp Ala Ser Thr Asn Val Ile Phe Asn Asn Arg Pro Leu Phe Ala
    515             520             525

Gly Gln Tyr Val Pro Trp Asp Ser Gly Asn Phe Asp Pro Ala Thr Lys
530             535             540

Leu Thr Val Gly Thr Thr Asn Asn Ile Ser Arg Pro Thr Gly Ile Arg
545             550             555             560

Asn Thr Thr Ser Asn Thr Gly Asn Met Asn Thr Trp Gly Ser Ser Ser
            565             570             575

Thr Thr Ala Ser Tyr Gly Asn Ala Ala Leu Gln Ile Phe Gly Arg Gly
            580             585             590

Gly Gly Glu Pro Ala Ala Ile Tyr Phe Asp Asn Ser Gln Thr Gly Trp
            595             600             605

Tyr Leu Gly Met Asp Lys Asp Gly Gln Leu Lys Arg Ala Gly Trp Ser
            610             615             620

Leu Gly Asn Asn Ser Tyr Val Val Thr Asp Glu Ser Asn Ile Arg Phe
625             630             635             640

His Val Asn Ser Met Ala Gly Thr Pro Val Trp Gly Asn Glu Phe
            645             650             655

Trp Gly Pro Trp Asn Phe Asn Pro Asn Thr Lys Leu Thr Ile Lys Ala
            660             665             670

```
Gly Thr Gln Glu Thr Ser Ser Thr Ala Ile Phe Ser Gly Thr Met Pro
            675                 680                 685

Phe Ala Pro Ile Ala Ser Leu Ser Asp Tyr Ser Gln Ala Pro Leu Thr
690                 695                 700

Val Tyr Asn Ser Pro Thr Gly Pro Ser Ala Lys Pro Ala Val Ile Ala
705                 710                 715                 720

Phe Ile Arg Pro Gly Asn Trp Gly Ala Phe Gly Ile Asp Thr Asp
                725                 730                 735

Asn Lys Leu Lys Trp Gly Gly Ser Leu Gly Asn Ser Ser Arg Glu
            740                 745                 750

Ile Ala Asp Ser Ser Asn Ile Met Asn Leu Trp Ala Ala Asn Pro Thr
            755                 760                 765

Ala Pro Thr Trp Asn Gly Gln Thr Ile Trp Arg Ser Gly Asn Phe Asp
770                 775                 780

Pro Ala Thr Lys Val Asp Leu Asn Ala Ala Asn Ala Thr Asn Gly Asn
785                 790                 795                 800

Met Ile Phe Asn Arg Ile Ala Gly Thr Gly Ser Gly Ile Ala Ser Ser
                805                 810                 815

Asp Arg Val Gly Ala Ile Ser Leu Gln Asn Gly Ala Thr Ala Gly Ala
            820                 825                 830

Ala Ala Ala Val Thr Phe Glu Arg Gly Gly Gly Phe Phe Val Asn Phe
            835                 840                 845

Gly Leu Asp Thr Asp Asn Val Leu Lys Val Gly Gly Gly Asn Leu Gly
    850                 855                 860

Ala Asn Ala Tyr Pro Val Ile His Ala Gly Asn Tyr Asn Asn Tyr Ile
865                 870                 875                 880

Asn Gln Ala Leu Val Gln Val Gly Leu Gly Gly Val Gly Ser Tyr Gly
                885                 890                 895

Ile Phe Ala Val Leu Asp Tyr Ala Ala Pro Thr Ala Thr Val Gln Pro
            900                 905                 910

Gly Val Ile Val Asp Gly Ser Ile Leu Ile Tyr Ser Ser Cys Ser Ala
            915                 920                 925

His Tyr Asn Ser Gly Gln Arg Pro Ala Gly Thr Trp Arg Cys Met Gly
    930                 935                 940

Tyr Val Leu Asn Arg Asp Ala Arg Asp Pro Asp Ser Ala Thr Leu Phe
945                 950                 955                 960

Gln Arg Val Thr

<210> SEQ ID NO 26
<211> LENGTH: 964
<212> TYPE: PRT
<213> ORGANISM: Bacteriophage Phi33

<400> SEQUENCE: 26

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
            35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80
```

```
Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ile Asp Pro Leu Ser Ser Thr Thr Trp Glu Glu Gln Pro Ala
            115                 120                 125

Trp Ser Val Met Arg Ser Asn Ile Pro Met Pro Ala Gly Gly Pro Gly
            130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Val Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
            195                 200                 205

Gln Arg Tyr Thr Asp Arg Val Gly Asn Val Ala Val Arg Gly Leu Asn
            210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Ser Thr
            275                 280                 285

Ile Asn Val Ser Gly Leu Gly Ala Lys Ala Ile Val Gly Ala Ala Asn
            290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
            435                 440                 445

Gln Pro Arg Leu Asp Val Ala Lys Asn Leu Ala Tyr Ile Ala Asn Ser
            450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Ile Met Arg Trp
```

```
            500             505             510
Asp Trp Ala Ser Thr Asn Val Ile Phe Asn Asn Arg Pro Leu Phe Ala
            515             520             525

Gly Gln Tyr Val Pro Trp Asp Ser Gly Asn Phe Asp Pro Ser Thr Lys
            530             535             540

Leu Thr Val Asn Ala Thr Asn Gln Ile Ala Gly Pro Thr Gly Ile Arg
545             550             555             560

Asn Thr Asn Gly Asn Thr Gly Asn Met Asn Thr Trp Gly Ser Gly Ser
                565             570             575

Thr Thr Ala Ser Tyr Gly Asn Ala Ala Leu Gln Ile Phe Gly Lys Gly
            580             585             590

Gly Gly Glu Pro Ala Ala Leu Tyr Phe Asp Asn Ser Gln Thr Gly Trp
            595             600             605

Tyr Leu Gly Met Asp Lys Asp Gly Gln Leu Lys Arg Ala Gly Trp Ser
            610             615             620

Leu Gly Asn Asn Ala Tyr Val Ile Thr Asp Glu Ser Asn Ile Arg Phe
625             630             635             640

His Val Asn Ser Met Ala Gly Thr Pro Val Trp Gly Gly Asn Glu Phe
                645             650             655

Trp Gly Pro Trp Asn Phe Asn Pro Asn Thr Lys Leu Thr Ile Lys Ala
            660             665             670

Gly Thr Gln Glu Thr Ser Ser Thr Ala Ile Phe Ser Thr Met Pro
            675             680             685

Phe Ala Pro Ile Ala Ser Leu Ser Asp Tyr Ser Gln Ala Pro Leu Thr
            690             695             700

Val Tyr Asn Ala Pro Thr Gly Pro Ser Ala Lys Pro Ala Val Ile Ala
705             710             715             720

Phe Ile Arg Pro Gly Asn Trp Gly Ala Phe Phe Gly Ile Asp Thr Asp
                725             730             735

Asn Lys Leu Lys Trp Gly Gly Gly Ser Leu Gly Asn Ser Ser Arg Glu
            740             745             750

Ile Ala Asp Ser Ser Asn Ile Met Asn Leu Trp Ala Ala Asn Pro Thr
            755             760             765

Ala Pro Ser Trp Asn Gly Gln Thr Ile Trp Arg Ser Gly Asn Phe Asp
            770             775             780

Pro Ala Thr Lys Val Asp Leu Asn Ala Ala Asn Ala Thr Asn Gly Asn
785             790             795             800

Met Ile Phe Asn Arg Ile Ala Gly Thr Gly Ser Gly Ile Ala Ser Ser
                805             810             815

Gly Arg Val Gly Ala Ile Asn Leu Gln Asn Gly Glu His Ser Gly Gln
            820             825             830

Ala Ala Ala Val Thr Phe Glu Arg Gly Gly Ser Ile Phe Val Asn Phe
            835             840             845

Gly Leu Asp Thr Asp Asn Val Leu Lys Val Gly Gly Asn Leu Gly
            850             855             860

Ala Asn Ala Tyr Pro Val Ile His Ala Gly Asn Tyr Asn Asn Tyr Ile
865             870             875             880

Asn Gln Ala Leu Val Gln Val Gly Leu Glu Gly Val Gly Ser Tyr Gly
                885             890             895

Ile Phe Ala Val Leu Asp Asn Ala Ala Pro Thr Ala Thr Val Gln Pro
            900             905             910

Gly Val Val Val Asp Gly Ser Ile Leu Ile Tyr Ser Ser Cys Ala Ala
            915             920             925
```

```
Asn Tyr Asn Ser Gly Lys Arg Pro Ala Gly Thr Trp Arg Cys Met Gly
            930                 935                 940

Tyr Val Val Asn Arg Asp Ala Asn Thr Pro Asp Ser Ala Thr Leu Phe
945                 950                 955                 960

Gln Arg Val Thr

<210> SEQ ID NO 27
<211> LENGTH: 964
<212> TYPE: PRT
<213> ORGANISM: Bacteriophage LMA2

<400> SEQUENCE: 27

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Val Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Ala Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Thr Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335
```

```
Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
            435                 440                 445

Gln Pro Arg Leu Asp Val Ala Lys Asn Leu Ala Tyr Ile Ala Asn Ser
            450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
            485                 490                 495

Asn Thr Thr Asn Pro Asp Gly Ser Tyr Arg Ser Gln Val Met Arg Trp
            500                 505                 510

Asp Trp Ala Ser Thr Asn Val Ile Phe Asn Asn Arg Pro Leu Phe Ala
            515                 520                 525

Gly Gln Tyr Thr Pro Trp Asp Ser Gly Asn Phe Asp Pro Ser Thr Lys
            530                 535                 540

Leu Thr Val Asn Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Gln Ile Phe Gly Lys Gly
            580                 585                 590

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
            610                 615                 620

Leu Gly Asn Asn Ser Tyr Val Ile Thr Asp Glu Leu Asn Ile Arg Asn
625                 630                 635                 640

His Ile Asn Gly Met Ala Ala Arg Pro Val Trp Gly Gly Asn Glu Phe
                645                 650                 655

Trp Gly Pro Trp Asn Phe Asn Pro Asn Thr Lys Leu Thr Ile Lys Ala
            660                 665                 670

Gly Thr Gln Glu Thr Ser Ser Thr Ala Ile Tyr Ser Gly Thr Met Pro
            675                 680                 685

Phe Ala Pro Ile Ala Ser Leu Ser Asp Tyr Ser Gln Ala Pro Leu Thr
            690                 695                 700

Ile Tyr Asn Ala Pro Thr Gly Pro Ser Ala Lys Pro Ala Val Ile Ala
705                 710                 715                 720

Phe Ile Arg Pro Gly Asn Trp Gly Ala Phe Phe Gly Leu Asp Thr Asp
                725                 730                 735

Asn Lys Leu Lys Trp Gly Gly Gly Ser Leu Gly Asn Ser Ser Met Glu
            740                 745                 750
```

```
Ile Ala Asp Ser Ser Asn Ile Met Asn Leu Trp Ala Ala Asn Pro Thr
            755                 760                 765
Ala Pro Thr Trp Asn Gly Gln Thr Val Trp Arg Ser Gly Asn Phe Asp
            770                 775                 780
Pro Ala Thr Lys Val Asp Leu Asn Ala Pro Asn Ala Thr Asn Gly Asn
785                 790                 795                 800
Met Ile Phe Asn Arg Ile Ala Gly Thr Gly Ser Gly Ile Ala Ser Ser
            805                 810                 815
Gly Arg Val Gly Ala Ile Ser Leu Gln Asn Gly Ala Thr Ala Gly Ala
            820                 825                 830
Ala Ala Ala Val Thr Phe Glu Arg Gly Gly Gly Phe Phe Val Asn Phe
            835                 840                 845
Gly Leu Asp Thr Asp Asn Val Leu Lys Val Gly Gly Asn Leu Gly
            850                 855                 860
Ala Asn Ala Tyr Pro Val Ile His Ala Gly Asn Tyr Asn Ser Tyr Ile
865                 870                 875                 880
Asn Gln Ala Leu Val Gln Val Gly Leu Gly Val Gly Ser Tyr Ala
            885                 890                 895
Ala Leu Ala Val Tyr Asp Thr Ser Ala Pro Ala Ser Ser Val Gly Pro
            900                 905                 910
Gly Thr Ile Leu Asp Gly Ser Val Leu Phe Tyr Ser Ser Phe Asn Ala
            915                 920                 925
Asn Phe Arg Ser Gly Thr Lys Pro Thr Gly Thr Trp Arg Cys Met Gly
            930                 935                 940
Tyr Ile Leu Asn Arg Asp Gly Thr Asn Pro Asp Ser Ala Thr Leu Phe
945                 950                 955                 960
Gln Arg Val Thr

<210> SEQ ID NO 28
<211> LENGTH: 963
<212> TYPE: PRT
<213> ORGANISM: Bacteriophage KPP12

<400> SEQUENCE: 28

Met Ile Thr Pro Glu Leu Ile Pro Ser Pro Phe Ala Ala Gln Gly Asp
1               5                   10                  15
Lys Asp Pro Ile Pro Gln Thr Ser Ser Thr Gly Phe Ala Asn Leu Arg
            20                  25                  30
Asp Gly Tyr Thr Pro Asp Tyr Glu Ile Ser Leu Ala Ser Asn Asn Pro
        35                  40                  45
Gln Ala Lys Ala Val Glu Arg Lys Ile Gln Asn Gln Leu Phe Phe Ile
    50                  55                  60
Ala Thr Gln Asn Ala Gln Ala Trp Gln Arg Gln Met Ala Pro Pro Trp
65                  70                  75                  80
Phe Gln Gly Met Pro Gly Gly Tyr Glu Gln Asn Ala Glu Val Val Arg
                85                  90                  95
Val Gly Asn Asp Gly Ile Met Arg Arg Tyr Arg Ser Met Val Asn Ala
            100                 105                 110
Asn Ala Ser Asp Pro Leu Ser Ser Thr Thr Trp Glu Glu Gln Pro Ala
        115                 120                 125
Trp Ser Ala Met Arg Ser Asn Ile Pro Met Pro Ala Gly Gly Pro Gly
    130                 135                 140
Leu Ser Ser Gly Gly Glu Val Ile Thr Thr Gly Arg Asn Phe Asn Asp
145                 150                 155                 160
```

-continued

```
Leu Leu Asn Gly Thr Trp Glu Phe Phe Ser Asp Ser Val Val Ile Ala
            165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
            195                 200                 205

Gln Arg Tyr Thr Asp Arg Val Gly Asn Val Ala Leu Arg Gly Leu Asn
            210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
            245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Ser Thr
            275                 280                 285

Ile Asn Val Ser Gly Leu Gly Ala Lys Ala Ile Val Gly Ala Ala Asn
            290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
            325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
385                 390                 395                 400

Phe His Phe Asn Asn Asn Arg Ala Lys Asp Phe Asp Tyr Arg Phe Ile
            405                 410                 415

Ser Glu Ala Asp Gly Ser Met Ala Phe Tyr Ser Arg Gln Gly Ser Ala
            420                 425                 430

Gly Pro Thr Gln Asp Ile Leu Phe Ser Arg Ser Asn Val Thr Phe Leu
            435                 440                 445

Gln Pro Arg Leu Asp Val Ala Lys Asn Leu Ala Tyr Ile Ala Asn Ser
            450                 455                 460

Gly Ser Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
            485                 490                 495

Asn Thr Thr Asn Pro Asp Gly Ser Tyr Arg Ser Gln Ile Met Arg Trp
            500                 505                 510

Asp Trp Ala Ser Thr Asn Val Ile Phe Asn Asn Arg Pro Leu Phe Ala
            515                 520                 525

Gly Gln Tyr Thr Pro Trp Asp Ser Gly Asn Phe Asp Pro Ser Thr Lys
            530                 535                 540

Leu Thr Val Asn Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Ser Ser
            565                 570                 575

Thr Thr Ala Ser Tyr Gly Asn Ala Ala Leu Gln Ile Phe Gly Lys Gly
```

```
            580                 585                 590
Gly Gly Glu Pro Ala Ala Leu Tyr Phe Asp Asn Ser Gln Thr Gly Trp
            595                 600                 605
Tyr Leu Gly Met Asp Lys Asp Gly Gln Leu Lys Arg Ala Gly Trp Ser
            610                 615                 620
Leu Gly Asn Asn Ala Tyr Val Ile Thr Asp Glu Ser Asn Ile Arg Phe
625                 630                 635                 640
His Val Asn Ser Met Ala Gly Thr Pro Val Trp Gly Gly Asn Glu Phe
                645                 650                 655
Trp Gly Ser Trp Asn Phe Asn Pro Asn Thr Lys Leu Thr Ile Lys Ala
            660                 665                 670
Gly Thr Gln Glu Thr Ser Thr Ala Ile Phe Ser Glu Thr Met Pro
            675                 680                 685
Phe Ala Pro Ile Ala Ser Leu Ser Asp Tyr Ser Gln Ala Pro Leu Thr
            690                 695                 700
Ile Tyr Asn Ala Pro Thr Gly Pro Ser Ala Lys Pro Ala Val Ile Ala
705                 710                 715                 720
Phe Ile Arg Pro Gly Asn Trp Gly Ala Phe Phe Gly Leu Asp Thr Asp
                725                 730                 735
Asn Lys Leu Lys Trp Gly Gly Ser Leu Gly Asn Ser Ser Arg Glu
            740                 745                 750
Ile Ala Asp Ser Arg Asn Ile Met Asn Leu Trp Ala Ala Asn Pro Thr
            755                 760                 765
Ala Pro Thr Trp Asn Gly Gln Thr Val Trp Arg Ser Gly Asn Phe Asp
            770                 775                 780
Pro Ala Thr Lys Val Asp Leu Asn Ala Pro Asn Ala Thr Asn Gly Asn
785                 790                 795                 800
Met Ile Phe Asn Arg Ile Ala Gly Thr Gly Ser Gly Ile Ala Ser Ser
                805                 810                 815
Gly Arg Val Gly Ala Ile Ser Leu Gln Asn Gly Ala Thr Ala Gly Ala
            820                 825                 830
Ala Ala Ala Val Thr Phe Glu Arg Gly Gly Phe Phe Val Asn Phe Gly
            835                 840                 845
Leu Asp Thr Asp Asn Val Leu Lys Val Gly Gly Asn Leu Gly Ala
            850                 855                 860
Asn Ala Tyr Pro Val Ile His Ala Gly Asn Tyr Asn Ser Tyr Ile Asn
865                 870                 875                 880
Gln Ala Leu Val Gln Val Gly Leu Gly Gly Val Gly Ser Tyr Ala Ala
                885                 890                 895
Leu Ala Val Tyr Asp Thr Ser Ala Pro Ala Ser Ser Val Gly Pro Gly
            900                 905                 910
Thr Ile Leu Asp Gly Ser Val Leu Phe Tyr Ser Ser Phe Asp Ala Asn
            915                 920                 925
Phe Arg Ser Gly Thr Lys Pro Thr Gly Thr Trp Arg Cys Met Gly Tyr
            930                 935                 940
Val Leu Asn Arg Asp Gly Thr Asn Pro Asp Ser Ala Ala Leu Phe Gln
945                 950                 955                 960
Arg Val Thr
```

<210> SEQ ID NO 29
<211> LENGTH: 962
<212> TYPE: PRT
<213> ORGANISM: Bacteriophage JG024

<400> SEQUENCE: 29

```
Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Thr Asn Ile Pro Met Pro Ala Gly Gly Pro Gly
    130                 135                 140

Leu Ser Ser Gly Gly Glu Val Ile Thr Thr Gly Arg Asn Phe Asn Glu
145                 150                 155                 160

Leu Leu Asn Gly Thr Trp Glu Phe Phe Ser Asp Ala Ile Val Val Ala
                165                 170                 175

Ser Gln Asn Ala Pro Val Tyr Pro Ala Ser Gly Ala Ala Ala Gly
            180                 185                 190

Met Leu Glu Ala Lys Ser Trp Val Ser Gly Ser Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln His Gly Arg Val Thr Tyr Gly Thr Ala Gly Pro Ala Asn Ala
                245                 250                 255

Tyr Thr Leu Thr Leu Val Pro Gln Ile Gln Gly Gly Leu Val Asp Gly
            260                 265                 270

Met Ile Leu Arg Val Lys Phe Asn Thr Met Asn Thr Gly Ala Thr Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Glu Ser Gln Lys Leu Thr Glu Val Asp
        355                 360                 365

Trp Thr Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415
```

```
Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
            435                 440                 445

Gln Pro Arg Leu Asp Val Ala Lys Asn Leu Ala Tyr Ile Ala Asn Ser
450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
            500                 505                 510

Asp Trp Ala Ser Thr Asn Val Ile Phe Asn Asn Arg Pro Leu Phe Ala
            515                 520                 525

Gly Gln Tyr Thr Pro Trp Asp Ser Gly Asn Phe Asp Pro Ser Thr Lys
            530                 535                 540

Leu Thr Val Ser Ala Thr Asn Gln Ile Ser Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Gln Ile Phe Gly Lys Gly
                580                 585                 590

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
            610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
                645                 650                 655

Trp Gly Pro Trp Asn Phe Asp Pro Asn Leu Lys Leu Thr Leu Asn Ala
            660                 665                 670

Phe Asn Asp Ser Ser Tyr Thr Arg Met Thr Asn Ser Gly Ala Lys Asp
            675                 680                 685

Val Gly Ile Ala Ser Met Thr Ser Tyr Ala Asp Ala Ala Met Ser Phe
690                 695                 700

Phe Asn Tyr Glu Ala Ser Asn Pro Thr Gly Pro Arg Ala Ala Val Ile
705                 710                 715                 720

Ser Phe Val Arg Asn Gly Ser Arg Gly Val Leu Phe Gly Leu Asp Ser
                725                 730                 735

Asp Asn Lys Leu Lys Trp Gly Tyr Ser Leu Gly Ala Val Ala Phe
            740                 745                 750

Glu Ile Ala Asp Ser Asn Asn Leu Met Ser Leu Trp Ser Ser His Ala
            755                 760                 765

Ala Ala Pro Asn Trp Asn Gly Gln Thr Ile Trp Arg Ser Gly Asn Phe
            770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830
```

```
Ala Ile Thr Phe His Ser Pro Gln Lys Tyr Gln Val Asn Phe Gly Leu
            835                 840                 845

Asp Ala Asp Asn Val Val Lys Ile Gly Gly Thr Met Gly Gly Val
850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Val Gly Ser Tyr Ala Ile Leu
                885                 890                 895

Ala Val Leu Asp Thr Ser Ala Pro Ala Ala Ser Ile Ala Pro Gly Thr
                900                 905                 910

Ile Met Asp Ser Ser Lys Leu Phe Tyr Ser Ser Cys Asp Ser Thr Tyr
            915                 920                 925

Arg Ser Ser Ala Ser Pro Thr Gly Thr Trp Arg Cys Met Gly Tyr Val
930                 935                 940

Tyr Asn Arg Asp Ser Thr Asn Gly Asp Ser Ala Ser Leu Phe Gln Arg
945                 950                 955                 960

Val Thr

<210> SEQ ID NO 30
<211> LENGTH: 962
<212> TYPE: PRT
<213> ORGANISM: Bacteriophage PTP92

<400> SEQUENCE: 30

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
            35                  40                  45

Gln Ala Lys Ala Val Glu Arg Lys Ile Gln Asn Gln Leu Phe Phe Ile
50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Thr Asn Ile Pro Met Pro Ala Gly Gly Pro Gly
130                 135                 140

Leu Ser Ser Gly Gly Glu Val Ile Thr Thr Gly Arg Asn Phe Asn Glu
145                 150                 155                 160

Leu Leu Asn Gly Thr Trp Glu Phe Phe Ser Asp Ala Ile Val Val Ala
                165                 170                 175

Ser Gln Asn Ala Pro Val Tyr Pro Ser Ala Gly Ala Ala Gly
            180                 185                 190

Met Leu Glu Ala Lys Ser Trp Val Ser Gly Ser Asn Thr Phe Cys Val
            195                 200                 205

Gln Arg Tyr Thr Asp Arg Val Gly Asn Val Ala Val Arg Gly Leu Asn
        210                 215                 220

Ala Gly Ala Trp Thr Asn Trp Met Tyr Ala Val Asn Val Met Ala Leu
225                 230                 235                 240
```

-continued

Gln His Gly Arg Val Thr Tyr Gly Thr Ala Gly Pro Ala Asn Ala
            245                 250                 255

Tyr Thr Leu Thr Leu Val Pro Gln Ile Gln Gly Gly Leu Val Asp Gly
            260                 265                 270

Met Ile Leu Arg Val Lys Phe Asn Thr Met Asn Thr Gly Ala Thr Thr
            275                 280                 285

Ile Asn Val Ser Gly Leu Gly Ala Lys Ala Ile Val Gly Ala Ala Asn
            290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Glu Ser Gln Lys Leu Thr Glu Val Asp
            355                 360                 365

Trp Thr Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
            435                 440                 445

Gln Pro Arg Leu Asp Val Ala Lys Asn Leu Ala Tyr Ile Ala Asn Ser
450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
            500                 505                 510

Asp Trp Ala Ser Thr Asn Val Ile Phe Asn Asn Arg Pro Leu Phe Ala
            515                 520                 525

Gly Gln Tyr Thr Pro Trp Asp Ser Gly Asn Phe Asp Pro Ser Thr Lys
            530                 535                 540

Leu Thr Val Ser Ala Thr Asn Gln Ile Ser Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Gln Ile Phe Gly Lys Gly
            580                 585                 590

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
            610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
                645                 650                 655

Trp Gly Pro Trp Asn Phe Asp Pro Asn Leu Lys Leu Thr Leu Asn Ala

```
                    660                 665                 670
Phe Asn Asp Ser Ser Tyr Thr Arg Met Thr Asn Ser Gly Ala Lys Asp
                675                 680                 685

Val Gly Ile Ala Ser Met Thr Ser Tyr Ala Asp Ala Ala Met Ser Phe
            690                 695                 700

Phe Asn Tyr Glu Ala Ser Asn Pro Thr Gly Pro Arg Ala Ala Val Ile
705                 710                 715                 720

Ser Phe Val Arg Asn Gly Ser Arg Gly Val Leu Phe Gly Leu Asp Ser
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
            755                 760                 765

Ala Ala Pro Asn Trp Asn Gly Gln Thr Ile Trp Arg Ser Gly Asn Phe
            770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
            835                 840                 845

Asp Ala Asp Asn Val Val Lys Ile Gly Gly Gly Thr Met Gly Gly Val
850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Ala Ile Leu
                885                 890                 895

Ala Val Leu Asp Thr Ser Ala Pro Ala Ala Ser Ile Ala Pro Gly Thr
            900                 905                 910

Ile Met Asp Ser Ser Lys Leu Phe Tyr Ser Ser Cys Asp Ser Thr Tyr
            915                 920                 925

Arg Ser Ser Ala Ser Pro Thr Gly Thr Trp Arg Cys Met Gly Tyr Val
            930                 935                 940

Tyr Asn Arg Asp Ser Thr Asn Gly Asp Ser Ala Ser Leu Phe Gln Arg
945                 950                 955                 960

Val Thr

<210> SEQ ID NO 31
<211> LENGTH: 962
<212> TYPE: PRT
<213> ORGANISM: Bacteriophage NH4

<400> SEQUENCE: 31

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
```

```
                65                  70                  75                  80
        Phe Gln Gly Met Pro Gly Gly Tyr Glu Arg Asn Ala Glu Val Val Arg
                            85                  90                  95

Val Gly Asn Asp Gly Ile Met Arg Arg Tyr Arg Ser Met Val Asn Ala
                            100                 105                 110

Asn Ala Ser Asp Pro Leu Ser Thr Thr Trp Glu Gln Pro Ala
                            115                 120                 125

Trp Ser Val Met Arg Thr Asn Ile Pro Met Pro Ala Gly Gly Pro Gly
                130                 135                 140

Leu Ser Ser Gly Gly Glu Val Ile Thr Thr Gly Arg Asn Phe Asn Glu
        145                 150                 155                 160

Leu Leu Asn Gly Thr Trp Glu Phe Phe Ser Asp Ala Ile Val Val Ala
                            165                 170                 175

Ser Gln Asn Ala Pro Val Tyr Pro Ala Ser Ala Gly Ala Ala Ala Gly
                            180                 185                 190

Met Leu Glu Ala Lys Ser Trp Val Ser Gly Ser Asn Thr Phe Cys Val
                            195                 200                 205

Gln Arg Tyr Thr Asp Arg Val Gly Asn Val Ala Val Arg Gly Leu Asn
                            210                 215                 220

Ala Gly Ala Trp Thr Asn Trp Met Tyr Ala Val Asn Val Met Ala Leu
        225                 230                 235                 240

Gln His Gly Arg Val Thr Tyr Gly Thr Ala Ala Gly Pro Ala Asn Ala
                            245                 250                 255

Tyr Thr Leu Thr Leu Val Pro Gln Ile Gln Gly Gly Leu Val Asp Gly
                            260                 265                 270

Met Ile Leu Arg Val Lys Phe Asn Thr Met Asn Thr Gly Ala Thr Thr
                    275                 280                 285

Ile Asn Val Ser Gly Leu Gly Ala Lys Ala Ile Val Gly Ala Ala Asn
                    290                 295                 300

Phe Pro Leu Thr Gly Gly Glu Leu Gly Gln Gly Leu Ile Ala Glu Leu
        305                 310                 315                 320

Val Phe Asp Ala Ala Gly Asp Arg Trp Arg Ile Leu Ala Gly Ala Pro
                            325                 330                 335

Arg Ile Gln Val Gly Asn Ala Asp Gln Asp Tyr Gln Ala Pro Ser Trp
                            340                 345                 350

Lys Gln Val Lys Asp Tyr Val Ala Ser Gln Lys Leu Thr Glu Val Asp
                    355                 360                 365

Trp Thr Asp Val Val Asn Lys Pro Asn Val Ala Ile Gln Asp Thr Thr
            370                 375                 380

Pro Trp Phe Ala Asn Leu Glu Leu Ser Asp Ala Arg Pro Phe Ile Asp
        385                 390                 395                 400

Phe His Phe Asn Ser Asn Arg Ala Lys Asp Phe Asp Tyr Arg Leu Ile
                            405                 410                 415

Ser Glu Ala Asp Gly Ser Leu Ala Phe Tyr Ser Arg Gln Gly Ser Ala
                            420                 425                 430

Gly Pro Thr Gln Asp Ile Leu Phe Asn Arg Asn Ser Val Thr Phe Phe
                    435                 440                 445

Gln Pro Arg Leu Asp Val Ala Lys Asn Leu Ala Tyr Ile Ala Asn Ser
                    450                 455                 460

Gly Pro Leu Trp Gln Asn Thr Thr Ala Asp Gln Pro Gly Trp Lys Phe
        465                 470                 475                 480

Thr Phe Ala Gln Gly Val Asp Ala Asn Asn Asn Ala Val Ile Ala Val
                            485                 490                 495
```

```
Asn Thr Thr Asn Pro Asp Gly Ser Tyr Arg Ser Gln Val Met Arg Trp
                500             505                 510
Asp Trp Ala Ser Thr Asn Val Ile Phe Asn Asn Arg Pro Leu Phe Ala
        515                 520                 525
Gly Gln Tyr Thr Pro Trp Asp Ser Gly Asn Phe Asp Pro Ser Thr Lys
        530                 535                 540
Leu Thr Val Ser Ala Thr Asn Gln Ile Ala Gly Pro Thr Gly Ile Arg
545                 550                 555                 560
Asn Thr Asn Gly Asn Thr Gly Asn Met Asn Thr Trp Gly Ser Gly Ser
                565                 570                 575
Thr Thr Ala Ser Tyr Gly Asn Ala Ala Ile Gln Ile Phe Gly Lys Gly
                580                 585                 590
Gly Gly Glu Pro Ala Ala Ile Tyr Phe Asp Asn Ser Gln Thr Gly Trp
                595                 600                 605
Tyr Leu Gly Met Asp Lys Asp Gly Gln Leu Lys Arg Ala Gly Trp Ser
        610                 615                 620
Leu Gly Asn Asn Ser Tyr Val Ile Thr Asp Glu Ser Asn Ile Arg Thr
625                 630                 635                 640
His Ile Asn Thr Met Ala Ala Arg Pro Ile Trp Gly Asn Val Glu Phe
                645                 650                 655
Trp Gly Pro Trp Asn Phe Asn Pro Asn Thr Lys Leu Thr Leu Gly Ser
                660                 665                 670
Phe Asn Asp Ser Gln His Thr Arg Met Val Asn Ser Ala Ala Lys Asp
        675                 680                 685
Val Gly Ile Ala Ser Met Thr Ser Tyr Ala Asp Ala Ala Met Ser Phe
        690                 695                 700
Phe Asn Tyr Glu Ala Ser Thr Pro Thr Gly Asn Arg Ala Ala Val Ile
705                 710                 715                 720
Ser Phe Val Arg Asn Gly Ala Arg Gly Val Leu Phe Gly Leu Asp Thr
                725                 730                 735
Asp Asn Lys Leu Lys Trp Gly Gly Tyr Ser Leu Gly Ala Val Ala Phe
                740                 745                 750
Glu Ile Ala Asp Ser Asn Asn Leu Met Ser Leu Trp Ser Ser His Ala
        755                 760                 765
Ala Ala Pro Asn Trp Asn Gly Gln Thr Ile Trp Arg Ser Gly Asn Phe
        770                 775                 780
Asn Pro Asp Thr Lys Ala Thr Leu Ala Ala Arg Asn Thr Thr Ser Ser
785                 790                 795                 800
Pro Thr Ile Phe Ser Tyr Gly Ala Ser Gly Ile Ala Ser Thr Gly Gln
                805                 810                 815
Val Gly Ala Leu Val Val Glu Asn Asn Ser Val Thr Asn Thr Ala Ala
                820                 825                 830
Ala Ile Thr Phe His Ser Pro Gln Lys Tyr Gln Val Asn Phe Gly Leu
        835                 840                 845
Asp Ala Asp Asn Val Val Lys Ile Gly Gly Gly Thr Met Gly Gly Val
        850                 855                 860
Ala Tyr Pro Ile Ile His Ser Gly Asn Tyr Asn Asn Tyr Ile Asn Gln
865                 870                 875                 880
Ala Leu Val Gln Val Gly Leu Gly Gly Val Gly Ser Tyr Ala Ile Leu
                885                 890                 895
Ala Val Leu Asp Thr Ser Ala Pro Ala Ala Ser Ile Ala Pro Gly Thr
            900                 905                 910
```

```
Ile Met Asp Ser Ser Lys Leu Phe Tyr Ser Ser Cys Asp Ser Thr Tyr
            915                 920                 925

Arg Ser Ser Ala Arg Pro Thr Gly Thr Trp Arg Cys Met Gly Tyr Val
        930                 935                 940

Tyr Asn Arg Asp Ser Thr Asn Gly Asp Ser Ala Ser Leu Phe Gln Arg
945                 950                 955                 960

Val Thr

<210> SEQ ID NO 32
<211> LENGTH: 962
<212> TYPE: PRT
<213> ORGANISM: Bacteriophage 14-1

<400> SEQUENCE: 32

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Ser Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Ile Ala
                165                 170                 175

Ser Gln Asn Ala Pro Val Tyr Pro Ala Ser Gly Ala Ala Ala Gly
            180                 185                 190

Met Leu Glu Ala Lys Ser Trp Ile Ser Arg Ser Asn Thr Phe Cys Val
        195                 200                 205

Gln Arg Tyr Thr Asp Arg Val Gly Asn Val Ala Val Arg Gly Leu Asn
    210                 215                 220

Ala Gly Glu Trp Thr Asn Trp Met Tyr Ala Val Asn Val Met Ala Leu
225                 230                 235                 240

Gln Gln Gly Arg Val Thr Tyr Gly Val Ala Ala Gly Pro Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Val Asn Thr Gly Ala Ser Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320
```

```
Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Thr Asp Val Val Asn Lys Pro Asn Val Ala Ile Gln Asp Thr Thr
370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
        435                 440                 445

Gln Pro Arg Leu Asp Val Ala Lys Asn Leu Ala Tyr Ile Ala Asn Ser
    450                 455                 460

Gly Pro Ile Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
            500                 505                 510

Asp Trp Ala Ser Thr Asn Val Ile Phe Asn Asp Arg Pro Leu Phe Ala
        515                 520                 525

Gly Gln Tyr Thr Pro Trp Asp Ser Gly Asn Phe Asp Pro Ser Thr Lys
    530                 535                 540

Leu Thr Val Ser Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Gln Ile Phe Gly Lys Gly
            580                 585                 590

Gly Gly Glu Pro Ala Ala Ile Tyr Phe Asp Asn Ser Gln Thr Gly Trp
        595                 600                 605

Tyr Leu Gly Met Asp Lys Asp Gly Arg Leu Lys Arg Ala Gly Trp Ser
    610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
                645                 650                 655

Trp Gly Pro Trp Asn Phe Asp Pro Asn Leu Lys Leu Thr Leu Asn Ala
            660                 665                 670

Phe Asn Asp Ser Ser Tyr Thr Arg Met Thr Asn Ser Gly Ala Lys Asp
        675                 680                 685

Val Gly Ile Ala Ser Met Thr Ser Tyr Ala Asp Ala Ala Met Ser Phe
    690                 695                 700

Phe Asn Tyr Glu Ala Ser Asn Pro Thr Gly Pro Arg Ala Ala Val Ile
705                 710                 715                 720

Ser Phe Val Arg Asn Gly Ser Arg Gly Val Leu Phe Gly Leu Asp Ser
                725                 730                 735

Asp Asn Lys Leu Lys Trp Gly Gly Tyr Ser Leu Gly Ala Val Ala Phe
```

```
                740                 745                 750
Glu Ile Ala Asp Ser Asn Asn Leu Met Ser Leu Trp Ser Ser His Ala
            755                 760                 765

Ala Ala Pro Asn Trp Asn Gly Gln Thr Ile Trp Arg Ser Gly Asn Phe
        770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
        835                 840                 845

Asp Ala Asp Asn Val Val Lys Ile Gly Gly Thr Met Gly Gly Val
            850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Gly Ile Phe
                885                 890                 895

Ala Val Leu Asp Asn Ala Ala Pro Ile Ala Thr Val Gln Pro Gly Val
            900                 905                 910

Val Val Asp Gly Ser Ile Leu Ile Tyr Ser Ser Cys Ala Ala Asn Tyr
        915                 920                 925

Asn Ser Gly Gln Arg Pro Ala Gly Thr Trp Arg Cys Met Gly Tyr Val
    930                 935                 940

Val Asn Arg Asp Ala Asn Thr Pro Asp Ser Ala Thr Leu Phe Gln Arg
945                 950                 955                 960

Val Thr

<210> SEQ ID NO 33
<211> LENGTH: 962
<212> TYPE: PRT
<213> ORGANISM: Bacteriophage PTP47

<400> SEQUENCE: 33

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
                20                  25                  30

Asp Gly Tyr Thr Pro Asp Tyr Glu Ile Ser Leu Ala Ser Asn Asn Pro
            35                  40                  45

Gln Ala Lys Ala Val Glu Arg Lys Ile Gln Asn Gln Leu Phe Phe Ile
        50                  55                  60

Ala Thr Gln Asn Ala Gln Ala Trp Gln Arg Gln Met Ala Pro Pro Trp
65                  70                  75                  80

Phe Gln Asp Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Gln Pro Ala
        115                 120                 125

Trp Ser Ala Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
```

```
                145                 150                 155                 160
        Leu Leu Asn Gly Thr Trp Glu Phe Phe Ser Asp Ser Val Val Ile Ala
                        165                 170                 175
        Ser Gln Asn Ala Pro Val Tyr Pro Ala Ser Ala Gly Ala Ala Ala Gly
                        180                 185                 190
        Met Leu Glu Ala Lys Ser Trp Val Ser Gly Ala Asn Thr Phe Cys Val
                        195                 200                 205
        Gln Arg Tyr Thr Asp Arg Val Gly Asn Val Ala Val Arg Gly Leu Asn
                        210                 215                 220
        Ala Gly Ala Trp Thr Asn Trp Met Tyr Ala Val Asn Val Met Ala Leu
        225                 230                 235                 240
        Gln Gln Gly Arg Val Thr Tyr Gly Val Ala Ala Gly Ser Ala Asn Ala
                        245                 250                 255
        Tyr Thr Leu Thr Leu Val Pro Gln Leu Gln Gly Gly Leu Val Asp Gly
                        260                 265                 270
        Met Ile Leu Arg Val Lys Phe Asn Thr Met Asn Thr Gly Ala Thr Thr
                        275                 280                 285
        Ile Asn Val Ser Gly Leu Gly Ala Lys Ala Ile Val Gly Ala Ala Asn
                        290                 295                 300
        Phe Pro Leu Thr Gly Gly Glu Leu Gly Gln Gly Leu Ile Ala Glu Leu
        305                 310                 315                 320
        Val Phe Asp Ala Ala Gly Asp Arg Trp Arg Ile Leu Ala Gly Ala Pro
                        325                 330                 335
        Arg Ile Gln Val Gly Asn Ala Asp Gln Asp Tyr Gln Ala Pro Ser Trp
                        340                 345                 350
        Lys Gln Val Lys Asp Tyr Val Ala Ser Gln Lys Leu Thr Glu Val Asp
                        355                 360                 365
        Trp Ala Asp Val Val Asn Lys Pro Asn Val Ala Ile Gln Asp Thr Thr
                        370                 375                 380
        Pro Trp Phe Ala Asn Leu Glu Leu Ser Asp Ala Arg Pro Phe Ile Asp
        385                 390                 395                 400
        Phe His Phe Asn Ser Asn Arg Ala Lys Asp Phe Asp Tyr Arg Leu Ile
                        405                 410                 415
        Ser Glu Ala Asp Gly Ser Leu Ala Phe Tyr Ser Arg Gln Gly Ser Ala
                        420                 425                 430
        Gly Pro Thr Gln Asp Ile Leu Phe Asn Arg Asn Ser Val Thr Phe Phe
                        435                 440                 445
        Gln Pro Arg Leu Asp Val Ala Lys Asn Leu Ala Tyr Ile Ala Asn Ser
                        450                 455                 460
        Gly Pro Leu Trp Gln Asn Thr Thr Ala Asp Gln Pro Gly Trp Lys Phe
        465                 470                 475                 480
        Thr Phe Ala Gln Gly Val Asp Ala Asn Asn Ala Val Ile Ala Val
                        485                 490                 495
        Asn Thr Thr Asn Pro Asp Gly Ser Tyr Arg Ser Gln Val Met Arg Trp
                        500                 505                 510
        Asp Trp Ala Ser Thr Asn Val Ile Phe Asn Asn Arg Pro Leu Phe Ala
                        515                 520                 525
        Gly Gln Tyr Thr Pro Trp Asp Ser Gly Asn Phe Asp Pro Ser Thr Lys
                        530                 535                 540
        Leu Thr Val Ser Ala Thr Asn Gln Ile Ala Gly Pro Thr Gly Ile Arg
        545                 550                 555                 560
        Asn Thr Asn Gly Asn Thr Gly Asn Met Asn Thr Trp Gly Ser Gly Ser
                        565                 570                 575
```

Thr Thr Ala Ser Tyr Gly Asn Ala Ala Ile Arg Ile Phe Gly Lys Gly
            580                 585                 590

Gly Gly Glu Pro Ala Ala Ile Tyr Phe Asp Asn Ser Gln Thr Gly Trp
        595                 600                 605

Tyr Leu Gly Met Asp Lys Asp Gly Gln Leu Lys Arg Ala Gly Trp Ser
610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
                645                 650                 655

Trp Gly Pro Trp Asn Phe Asn Pro Asn Thr Lys Leu Thr Leu Gly Ser
            660                 665                 670

Phe Asn Asp Gly Gln His Thr Arg Met Val Asn Ser Ala Ala Lys Asp
        675                 680                 685

Val Gly Ile Ala Ser Met Thr Ser Tyr Ala Asp Ala Ala Met Ser Phe
690                 695                 700

Phe Asn Tyr Glu Ala Ser Thr Pro Thr Gly Asn Arg Ala Ala Val Ile
705                 710                 715                 720

Ser Phe Val Arg Asn Gly Ala Arg Gly Val Leu Phe Gly Leu Asp Thr
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr His Val Asn Phe Gly Leu
        835                 840                 845

Asp Ala Asp Asn Val Val Lys Ile Gly Gly Gly Thr Met Gly Gly Val
850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Glu Val Gly Ser Tyr Gly Ile Phe
                885                 890                 895

Ala Val Leu Asp Tyr Ala Ala Pro Thr Ala Thr Val Arg Pro Gly Val
            900                 905                 910

Val Val Asp Gly Ser Ile Leu Ile Tyr Ser Ser Cys Ala Ala Asn Tyr
        915                 920                 925

Asn Ser Gly Gln Arg Pro Ala Gly Thr Trp Arg Cys Met Gly Tyr Val
930                 935                 940

Val Asn Arg Asp Ala Asn Thr Pro Asp Ser Ala Thr Leu Phe Gln Arg
945                 950                 955                 960

Val Thr

<210> SEQ ID NO 34
<211> LENGTH: 962
<212> TYPE: PRT

<213> ORGANISM: Bacteriophage SN

<400> SEQUENCE: 34

Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ser Asp Pro Leu Ser Ser Thr Thr Trp Glu Glu Gln Pro Ala
        115                 120                 125

Trp Ser Val Met Arg Ser Asn Ile Pro Met Pro Ala Gly Gly Pro Gly
130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Val Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Ser Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350

Lys Gln Val Lys Asp Tyr Val Ala Ser Gln Lys Leu Thr Glu Val Asp
        355                 360                 365

Trp Ala Asp Val Val Asn Lys Pro Asn Val Ala Ile Gln Asp Thr Thr
    370                 375                 380

Pro Trp Phe Ala Asn Leu Glu Leu Ser Asp Ala Arg Pro Phe Ile Asp
385                 390                 395                 400

```
Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
        435                 440                 445

Gln Pro Arg Leu Asp Val Ala Lys Asn Leu Ala Tyr Ile Ala Asn Ser
450                 455                 460

Gly Ser Leu Trp Gln Asn Thr Thr Ala Asp Gln Pro Gly Trp Lys Phe
465                 470                 475                 480

Thr Phe Ala Gln Gly Val Asp Ala Asn Asn Ala Val Ile Ala Val
                485                 490                 495

Asn Thr Thr Asn Pro Asp Gly Ser Tyr Arg Ser Gln Val Met Arg Trp
                500                 505                 510

Asp Trp Ala Ser Thr Asn Val Ile Phe Asn Asn Arg Pro Leu Phe Ala
            515                 520                 525

Gly Gln Tyr Thr Pro Trp Asp Ser Gly Asn Phe Asp Pro Ser Thr Lys
        530                 535                 540

Leu Thr Val Arg Ala Thr Asn Gln Ile Ala Gly Pro Thr Gly Ile Gln
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Ile Gln Ile Phe Gly Lys Gly
                580                 585                 590

Gly Gly Glu Pro Ala Ala Ile Tyr Phe Asp Asn Ser Gln Thr Gly Trp
            595                 600                 605

Tyr Leu Gly Met Asp Lys Asp Gly Gln Leu Lys Arg Ala Gly Trp Ser
        610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Gly Val Glu Phe
                645                 650                 655

Trp Gly Pro Trp Asn Phe Asn Pro Asn Thr Lys Leu Thr Leu Gly Ser
            660                 665                 670

Phe Asn Asp Ser Gln His Thr Arg Met Val Asn Ser Ala Ala Lys Asp
        675                 680                 685

Val Gly Ile Ala Ser Met Thr Ser Tyr Ala Asp Ala Ala Met Ser Phe
690                 695                 700

Phe Asn Tyr Glu Ala Ser Thr Pro Thr Gly Asn Arg Ala Ala Val Ile
705                 710                 715                 720

Ser Phe Val Arg Asn Gly Ala Arg Gly Val Leu Phe Gly Leu Asp Thr
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
```

```
                   820             825                 830
Ala Ile Thr Phe His Ser Pro Gln Lys Tyr Gln Val Asn Phe Gly Leu
            835                 840                 845

Asp Ala Asp Asn Val Val Lys Ile Gly Gly Gly Thr Met Gly Gly Val
        850                 855                 860

Ala Tyr Pro Ile Ile His Ser Gly Asn Tyr Asn Tyr Ile Asn Gln
865                 870                 875                 880

Ala Leu Val Gln Val Gly Leu Gly Gly Val Gly Ser Tyr Gly Ile Phe
                885                 890                 895

Ala Val Leu Asp Asn Ala Ala Pro Thr Ala Thr Val Gln Pro Gly Val
            900                 905                 910

Val Val Asp Gly Ser Ile Leu Ile Tyr Ser Ser Cys Ala Ala Asn Tyr
        915                 920                 925

Asn Ser Gly Gln Arg Pro Ala Gly Thr Trp Arg Cys Met Gly Tyr Val
            930                 935                 940

Val Asn Arg Asp Ala Asn Thr Pro Asp Ser Ala Thr Leu Phe Gln Arg
945                 950                 955                 960

Val Thr

<210> SEQ ID NO 35
<211> LENGTH: 2893
<212> TYPE: DNA
<213> ORGANISM: Bacteriophage PTP92

<400> SEQUENCE: 35
gtgatcacac cgaactgat  acccagtccg tttgctgcgc agggcgacaa agacccgatc      60
ccgcagacct cttccactgg ctttgccaac cttcgcgacg gctacacgcc ggactacgaa     120
atcagcctgg cgtcgaacaa cccgcaggcc aaagcggtcg agcgaaagat tcaaaaccaa     180
ctcttcttca tcgcgaccca gaacgcacag gcgtggcagc acaaatggc  gccgccgtgg     240 tttcagggca tgcctggcgg ctacgaacag aatgcagaag tcgtgcgcgt cggcaatgac     300
ggaatcatgc ggcgctatcg ctccatggtg aacgcaaacg ccagcgatcc tctcagcagt     360
accacctggg aagagcaacc cgcctggtca gttatgcgca ccaacatacc gatgccggct     420
ggcggccccg gtctgtcttc gggcggcgaa gtcatcacca ccggccgcaa cttcaatgaa     480
ttgctgaacg gaacctggga attttttctct gatgcaatcg tcgtggcctc tcagaacgct     540
ccggtgtatc cggcgtctgc cggcgcggca gcaggaatgc tggagcgaa  atcttgggtg     600 tccgggtcaa atacgttctg cgtccaacgc tacactgatc gcgtcggaaa cgtcgccgtg     660
cgcgggctca atgccggggc ctggaccaac tggatgtacg ctgtaaacgt catggccctc     720 caaacacggcc gtgtaaccta tggaaccgcg gccggtccgg cgaatgccta cccttgact       780 ctcgttccgc agatccaagg tggtttggta gatggcatga tccttcgggt caagttcaac     840
accatgaaca ccggcgctac taccatcaac gtctccggac tcggcgccaa agccatcgtc     900
ggcgcggcca acttccctct cactggcggc gaacttggcc aaggactcat cgctgagctt     960
gtcttcgacg cagcaggcga ccgctggagg attctggcag gcgcgccgcg catccaagtc    1020
ggcaacgccg atcaggacta ccaggcgccg agttggaagc aagttaaaga ctatgtcgag    1080
tcccaaaagc tcaccgaagt ggattggacg gatgtcgtca acaagccgaa cgtcgctatc    1140
caagatacaa cgccgtggtt cgccaatctg gagctgtccg atgctcggcc tttcatcgat    1200
ttccacttca acagcaatcg cgccaaagat tttgactatc ggctgatatc tgaagcagac    1260
ggatcgctgg ctttctattc gcggcagggg tctgctgggc ctacccagga catcctgttc    1320
```

```
aaccgaaatt ccgtgacttt cttccagccg cgactcgatg tggcgaaaaa cctcgcgtat    1380
atcgcgaact ctggcccact ttggcagaac accaccgccg atcagccggt tggaaattc     1440 acctttgcac aaggcgtgga cgcgaacaac aacgcggtga tcgcagtcaa taccaccaat    1500
ccggacggtt cctatcgttc acaggtcatg cgatgggact gggcgtccac gaacgtcata    1560
ttcaacaacc gtccgctctt cgccggtcaa tacacccctt gggattctgg gaacttcgat    1620
ccttccacca agttgacggt gagtgccacg aaccaaatct ccggcccaac cgggattcgg    1680
aataccaacg gcaacaccgg caacatgaac acctggggtt ccggctccac gacggcatcc    1740
tatggcaatg ctgccattca aatcttcgga aaaggggggcg gtgagcctgc cgcgatctat    1800
ttcgacaact cccagaccgg atggtatctg gcatggacaa ggatggacaa gctcaagcgg    1860
gccggctggt cgctcggcaa taactcctat gtgatcaccg acgaatccaa catccgaacc    1920
catatcaaca caatggctgc gcgcccgatt tgggggaatg tcgagttctg gggtccgtgg    1980
aacttcgatc cgaatcttaa actcactttg aacgctttca atgatagctc ataccaccag    2040
atgaccaaca gcggcgcgaa agacgttggt atcgcgtcca tgacgagtta tgctgatgcg    2100
gccatgtcat tcttcaacta tgaagcctcg aatccgaccg gccgcgcgc ggccgttatt     2160 tcgttcgtga aaatggatc gcgtggagtg ctattcggct tggattctga caacaagctg     2220
aaatggggcg gctattctct aggtgccgtc gcgttcgaga ttgccgactc caacaacctc    2280
atgagcctgt ggtcatccca cgctgccgcg ccgaactgga acgggcagac catctggagg    2340
tcgggaaact caacccgaga caccaaggcg actttggcag ctcgcaatac gacgtcatcc    2400
cctacaatat tcagttatgg ggcgtccgga atcgcatcaa ccggacaggt cggtgcgttg    2460
gttgtggaaa acaacagcgt caccaatacc gcagccgcca tcacgttcca ttcgccgcag    2520
aaatatcagg tcaacttcgg cctggatgcg gacaacgtgg taaagatcgg tggcggcaca    2580
atgggcggcg tagcatatcc catcatccac tccggcaact acaacaacta catcaaccag    2640
gcgctggttc aggtaggtct tggcggcgtc ggttcctacg cgatccttgc cgtattggac    2700
acctccgcgc cggcagcgtc cattgccccc ggaacgatca tggacagttc caagctgttc    2760
tattcgtcct gcgattcgac ctatcgcagc agcgccagtc cgacgggcac ctggcgctgc    2820
atggggtatg tgtataaccg agactccacc aacggcgact cggcatccct attccagcgg    2880
gtaacgtaaa atg                                                       2893
```

<210> SEQ ID NO 36
<211> LENGTH: 2893
<212> TYPE: DNA
<213> ORGANISM: Bacteriophage PTP47

<400> SEQUENCE: 36

```
gtgatcacac ccgaactgat ccccagtccg tttgccgctc agggcgataa agacccgatt      60
ccacaaacct cctccactgg cttcgcaaac cttcgcgacg gctatacgcc ggactacgaa     120
atcagcctgg cgtcgaacaa cccgcaggcc aaagcggtcg agcggaaaat tcaaaaccaa    180
ctcttcttca tcgcgaccca gaacgcacag gcgtggcagc gacaaatggc gccgccgtgg    240
tttcaggaca tgcctggcgg ctacgaacag aatgcagaag tcgtgcgcgt cggaaatgac    300
ggcataatgc ggcgttatcg ttccatggtg aatgccaatg cgagcgaccc tctcagcagc    360
acgacttggg aagaacaacc cgcatggtcg gcgatgcgct ccaacatccc gatgccggcc    420
ggaggcccag gcctatcttc tggcggagaa gtcatcacga ccggccgcaa cttcaacgac    480
```

```
ctgttaaatg ggacgtggga gttcttctct gattcagtgg ttatcgcttc tcagaatgcc    540
cccgtatatc cggcttccgc tggtgccgct gctggcatgt tggaggcgaa atcttgggtg    600
tccggagcca atacgttctg cgtccaacgc tacactgatc gcgtcgggaa cgtcgctgtg    660
cgcgggctta atgccggagc gtggaccaac tggatgtatg cggtaaacgt catggccctt    720
caacaaggtc gggtcaccta tggagtcgcg gccggatcgg cgaacgctta cacgttgacg    780
ctagttccgc agctccaagg tggtttggta gatggcatga tccttcgggt caagttcaac    840
accatgaaca ccggcgctac taccatcaac gtctccggac tcggcgccaa agccatcgtc    900
ggcgcggcca acttccctct caccggcggc gaacttggcc aaggactcat cgctgagctt    960
gtattcgacg cagcaggcga ccgctggaga atcctcgcag gcgcgccacg catccaagtt   1020
ggcaacgccg atcaagatta ccaggccccc agctggaaac aggtgaagga ttacgtcgcg   1080
tcccaaaagc tgactgaagt ggactgggct gacgtcgtca acaagccgaa cgtcgctatc   1140
caagacacca cgccgtggtt cgccaatctg gagctgtccg atgctcggcc tttcatcgat   1200
ttccacttca acagcaatcg cgccaaagat tttgactatc ggctgatatc tgaagcagac   1260
ggatcgctgg ctttctattc gcggcagggg tctgctgggc ctacccagga catcctgttc   1320
aaccgaaatt ccgtgacttt cttccagccg cgactcgatg ttgcgaaaaa cctcgcgtat   1380
atcgcgaact ctggcccccct ttggcagaac accaccgccg atcagcccgg ttggaaattc   1440
accttkgcac aaggcgtgga cgcgaacaac aacgcggtga tcgcagtcaa taccaccaat   1500
ccggacggtt cctatcgttc acaggtcatg cgatgggact gggcgtccac gaacgtcata   1560
ttcaacaacc gtccgctctt cgccggtcaa tacaccccctt gggattctgg gaacttcgat   1620
ccttccacca agttgacggt gagtgccacg aaccaaatcg ccgcccaac cgggattcgg   1680 aataccaacg gcaacaccgg caacatgaac acctggggtt ccggctccac gacggcatcc   1740
tatggcaatg ctgccattcg aatcttcgga aaaggggcg gtgagcctgc cgcgatctat   1800
ttcgacaact cccagaccgg atggtatctg ggcatggaca aggatggaca gctcaagcgg   1860
gccggctggt cgctcggcaa taactcctat gtgatcaccg acgaatccaa catccgaacc   1920
catatcaaca caatggctgc gcgcccgatt tgggggaatg tcgagttctg gggtccgtgg   1980
aacttcaatc ctaacacgaa gttgacgctt ggctcattca atgacggcca gcataccagg   2040
atggtcaaca gcgccgcgaa ggatgtagga attgcgtcca tgacgagcta tgcggacgcg   2100
gctatgtcgt tcttcaacta tgaggcttcg acgccgaccg ggaatcgtgc tgctgtaatt   2160
tcgtttgttc gtaacggggc acgaggcgtt ctgttcggcc tggacacgga caacaagctg   2220
aaatggggcg gctattctct aggtgccgtc gcgttcgaga ttgccgactc caacaacctc   2280
atgagcctgt ggtcatccca cgctgccgcg ccgaactgga acgggcagac catctggagg   2340
tcgggaaact tcaacccaga caccaaggcg actttggcag ctcgcaatac gacgtcatcc   2400
cctacaatat tcagttatgg ggcgtccgga atcgcatcaa ccggacaggt cggtgcgttg   2460
gttgtggaaa acaacagcgt caccaatacc gcagccgcca tcacgttcca ttcgccgcag   2520
aaatatcatg tcaacttcgg cctggatgcg gacaacgtgg taaagatcgg tggcggcaca   2580
atgggcggcg tagcatatcc catcatccac tccggcaact acaacaacta catcaaccag   2640
gcgctggttc aggtgggtct tggcgaagtc ggttcctatg gcatctttgc ggttctggac   2700
tatgccgctc caaccgcgac cgttcgaccg ggagtggttg tggacggttc cattctcatc   2760
tactcgtctt gcgccgcaaa ctacaatagc ggtcaaaggc ctgccggaac ttggcgctgc   2820
atgggatatg tagtcaaccg ggatgccaac actcctgact ccgcgaccct tttccagcga   2880
```

```
gtgacgtaaa atg                                                      2893
```

<210> SEQ ID NO 37
<211> LENGTH: 962
<212> TYPE: PRT
<213> ORGANISM: Artificial Sequence
<220> FEATURE:
<223> OTHER INFORMATION: hybrid: PTP92, PTP47, Phi33

<400> SEQUENCE: 37

```
Met Ile Thr Pro Glu Leu Ile Pro Ser Pro Phe Ala Ala Gln Gly Asp
1               5                   10                  15

Lys Asp Pro Ile Pro Gln Thr Ser Ser Thr Gly Phe Ala Asn Leu Arg
            20                  25                  30

Asp Gly Tyr Thr Pro Asp Tyr Glu Ile Ser Leu Ala Ser Asn Asn Pro
        35                  40                  45

Gln Ala Lys Ala Val Glu Arg Lys Ile Gln Asn Gln Leu Phe Phe Ile
    50                  55                  60

Ala Thr Gln Asn Ala Gln Ala Trp Gln Arg Gln Met Ala Pro Pro Trp
65                  70                  75                  80

Phe Gln Gly Met Pro Gly Gly Tyr Glu Gln Asn Ala Glu Val Val Arg
                85                  90                  95

Val Gly Asn Asp Gly Ile Met Arg Arg Tyr Arg Ser Met Val Asn Ala
            100                 105                 110

Asn Ala Ile Asp Pro Leu Ser Ser Thr Thr Trp Glu Glu Gln Pro Ala
        115                 120                 125

Trp Ser Val Met Arg Ser Asn Ile Pro Met Pro Ala Gly Gly Pro Gly
    130                 135                 140

Leu Ser Ser Gly Gly Glu Val Ile Thr Thr Gly Arg Asn Phe Asn Asp
145                 150                 155                 160

Leu Leu Asn Gly Thr Trp Glu Phe Phe Ser Asp Ser Val Val Val Ala
                165                 170                 175

Ser Gln Asn Ala Pro Val Tyr Pro Ala Ser Ala Gly Ala Ala Ala Gly
            180                 185                 190

Met Leu Glu Ala Lys Ser Trp Val Ser Gly Ala Asn Thr Phe Cys Val
        195                 200                 205

Gln Arg Tyr Thr Asp Arg Val Gly Asn Val Ala Val Arg Gly Leu Asn
    210                 215                 220

Ala Gly Ala Trp Thr Asn Trp Met Tyr Ala Val Asn Val Met Ala Leu
225                 230                 235                 240

Gln Gln Gly Arg Val Thr Tyr Gly Val Ala Ala Gly Ser Ala Asn Ala
                245                 250                 255

Tyr Thr Leu Thr Leu Val Pro Gln Leu Gln Gly Gly Leu Val Asp Gly
            260                 265                 270

Met Ile Leu Arg Val Lys Phe Asn Thr Met Asn Thr Gly Ala Ser Thr
        275                 280                 285

Ile Asn Val Ser Gly Leu Gly Ala Lys Ala Ile Val Gly Ala Ala Asn
    290                 295                 300

Phe Pro Leu Thr Gly Gly Glu Leu Gly Gln Gly Leu Ile Ala Glu Leu
305                 310                 315                 320

Val Phe Asp Ala Ala Gly Asp Arg Trp Arg Ile Leu Ala Gly Ala Pro
                325                 330                 335

Arg Ile Gln Val Gly Asn Ala Asp Gln Asp Tyr Gln Ala Pro Ser Trp
            340                 345                 350
```

```
Lys Gln Val Lys Asp Tyr Val Ala Ser Gln Lys Leu Thr Glu Val Asp
            355                 360                 365

Trp Ala Asp Val Val Asn Lys Pro Asn Val Ala Ile Gln Asp Thr Thr
        370                 375                 380

Pro Trp Phe Ala Asn Leu Glu Leu Ser Asp Ala Arg Pro Phe Ile Asp
385                 390                 395                 400

Phe His Phe Asn Ser Asn Arg Ala Lys Asp Phe Asp Tyr Arg Leu Ile
                405                 410                 415

Ser Glu Ala Asp Gly Ser Leu Ala Phe Tyr Ser Arg Gln Gly Ser Ala
            420                 425                 430

Gly Pro Thr Gln Asp Ile Leu Phe Asn Arg Asn Ser Val Thr Phe Phe
        435                 440                 445

Gln Pro Arg Leu Asp Val Ala Lys Asn Leu Ala Tyr Ile Ala Asn Ser
    450                 455                 460

Gly Pro Leu Trp Gln Asn Thr Thr Ala Asp Gln Pro Gly Trp Lys Phe
465                 470                 475                 480

Thr Phe Ala Gln Gly Val Asp Ala Asn Asn Asn Ala Val Ile Ala Val
                485                 490                 495

Asn Thr Thr Asn Pro Asp Gly Ser Tyr Arg Ser Gln Ile Met Arg Trp
            500                 505                 510

Asp Trp Ala Ser Thr Asn Val Ile Phe Asn Asn Arg Pro Leu Phe Ala
        515                 520                 525

Gly Gln Tyr Val Pro Trp Asp Ser Gly Asn Phe Asp Pro Ser Thr Lys
    530                 535                 540

Leu Thr Val Asn Ala Thr Asn Gln Ile Ala Gly Pro Thr Gly Ile Arg
545                 550                 555                 560

Asn Thr Asn Gly Asn Thr Gly Asn Met Asn Thr Trp Gly Ser Gly Ser
                565                 570                 575

Thr Thr Ala Ser Tyr Gly Asn Ala Ala Leu Gln Ile Phe Gly Lys Gly
            580                 585                 590

Gly Gly Glu Pro Ala Ala Leu Tyr Phe Asp Asn Ser Gln Thr Gly Trp
        595                 600                 605

Tyr Leu Gly Met Asp Lys Asp Gly Gln Leu Lys Arg Ala Gly Trp Ser
    610                 615                 620

Leu Gly Asn Asn Ser Tyr Val Ile Thr Asp Glu Ser Asn Ile Arg Thr
625                 630                 635                 640

His Ile Asn Thr Met Ala Ala Arg Pro Ile Trp Gly Asn Val Glu Phe
                645                 650                 655

Trp Gly Pro Trp Asn Phe Asn Pro Asn Thr Lys Leu Thr Leu Gly Ser
            660                 665                 670

Phe Asn Asp Gly Gln His Thr Arg Met Thr Asn Ser Gly Ala Lys Asp
        675                 680                 685

Val Gly Ile Ala Ser Met Thr Ser Tyr Ala Asp Ala Ala Met Ser Phe
    690                 695                 700

Phe Asn Tyr Glu Ala Ser Asn Pro Thr Gly Pro Arg Ala Ala Val Ile
705                 710                 715                 720

Ser Phe Val Arg Asn Gly Ser Arg Gly Val Leu Phe Gly Leu Asp Ser
                725                 730                 735

Asp Asn Lys Leu Lys Trp Gly Gly Tyr Ser Leu Gly Ala Val Ala Phe
            740                 745                 750

Glu Ile Ala Asp Ser Asn Asn Leu Met Ser Leu Trp Ser Ser His Ala
        755                 760                 765

Ala Ala Pro Asn Trp Asn Gly Gln Thr Ile Trp Arg Ser Gly Asn Phe
```

-continued

```
    770                 775                 780

Asn Pro Asp Thr Lys Ala Thr Leu Ala Ala Arg Asn Thr Thr Ser Ser
785                 790                 795                 800

Pro Thr Ile Phe Ser Tyr Gly Ala Ser Gly Ile Ala Ser Thr Gly Gln
                805                 810                 815

Val Gly Ala Leu Val Val Glu Asn Asn Ser Val Thr Asn Thr Ala Ala
            820                 825                 830

Ala Ile Thr Phe His Ser Pro Gln Lys Tyr Gln Val Asn Phe Gly Leu
        835                 840                 845

Asp Ala Asp Asn Val Val Lys Ile Gly Gly Gly Thr Met Gly Gly Val
    850                 855                 860

Ala Tyr Pro Ile Ile His Ser Gly Asn Tyr Asn Asn Tyr Ile Asn Gln
865                 870                 875                 880

Ala Leu Val Gln Val Gly Leu Gly Gly Val Gly Ser Tyr Ala Ile Leu
                885                 890                 895

Ala Val Leu Asp Tyr Ala Ala Pro Thr Ala Thr Val Arg Pro Gly Thr
            900                 905                 910

Ile Met Asp Ser Ser Lys Leu Phe Tyr Ser Ser Cys Asp Ser Thr Tyr
        915                 920                 925

Arg Ser Ser Ala Ser Pro Thr Gly Thr Trp Arg Cys Met Gly Tyr Val
    930                 935                 940

Tyr Asn Arg Asp Ser Thr Asn Gly Asp Ser Ala Ser Leu Phe Gln Arg
945                 950                 955                 960

Val Thr
```